United States Patent
Lazzari et al.

[11] Patent Number: 6,140,326
[45] Date of Patent: Oct. 31, 2000

[54] MORPHOLINONES AS LIGHT STABILIZERS

[75] Inventors: Dario Lazzari, Casalecchio di Reno, Italy; Thomas Bolle, Efringen-Kirchen, Germany; Mirko Rossi, San Lazzaro di Savena, Italy; Hugh Stephen Laver, Reinach, Switzerland

[73] Assignee: Ciba Specialty Chemicals Corporation, Tarrytown, N.Y.

[21] Appl. No.: 09/152,985

[22] Filed: Sep. 14, 1998

[30] Foreign Application Priority Data

Sep. 17, 1997 [EP] European Pat. Off. .............. 97810680

[51] Int. Cl.$^7$ ...................... A61K 31/535; C07D 265/00; C07D 265/30; C07D 265/32
[52] U.S. Cl. .................. 514/231.2; 544/98; 544/171; 544/173; 544/175
[58] Field of Search ................... 544/171, 173, 544/175

[56] References Cited

U.S. PATENT DOCUMENTS

| | | | |
|---|---|---|---|
| 3,324,123 | 6/1967 | Cenker | 260/247.7 |
| 3,371,040 | 2/1968 | Emmons . | |
| 4,528,370 | 7/1985 | Lai | 544/173 |
| 4,602,106 | 7/1986 | Blanc | 562/444 |
| 4,914,232 | 4/1990 | Lai | 562/507 |
| 5,089,614 | 2/1992 | Lai | 544/71 |
| 5,538,840 | 7/1996 | Van Toan et al. | 430/5.2 |

FOREIGN PATENT DOCUMENTS

| | | |
|---|---|---|
| 0 155055 | 9/1985 | European Pat. Off. . |
| 0248494 | 12/1987 | European Pat. Off. . |
| 98/44008 | 10/1998 | WIPO . |

OTHER PUBLICATIONS

Lai Synthesis 1984, 122.
Chem. Abstr. 73:66522k (1970).

*Primary Examiner*—Mukund J. Shah
*Assistant Examiner*—Sudhaker B. Patel
*Attorney, Agent, or Firm*—Luther A. R. Hall; Tyler A. Stevenson

[57] ABSTRACT

The invention relates to new compounds containing 1–8 active groups of the type 3,3,6,6-polysubstituted 2-morpholinone and having the formula F $$(A'-Z)_m-X \quad (F),$$

wherein m is a number from 1 to 8;

X is an organic anchor group of valency m and in case that m is not 1, X may also be a direct bond, $SO_2$, P or PO;

A' is a monovalent group of the formula E

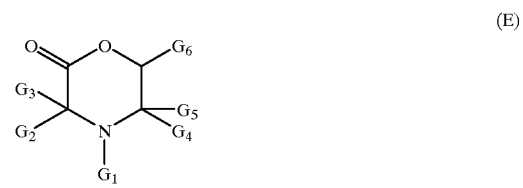

(E)

containing one linking group;

Z is a direct bond, —O—, —S—, —SO—, —$SO_2$— or —$NR'_{14}$—; provided that Z is —O—, —S—, —SO—, —$SO_2$— or —$NR'_{14}$— if m is 1 and the linking group in formula E is $G_3$ or $G_5$;

$G_1$ is hydrogen; $C_1$–$C_{18}$alkyl; $C_2$–$C_{18}$alkyl substituted by OH and/or phenyl; oxyl; OH; $C_2$–$C_{12}$cyanoalkyl; $C_2$–$C_{12}$cyanoalkoxy; $C_1$–$C_{18}$alkoxy; $C_5$–$C_{12}$cycloalkoxy; $C_3$–$C_8$alkenyl; $C_3$–$C_8$alkynyl; $C_3$–$C_8$alkenyloxy; $C_7$–$C_{12}$phenylalkyl; $C_7$–$C_{12}$phenylalkyl substituted by hydroxy, $C_1$–$C_4$alkyl and/or $C_1$–$C_4$alkoxy; $C_7$–$C_{15}$phenylalkoxy; $C_7$–$C_{15}$phenylalkoxy, which is substituted by $C_1$–$C_4$alkyl and/or $C_1$–$C_4$alkoxy; or $G_1$ is $C_1$–$C_8$alkanoyl; $C_3$–$C_5$alkenoyl; $C_1$–$C_{18}$alkanoyloxy; $C_3$–$C_8$epoxyalkyl; or $G_1$ is the linking group —$R_{10}$—;

$G_2$ and $G_4$ are, independently of one another, $C_1$–$C_{18}$alkyl, $C_5$–$C_{12}$cycloalkenyl, $C_5$–$C_{12}$cycloalkyl, or an oligocyclic hydrocarbon residue of 6–12 carbon atoms;

$G_3$ is as defined for $G_2$ or is $C_1$–$C_8$hydroxyalkyl; or $G_2$ and $G_3$ together are $(CH_2)_e$, where e is a number from 4 to 11; or $G_5$ is the linking group —$R_5$—;

$G_5$ is as defined for $G_4$ or is $C_1$–$C_8$hydroxyalkyl; or $G_4$ and $G_5$ together are $(CH_2)_e$, where e is number from 4 to 11; or $G_5$ is the linking group —$R_5$—; $G_6$ is as defined for $G_4$ or is hydrogen;

or $G_6$ is the linking group, which is a direct bond or —$R_5$—;

and other residues are as defined in claim 1. The new compounds are effective as stabilizers for organic material, especially coatings, against harmful effects of light, oxygen and/or heat.

11 Claims, No Drawings

MORPHOLINONES AS LIGHT STABILIZERS

The invention relates to new 3,3,5,5-tetrasubstituted 2-morpholinones, their use as stabilizers for organic material against deleterious effects of light, oxygen and/or heat, organic material correspondingly stabilized and a process for stabilizing organic material.

Structure and numbering of 2-morpholinone is as shown in the formula:

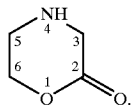

An important type of stabilizers for organic material are the hindered amine light stabilizers, whose chemical structure is usually derived from 2,2,6,6-tetramethylpiperidine.

The use of some 3,3-disubstituted 2-morpholinones as an additive for fuels or lubricants is described in U.S. Pat. No. 3,371,040.

U.S. Pat. Nos. 4,528,370, 4,914,232 and 5,089,614 disclose as a new class of light stabilizers for organic materials some specific 3,3,5,5-tetrasubstituted 2-morpholinones. Some of these compounds are also described by J. T. Lai in Synthesis (1984), 122.

EP-A-248494 describes the formation of a polybutadiene capped by reaction with 3,3,5,5-tetramethyl-morpholin-2-one.

It has now been found that a modified class of compounds of the 2-morpholinone type is especially well suitable for protecting organic material against harmful effects of light, oxygen and/or heat.

Object of the invention is therefore a compound of the formula F $$(A'—Z)_m—X \quad (F),$$

wherein m is a number from 1 to 8;

Z is a direct bond, —O—, —S—, —SO—, —SO$_2$— or —NR'$_{14}$—;

X is an organic anchor group of valency m comprising 1–300 carbon and 0–60 hetero atoms; and in case that m is not 1, X may also be a direct bond, SO$_2$, P or PO;

A' is a monovalent group of the formula E

(E)

containing one linking group;

G$_1$ is hydrogen; C$_1$–C$_{18}$alkyl; C$_2$–C$_{18}$alkyl substituted by OH and/or phenyl; oxyl; OH; C$_2$14 C$_{12}$cyanoalkyl; C$_2$–C$_{12}$cyanoalkoxy; C$_1$–C$_{18}$alkoxy; C$_5$–C$_{12}$cycloalkoxy; C$_3$–C$_8$alkenyl; C$_3$–C$_8$alkynyl; C$_3$–C$_8$alkenyloxy; C$_7$–C$_{12}$phenylalkyl; C$_7$–C$_{12}$phenylalkyl substituted by hydroxy, C$_1$–C$_4$alkyl and/or C$_1$–C$_4$alkoxy; C$_7$–C$_{15}$phenylalkoxy; C$_7$–C$_{15}$phenylalkoxy, which is substituted by C$_1$–C$_4$alkyl and/or C$_1$–C$_4$alkoxy; or G$_1$ is C$_1$–C$_8$alkanoyl; C$_3$–C$_5$alkenoyl; C$_1$–C$_{18}$alkanoyloxy; C$_3$–C$_8$epoxyalkyl;

or G$_1$ is the linking group —R$_{10}$—;

G$_2$ and G$_4$ are, independently of one another, C$_1$–C$_{18}$alkyl, C$_3$–C$_8$alkenyl, C$_5$–C$_{12}$cycloalkenyl, C$_5$–C$_{12}$cycloalkyl, or an oligocyclic hydrocarbon residue of 6–12 carbon atoms;

G$_3$ is as defined for G$_2$ or is C$_1$–C$_8$hydroxyalkyl; or G$_2$ and G$_3$ together are (CH$_2$)$_e$, where e is number from 4 to 11;

or G$_3$ is the linking group —R$_5$—;

G$_5$ is as defined for G$_4$ or is C$_1$–C$_8$hydroxyalkyl; or G$_4$ and G$_5$ together are (CH$_2$)$_e$, where e is a number from 4 to 11;

or G$_5$ is the linking group —R$_5$—;

G$_6$ is as defined for G$_4$ or is hydrogen;

or G$_6$ is the linking group, which is a direct bond or —R$_5$—;

R$_5$ is C$_1$–C$_8$alkylene; C$_1$–C$_8$alkylene-CO—; or C$_1$–C$_8$alkylene substituted by OH or OCOR$_{15}$;

R$_{10}$ is C$_1$–C$_8$alkylene or —CO— or C$_1$–C$_8$alkylene-CO—;

R'$_{10}$ is hydrogen or C$_1$–C$_8$alkyl or C$_5$–C$_{12}$cycloalkyl;

R'$_{14}$ is hydrogen, C$_1$–C$_{18}$alkyl; C$_5$–C$_{12}$cycloalkyl; C$_3$–C$_{18}$alkyl interrupted by O or NR'$_{10}$; C$_5$–C$_{12}$cycloalkyl, which is substituted by C$_1$–C$_4$alkyl; C$_2$–C$_{17}$alkenyl; C$_7$–C$_{15}$phenylalkyl; C$_7$–C$_{15}$phenylalkyl, which is substituted by C$_1$–C$_4$alkyl, C$_1$–C$_4$alkoxy;

R$_{15}$ is hydrogen; C$_1$–C$_{17}$alkyl; C$_3$–C$_{50}$alkyl interrupted by O; C$_5$–C$_{12}$cycloalkyl; C$_5$–C$_{12}$cycloalkyl, which is substituted by C$_1$–C$_4$alkyl; C$_2$–C$_{17}$alkenyl; phenyl; phenyl which is substituted by C$_1$–C$_4$alkyl, C$_1$–C$_4$alkoxy and/or hydroxy; C$_7$–C$_{15}$phenylalkyl; C$_7$–C$_{15}$phenylalkyl, which is substituted by C$_1$–C$_4$alkyl, C$_1$–C$_4$alkoxy and/or hydroxy; or is C$_8$–C$_{12}$phenylalkenyl;

provided that Z is —O—, —S—, —SO—, —SO$_2$— or —NR'$_{14}$— if m is 1 and the linking group in formula E is G$_3$ or G$_5$.

All residues may be straight chain or branched unless otherwise indicated.

An oligocyclic hydrocarbon residue of 6–12 carbon atoms is mainly bicycloalkyl, bicycloalkenyl, tricycloalkyl or tricycloalkenyl of 6–12 carbon atoms.

A substituent halogen is —F, —Cl, —Br or —I; preferably —F or —Cl, especially —Cl.

Alkali metal is mainly Li, Na, K, Rb, Cs, especially Na or K; it is often present as cation forming a salt of a carboxy group.

Open bonds in alkylene or cycloalkylene residues may be attached on different carbon atoms or on the same carbon atom, thus embracing alkylidene or cycloalkylidene. Alkylidene and cycloalkylidene are saturated divalent hydrocarbons having both open bonds localized on the same carbon atom; for instance, C$_1$–C$_4$alkylidene embraces C$_1$alkylidene which is methylene.

Organic residues like X as an organic anchor group are hydrocarbons which may additionally contain hetero atoms as specified. A hydrocarbon alone, i.e. without hetero atoms, consists of carbon and hydrogen; if there is more than one carbon atom present, these can be linked to each other by single, double or triple bonds, open bonds being linked to hydrogen as known in organic chemistry.

Of pronounced value are compounds of the formula F wherein m is 1 and X contains at least 5 carbon or hetero atoms, especially 5 carbon atoms, or wherein m is a number from the range 2–8.

Preferably, X is an m-valent hydrocarbon radical consisting of 1–100 carbon atoms, or is an m-valent organic radical consisting of 1–200 carbon atoms and 1–60 hetero atoms selected from N, O, S, halogen, P, Si, alkali metal, Ca and Zn, and hydrogen atoms, or X is P.

Usually, m is the number of groups of the 2-morpholinone type in compounds of the formula F, and X does not comprise a group of the 2-morpholinone type.

Hetero atoms are non-carbon and non-hydrogen atoms, for instance N, O, S, halogen, P, Si; alkali metal, Ca or Zn can be contained e.g. as carboxylate. Preferred hetero atoms are N, O, S or P, especially N, S and O.

Organic residues or hydrocarbons containing heteroatoms, such as alkyl or alkylene interrupted by hetero groups like oxygen or NH, usually contain these heteroatoms as typical functional groups like oxo, oxa, hydroxy, carboxy, ester, amino, amido, nitro, nitrilo, isocyanato, fluoro, chloro, bromo, phosphate, phosphonate, phosphite, silyl, thio, sulfide, sulfinyl, sulfo, heterocyclyl including pyrrolyl, indyl, carbazolyl, furyl, benzofuryl, thiophenyl, benzothiophenyl, pyridyl, chinolyl, isochinolyl, pyridazinyl, pyrimidinyl, pyrazinyl, triazolyl, benzotriazolyl, triazinyl, pyrazolyl, imidazolyl, thiazolyl, oxazolyl, and corresponding saturated and/or substituted groups like, for example, piperidyl, piperazinyl, morpholinyl etc. They may be interrupted by one or more of these groups; usually there are no linkages of the type O—O, O—N (except nitro, cyanato, isocyanato, nitroso), N—N (except in heterocyclic ring structures), N—P or P—P present, regardless of the order.

Preferably, in organic residues or hydrocarbons containing heteroatoms, for example alkyl or alkylene residues like X, $R_5$ or $R_{10}$, there is not more than one heteroatom attached by a single bond to the same carbon atom. A spacer consisting of one or more heteroatoms such as defined below usually is embedded in a carbon chain or ring or inserted into a carbon-hydrogen bond.

Preferred compounds are those wherein $R_5$ is $C_1$–$C_4$alkylene, especially methylene, and $R_{10}$ is —$CH_2$—CH(R')— with R' being H or $C_1$–$C_4$alkyl and Z is O.

Z is preferably a direct bond, —O— or —$NR'_{14}$—; especially —O— or —$NR'_{14}$—.

When Z in formula F is a direct bond, X directly bonds to A; when a linking group in formula E is a direct bond, the morpholinone ring directly bonds to Z or, if Z is also a direct bond, to X. In case that both Z and X are direct bonds, 2 moieties of the formula E are directly linked together.

Also preferred are compounds of formula F, wherein $G_1$ is the linking group —$CH_2$—CH(R')— with R' being H or $C_1$–$C_4$alkyl and Z is as defined, or $G_5$ is the linking group $C_1$–$C_4$alkylene, Of particular interest are compounds of the formula F, wherein X is an aliphatic or aromatic or mixed aliphatic-aromatic hydrocarbon of valency m, or an aliphatic or aromatic or mixed aliphatic-aromatic hydrocarbon of valency m containing one or more heteroatoms in the form of one or more spacers selected from O, N, $N_2$, $N_3$, S, SO, $SO_2$, $SO_3$, $SO_4$, O=P(O)$_3$, P(O)$_3$, Si, SiO, $SiO_2$ between carbon and hydrogen or/and between carbon atoms, and/or one or more substituents selected from O, N and halogen; or X is P, PO or a direct bond; and wherein, when m is 1, X comprises 1–60 carbon and 0–15 hetero atoms;

when m is 2, X comprises 1–60 carbon atoms and 0–15 hetero atoms, or X is a direct bond;

when m is 3, X comprises 1–60 carbon atoms and 0–15 hetero atoms, or X is P or PO;

when m is 4, X comprises 1–60 carbon atoms and 0–15 hetero atoms;

when m is 5, X comprises 5–60 carbon atoms and 0–15 hetero atoms;

when m is 6, X comprises 6–100 carbon atoms and 0–30 hetero atoms;

when m is 7, X comprises 7–100 carbon atoms and 0–30 hetero atoms;

when m is 8, X comprises 8–200 carbon atoms and 0–60 hetero atoms.

Examples for X are the following meanings when m is 1:

X as an acyl group of a monocarboxylic or sulfonic acid of 2–18 carbon atoms; an alkyl group of 1–18 carbon atoms; said alkyl or alkyl of 2–50 carbon atoms interrupted by O, S, ester, amido, phosphite, phosphate or $NR'_{14}$, and/or substituted by oxo, CN, halogen; or an alkenyl group of 2–8 carbon atoms; also of certain interest are compounds, wherein X comprises a group —Z—$R_5$—D or —Z—D, where D is a stabilizer moiety, e.g. selected from 3,3,5,5-tetramethylpiperazin-2-one or 3,3,5,5-tetramethylpiperazin-2,6-dione e.g. bonded in position 1, polyalkylpiperidine such as 2,2,6,6-tetramethylpiperidine bonded in position 1 or 4, 2'-hydroxyphenylbenztriazole e.g. bonded on the phenyl ring in position 3' or 5', 2-hydroxybenzophenone e.g. bonded in position 3, 4 or 4', oxalanilide bonded on one of the phenyl rings, 2-hydroxyphenyl-s-triazine e.g. bonded on one of the phenyl rings in position 4, 2,6-dialkylphenol e.g. bonded in position 4, or 4-phenylaminophenyl, or one of these moieties substituted by $C_1$–$C_4$alkyl, $C_1$–$C_{12}$alkoxy or halogen; examples include an acyl group of a dicarboxylic acid of 2–18 carbon atoms, wherein one of the carbonyl groups forms an ester or amide with a group —Z—$R_5$—D or —Z—D, or alkyl of 1–18 carbon atoms substituted by one of these groups;

when m is 2:

X as a direct bond; alkylene; $C_2$–$C_{50}$alkylene interrupted by O, arylene, phosphite, phosphate, ester, carbonyl, cycloalkylene, S, $NR'_{14}$ and/or substituted by OH, $C_1$–$C_{18}$alkoxy, —N($R'_{14}$)$_2$, CN, cycloalkoxy, allyloxy, halogen, carboxy, amido, phenyl, phenoxy and/or $C_1$–$C_{18}$alkyl-, $C_1$–$C_{18}$alkoxy- or halo-substituted phenoxy; or as divalent aliphatic, aromatic or mixed aliphatic-aromatic groups like cycloalkylene; phenylene; cycloalkylene-alkylene; phenylenealkylene; alkylene interrupted by cycloalkylene and/or phenylene; or 2 or more cycloalkylene and/or phenylene connected by direct bonds or separated by the spacer E, wherein E is alkylene, —O—, —S—, —$SO_2$—, —CO—; or X as carbonyl or alkylene-carbonyl or diacyl, e.g. of a dicarboxylic acid of 2–18 carbon atoms;

when m is 3:

X as $C_3$–$C_{18}$alkantriyl; triacyl of a tricarboxylic acid of 4–18 carbon atoms; triazinyl or triazinyl connected over the spacers (CO)$_i$-alkylene-O— or (CO)$_i$-alkylene-$NR'_{14}$—, where i is 0 or 1; or a phosphite, phosphonite or phosphate;

when m is 4:

X as $C_5$–$C_{18}$alkantetryl; tetracyl of a tetracarboxylic acid of 5–18 carbon atoms; triazinyl-$NR'_{14}$-alkylene-$NR'_{14}$- triazinyl connected directly or over the spacers (CO)$_i$-alkylene-O— or (CO)$_i$-alkylene-NR'$_{14}$— as above;

when m is 6:

X as C$_6$–C$_{18}$alkanhexayl; hexacyl of a hexacarboxylic acid of 9–24 carbon atoms; triazinyl-NR'$_{14}$-alkylene-N(triazinyl)-alkylene-NR'$_{14}$-triazinyl connected directly or over the spacers (CO)$_i$-alkylene-O— or (CO)$_i$-alkylene-NR'$_{14}$— as above; or triazinyl connected to 3 groups N(alkylene-CO)$_2$ or N(alkylene-)$_2$;

when m is 8:

X as C$_8$–C$_{18}$alkanoctoyl; octoacyl of an octocarboxylic acid of 9–24 carbon atoms; or a group triazinyl-NR'$_{14}$-alkylene-N(triazinyl)-alkylene-N(triazinyl)-alkylene-NR'$_{14}$-triazinyl connected directly or over the spacers (CO)$_i$-alkylene-O— or (CO)$_i$-alkylene-NR'$_{14}$— as above; or a group triazinyl-NR'$_{14}$-alkylene-NR'$_{14}$-triazinyl connected to 4 groups N(-alkylene-CO)$_2$ or N(alkylene)$_2$.

Alkyl is a monovalent residue of the formula C$_n$H$_{(2n+1)}$ wherein n denotes the number of carbon atoms. Alkylene, alkantriyl, alkanetetrayl, alkanepentayl, alkanehexayl, alkaneheptayl, alkaneoctayl are corresponding di, tri, tetra, penta, hexa, hepta or octovalent alkanes wherein each bond reduces the number of hydrogen atoms in the general formula C$_n$H$_{(2n+2)}$ by 1.

Acyl groups carboxylic or sulfonic acids mainly contain 2–18 carbon atoms and include aliphatic, aromatic or mixed aliphatic/aromatic acids; within the definitions given, these groups may contain ethylenic double bonds and/or further hetero atoms, e.g. as oxo, oxa, aza, thio. Triazinyl groups mentioned are 1,3,5-triazine-2,4,6-triyl.

Acyl residues such as aliphatic or aromatic mono-, di-, tri-, tetra-, penta-, hexa-, hepta- or octoacyl are residues of mono-, di-, tri-, tetra-, penta-, hexa-, hepta- or octocarbonic acids of the formula A—(CO—)$_n$, wherein n is 1 for mono-, 2 for di-, 3 for tri-, 4 for tetra-, 5 for penta- and 6 for hexaacyl, 7 for hepta- and 8 for octoacyl. The CO groups in aliphatic acyl groups bind to non-aromatic carbon, those in aromatic acyl groups bind to aromatic carbon. Thus, aromatic acyl includes residues of benzene, naphthyl and biphenyl carboxylic acids, which can be further substituted e.g. by C$_1$–C$_{12}$alkyl, C$_1$–C$_{12}$alkoxy, C$_2$–C$_8$ alkenyl, OH, halogen, cyclohexyl and/or phenyl, such as benzene tri-, tetra-, penta- or hexacarboxylic acid, naphthalene tricarboxylic acid. Aliphatic acyl includes residues of alkyl, alkenyl and cycloalkyl carboxylic acids, which can be further substituted e.g. by C$_1$–C$_{12}$alkoxy, C$_2$–C$_8$alkenyl, OH, halogen, cyclohexyl, heterocyclyl, C$_1$–C$_4$alkylcyclohexyl, phenyl and/or phenyl substituted by C$_1$–C$_4$alkyl or C$_1$–C$_4$alkoxy or OH or halogen, or in interrupted e.g. by O, N or phenyl.

Within the definitions given, acyl groups can be aromatic, aliphatic, mixed aromatic-aliphatic, cycloaliphatic or bicycloaliphatic or unsaturated, for example derived from the following acids:

caprylic acid, capric acid, acetic acid, stearic acid, polyisobutenylsuccinic acid, n-hexacosanoic acid , trimethylacetic acid, propionic acid, butyric acid, isovaleric acid, lauric acid, oleic acid, acrylic acid, methacrylic acid, sorbic acid, linolenic acid, dibasic acids, such as malonic acid, methylenemalonic acid, maleic or fumaric acid, itaconic acid, glutaconic acid, oxalic acid, succinic acid, iso-dodecylsuccinic acid, glutaric acid, adipic acid, pimelic acid, suberic acid, azelic acid or sebacic acid, or hydroxy acids like citric acid, or

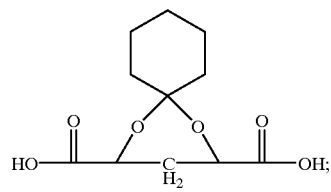

polybasic acids like butane-1,2,3,4-tetracarboxylic acid;

the polymers of fatty acids, such as the dimers and trimers thereof of the type described, for example, in Ind. and Eng. Chem. 33, 86–89 (1941), hetero atom-containing acids, for example, nitrilotriacetic acid, tetrahydrofurane-2,3,4,5-tetracarboxylic acid;

cycloaliphatic acids, such as cyclohexanecarboxylic acid, 1,2- and 1,4-cyclohexanedicarboxylic acid, cyclopentanecarboxylic acid, cyclopentylacetic acid, 3-methylcyclopentylacetic acid, camphor acid, 4-methylcyclohexanecarboxylic acid and 2,4,6-trimethylcyclohexanecarboxylic acid, bicyclo[2.2.2]octa-5-ene-2,3-dicarboxylic acid and bicyclo[2.2.1]hepta-5-ene-2-carboxylic acid, aromatic carboxylic acids, such as benzoic acid, o-, m- and p-toluic acid, phthalic acid, isophthalic acid, terephthalic acid, trimellitic acid, trimesic acid, 1,2,4,5-benzenetetracarboxylic acid, diphenic acid, naphthenic acids, including, for example, 1-naphthoic acid, 2-naphthoic acid, naphthalene-1,8-dicarboxylic acid, naphthalene-1,4-dicarboxylic acid, naphthalene-1,4,5-tricarboxylic acid and the like, paraffinic ω-aryl acids, such as phenylacetic acid, hydrocinnamic acid, phenylbutyric acid, γ-(1-naphthyl)butyric acid, δ-phenylene-n-valeric acid, ε-phenyl-n-caproic acid, o-, m- or p-phenylenediacetic acid or o-phenyleneacetic-β-propionic acid, and also unsaturated phenyl acids, for example, cinnamic acid or the acids 2,2-dicarboxyethenylbenzene of formula

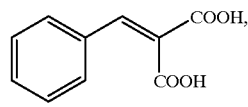

or corresponding substituted derivatives such as 2,2-dicarboxyethenylbenzene substituted in the benzene moiety by C$_1$–C$_4$alkyl, C$_1$–C$_4$alkoxy, or 1 or 2 further residues 2,2-dicarboxyethen-1-yl.

Preferred is a compound of the formula F which also corresponds to a formula A, B, C or D (A)

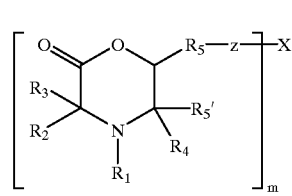

-continued

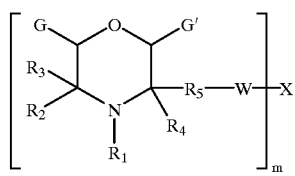
(B)

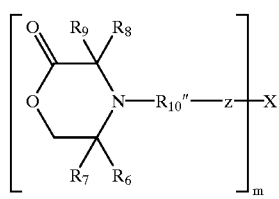
(C)

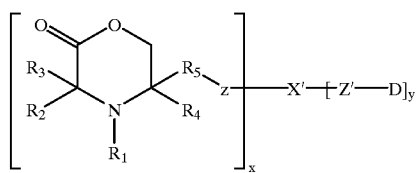
(D)

where m is the valency of X and is an integer from the range 1–8, x and y are each integers from the range 1–7 obeying the condition x+y=m;

G is =O and G' is H or $R'_5$; or G' is =O and G is H or $R'_5$;

$R_1$ is hydrogen; $C_1$–$C_{18}$alkyl; $C_2$–$C_{18}$alkyl substituted by OH and/or phenyl; oxyl; OH; $C_2$–$C_{12}$cyanoalkyl; $C_2$–$C_{12}$cyanoalkoxy; $C_1$–$C_{18}$alkoxy; $C_5$–$C_{12}$cycloalkoxy; $C_3$–$C_8$alkenyl; $C_3$–$C_8$alkynyl; $C_3$–$C_8$alkenyloxy; $C_7$–$C_{12}$phenylalkyl; $C_7$–$C_{12}$phenylalkyl substituted in the alkyl moiety by hydroxy; $C_7$–$C_{15}$phenylalkyl, which is substituted on the phenyl ring by 1, 2 or 3 radicals selected from $C_1$–$C_4$alkyl and $C_1$–$C_4$alkoxy; $C_7$–$C_{15}$phenylalkoxy; $C_7$–$C_{15}$phenylalkoxy, which is substituted on the phenyl ring by 1, 2 or 3 radicals selected from $C_1$–$C_4$alkyl and $C_1$–$C_4$alkoxy; or $R_1$ is $C_1$–$C_8$alkanoyl; $C_3$–$C_5$alkenoyl; $C_1$–$C_{18}$alkanoyloxy; glycidyl;

$R_2$, $R_4$, $R'_5$, $R_6$, $R_7$, $R_8$ and $R_9$ are, independently of one another, $C_1$–$C_{18}$alkyl, $C_3$–$C_8$alkenyl, $C_5$–$C_{12}$cycloalkenyl, $C_5$–$C_{12}$cycloalkyl, $C_6$–$C_{12}$bicycloalkenyl, or $C_6$–$C_{12}$bicycloalkyl;

$R_3$ is $C_1$–$C_8$hydroxyalkyl, $C_1$–$C_{18}$alkyl or $C_5$–$C_{12}$cycloalkyl;

or $R_2$ and $R_3$, $R_4$ and $R'_5$, $R_6$ and $R_7$, $R_8$ and $R_9$ form, together with the carbon atom they are attached to, $C_5$–$C_{12}$cycloalkylene;

$R_5$ is $C_1$–$C_8$alkylene; $C_1$–$C_8$alkylene-CO—; and in formula A also may be a direct bond; and may be also $C_1$–$C_8$alkylene substituted by OH or $OCOR_{15}$, provided that the OH or $OCOR_{15}$ group does not bond directly to a carbon atom that also bonds directly to —O— or —$NR'_{14}$—;

$R_{10}$ is $C_2$–$C_8$alkylene; $C_1$–$C_8$alkylene-CO—;

$R'_{10}$ is hydrogen or $C_1$–$C_8$alkyl or $C_5$–$C_{12}$cycloalkyl;

W is —O— or —$NR'_{14}$— and, if m is not 1, W can also be a direct bond;

X' is as defined for X below;

Y is —O— or —$NR'_{14}$—;

Z and Z', independently, are a direct bond or have a meaning given for Y;

when m is 1, X is $C_1$–$C_{18}$alkyl; $C_1$–$C_{18}$alkyl substituted by $C_1$–$C_{18}$alkoxy, —$N(R'_{14})_2$, —OH, —OCO—$R_{11}$, —$COR_{11}$, —$COOR_{13}$, CN, —$(O)_i$—$P(=O)_i(OR_{111})_2$, $C_5$–$C_{12}$cycloalkoxy, allyloxy, halogen, —COOH, —$CON(R'_{14})_2$, phenoxy and/or $C_1$–$C_{18}$alkyl-, $C_1$–$C_{18}$alkoxy- or halo-substituted phenoxy; or X is —$P(=O)_i(OR_{111})_2$; $C_3$–$C_{30}$alkyl which is interrupted by —O— and can be substituted by OH; $C_5$–$C_{12}$cycloalkyl; $C_3$–$C_6$alkenyl; glycidyl; $C_7$–$C_{15}$phenylalkyl; $C_7$–$C_{15}$phenylalkyl, which is substituted on the phenyl ring by a radical selected from $C_1$–$C_4$alkyl and $C_1$–$C_4$alkoxy; —$SO_2$—$R'_{11}$; or is a group of formulae IIIa–IIIe —CO—$R_{11}$ (IIIa)

—$R_{12}$—COO—$R_{13}$ (IIIb)

—CO—NH—$R_{14}$ (IIIc)

—CO—$R_{18}$—COO—$R'_{17}$ (IIId)

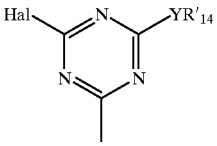
(IIIe)

and in formulae A and C, X can also be hydrogen or CN;

i is 0 or 1;

Hal stands for halogen or a residue Y—$R'_{14}$;

$R_{11}$ is hydrogen; $C_1$–$C_{18}$alkyl; $C_1$–$C_{18}$alkyl substituted by $C_1$–$C_{18}$alkoxy, —$N(R'_{14})_2$, —OH, —OCO—$R_{111}$, —$COR_{111}$, CN, —$(O)_i$—$P(=O)_i(OR_{111})_2$, $C_5$–$C_{12}$cycloalkoxy, allyloxy, halogen, —COOH, —$CON(R'_{14})_2$ and/or phenoxy and/or $C_1$–$C_{18}$alkyl-, $C_1$–$C_{18}$alkoxy- or halo-substituted phenoxy; $C_3$–$C_{50}$alkyl interrupted by O; $C_5$–$C_{12}$cycloalkyl; $C_5$–$C_{12}$cycloalkyl, which is substituted by $C_1$–$C_4$alkyl; $C_2$–$C_{17}$alkenyl; phenyl; phenyl which is substituted by a radical selected from $C_1$–$C_4$alkyl, $C_1$–$C_4$alkoxy and hydroxy; $C_7$–$C_{15}$phenylalkyl; $C_7$–$C_{15}$phenylalkyl, which is substituted on the phenyl ring by 1, 2 or 3 radicals selected from $C_1$–$C_4$alkyl, $C_1$–$C_4$alkoxy and hydroxy; or $C_8$–$C_{12}$phenylalkenyl;

$R'_{11}$ is phenyl; phenyl which is substituted by a radical selected from $C_1$–$C_4$alkyl, $C_1$–$C_4$alkoxy and hydroxy; naphthyl; $C_7$–$C_{15}$phenylalkyl; $C_1$–$C_{17}$alkyl; $C_5$–$C_{12}$cycloalkyl;

$R_{111}$ is $C_1$–$C_{12}$alkyl or phenyl or $C_7$–$C_{15}$alkylphenyl;

$R_{12}$ is a direct bond, $C_1$–$C_{18}$alkylene or carbonyl;

$R_{13}$ is $C_1$–$C_{18}$alkyl; $C_3$–$C_{18}$alkenyl; $C_5$–$C_{12}$cycloalkyl; $C_5$–$C_{12}$cycloalkyl, which is substituted by 1, 2 or 3 $C_1$–$C_4$alkyl;

$R_{14}$ is $C_1$–$C_{18}$alkyl; $C_5$–$C_{12}$cycloalkyl; $C_5$–$C_{12}$cycloalkyl, which is substituted by 1, 2 or 3 $C_1$–$C_4$alkyl; $C_2$–$C_{17}$alkenyl; $C_2$–$C_8$hydroxyalkyl; $C_7$–$C_{15}$phenylalkyl; $C_7$–$C_{15}$phenylalkyl, which is substituted on the phenyl ring by 1, 2 or 3 radicals selected from $C_1$–$C_4$alkyl, $C_1$–$C_4$alkoxy;

$R'_{14}$ is hydrogen or has one of the meanings given for $R_{14}$;

$R_{16}$ is $C_1$–$C_{18}$alkyl or $C_3$–$C_8$alkenyl;

$R_{17}$ is hydrogen or $C_1$–$C_4$alkyl;

$R'_{17}$ embraces the meanings given for $R_{13}$ above or is hydrogen or one equivalent of a metal of main group I or II of the periodic system;

when m is 2, X is $C_2$–$C_{18}$alkylene; $C_4$–$C_{12}$alkylene interrupted by oxygen, phenylene, $C_5$–$C_{12}$cycloalkylene, S, $NR'_{14}$ and/or substituted by OH, $C_1$–$C_{18}$alkoxy, —$N(R'_{14})_2$, —OCO—$R_{11}$, —$COR_{11}$, —$COOR'_{17}$, CN, —(O)$_i$—P(=O)$_i$(OR$_{111}$)$_2$, $C_5$–$C_{12}$cycloalkoxy, allyloxy, halogen, —COOH, —CON(R'$_{14}$)$_2$, phenoxy and/or $C_1$–$C_{18}$alkyl-, $C_1$–$C_{18}$alkoxy- or halo-substituted phenoxy; or X is —P(=O)$_i$(OR$_{111}$)—; $C_5$–$C_{12}$cycloalkylene; phenylene; $C_5$–$C_{12}$cycloalkylene-$C_1$–$C_4$alkylene; phenylene-$C_1$–$C_4$alkylene; $C_2$–$C_8$alkylene interrupted by $C_5$–$C_{12}$cycloalkylene and/or phenylene; $C_5$–$C_{12}$cycloalkylene-E-$C_5$–$C_{12}$cycloalkylene; -phenylene-E-phenylene-, wherein E is $C_1$–$C_4$alkylene, —O—, —S—, —SO$_2$—, —CO—; or X is carbonyl or $C_1$–$C_7$alkylene-carbonyl or a group of formulae IVa–IVi —CO—$R_{18}$—CO— (IVa)

—COO—$R_{19}$—OCO— (IVb)

—CONH—$R_{20}$—NHCO— (IVc)

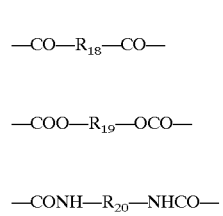
(IVd)

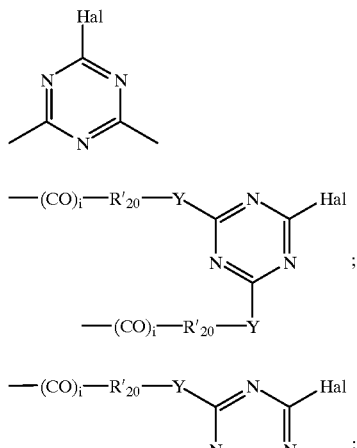
(IVe)

(IVf)

(IVg)

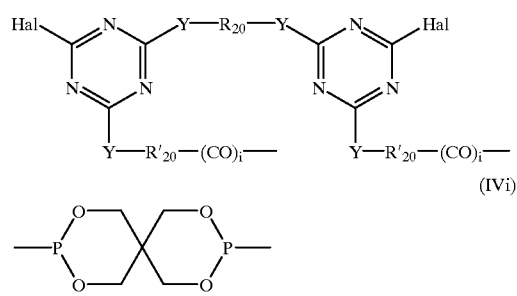
(IVh)

(IVi)

in which i is 0 or 1;

$R_{18}$ is a direct bond; $C_1$–$C_{22}$alkylene; $C_2$–$C_{22}$alkylene interrupted by oxygen, phenylene, $C_5$–$C_{12}$cycloalkylene, sulfur, $NR'_{14}$ and/or substituted by OH, $C_1$–$C_{18}$alkoxy, —$N(R'_{14})_2$, —OCO—$R_{11}$, —$COR_{11}$, —$COOR_{13}$, CN, —(O)$_i$—P(=O)$_i$(OR$_{111}$)$_2$, $C_5$–$C_{12}$cycloalkoxy, allyloxy, halogen, —COOH, —CON(R'$_{14}$)$_2$, phenoxy and/or $C_1$–$C_{18}$alkyl-, $C_1$–$C_{18}$alkoxy- or halo-substituted phenoxy; $C_2$–$C_8$alkenylene; or $R_{18}$ is $C_2$–$C_8$alkenylene substituted by $R_{21}$; $C_2$–$C_8$alkylene substituted by $R_{21}$; $C_5$–$C_{12}$cycloalkylene; $C_5$–$C_{12}$cycloalkenylene; or phenylene;

$R_{19}$ is $C_2$–$C_{12}$alkylene; $C_4$–$C_{12}$alkylene interrupted by oxygen, phenylene and/or $C_5$–$C_{12}$cycloalkylene; $C_5$–$C_{12}$cycloalkylene; bis($C_5$–$C_{12}$cycloalkylene)-$C_1$–$C_4$alkylene;

$R_{20}$ is $C_2$–$C_{12}$alkylene; $C_4$–$C_{18}$alkylene interrupted by O, $NR'_{14}$, S, $C_5$–$C_{12}$cycloalkylene or/and phenylene; or $R_{20}$ is $C_5$–$C_{12}$cycloalkylene; or phenylene;

$R'_{20}$ is $C_2$–$C_{12}$alkylene; $C_5$–$C_{12}$cycloalkylene; phenylene; and if i is 1, $R'_{20}$ additionally embraces methylene;

$R_{21}$ is phenyl; phenyl which is substituted by 1, 2 or 3 radicals selected from $C_1$–$C_4$alkyl, $C_1$–$C_4$alkoxy, di($C_1$–$C_4$alkyl)amino, nitro, hydroxy; or is naphthyl; or naphthyl which is substituted by $C_1$–$C_4$alkyl, $C_1$–$C_4$alkoxy, di($C_1$–$C_4$alkyl)amino, nitro; or $R_{21}$ is thienyl; phenoxyphenyl; thiophen-2-yl; phenylthiophenyl; benzo[b]thiophen-2-yl; benzofuran-2-yl; 9H-fluorenyl; biphenylyl; 10-($C_1$–$C_8$alkyl)-10H-phenothiazinyl;

and if the linking group Z or W is a direct bond, X also may be $C_1$alkylene or Y;

when m is 3, X is $C_3$–$C_{18}$alkanetriyl; P; PO; $C_4$–$C_{18}$triacyl; 1,3,5-triazine-2,4,6-triyl; or a group of formula

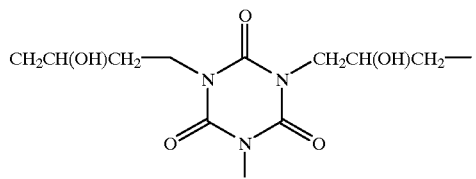
(VIIa)

or

-continued

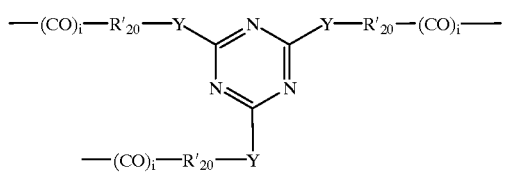
(VIIb)

or a trivalent residue of the formula VIIc

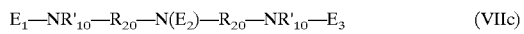
(VIIc)

wherein $E_1$, $E_2$ and $E_3$, independently of one another, are a group of formula IVf;

when m is 4, X is $C_5$–$C_{18}$alkanetetryl; $C_6$–$C_{18}$tetraacyl; or a group of the formula

(VIIIb)

wherein $Z_1$ and $Z_2$ are each, independently of one another, 1,3,5-triazine-2,4,6-triyl or a group of the formula VIIIc or VIIId

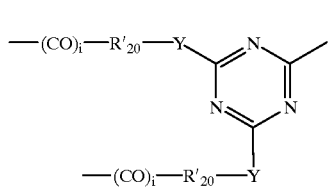
(VIIIc)

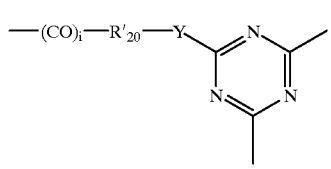
(VIIId)

and the group of formula VIIIc–d is attached via a bond from the triazine ring to the nitrogen atom in formula VIIIb;

when m is 5, X is $C_5$–$C_{18}$alkanepentayl; or $C_7$–$C_{18}$pentaacyl;

when m is 6, X is $C_9$–$C_{18}$hexaacyl; or a hexavalent residue of the formula IXa or IXb

(IXa)

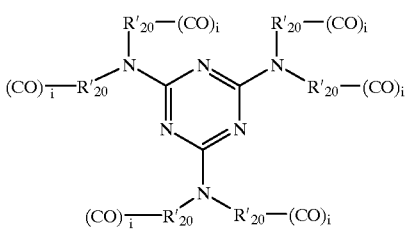
(IXb)

wherein $Z_1$, $Z_2$ and $Z_3$, independently of one another, are 1,3,5-triazine-2,4,6-triyl or a group of the formula VIIIc or VIIId, which is attached via a bond from the triazine ring to the nitrogen atom in formula IXa;

when m is 7, X is $C_{10}$–$C_{18}$heptaacyl;

when m is 8, X is $C_9$–$C_{18}$octoacyl; or an octovalent residue of the formula Xa or Xb

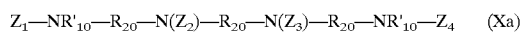
(Xa)

(Xb)

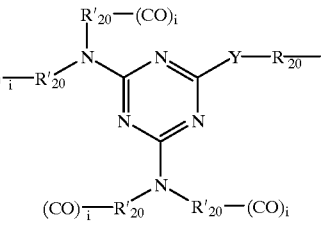

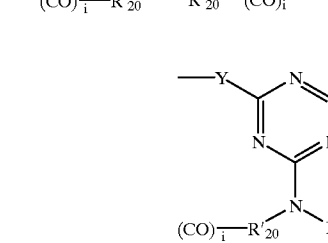

wherein $Z_1$, $Z_2$, $Z_3$ and $Z_4$, independently of one another, are 1,3,5-triazine-2,4,6-triyl or a group of the formula VIIIc or VIIId, which is attached via a bond from the triazine ring to the nitrogen atom in formula Xa; and D is a group of the formula

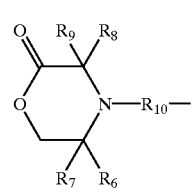
(XIa)

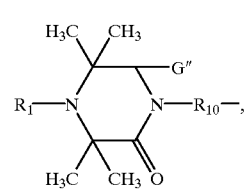
(XIc)

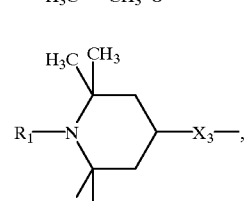
(XId)

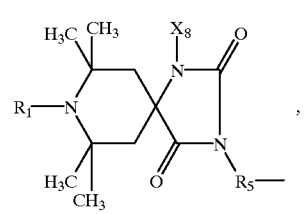
(XIe)

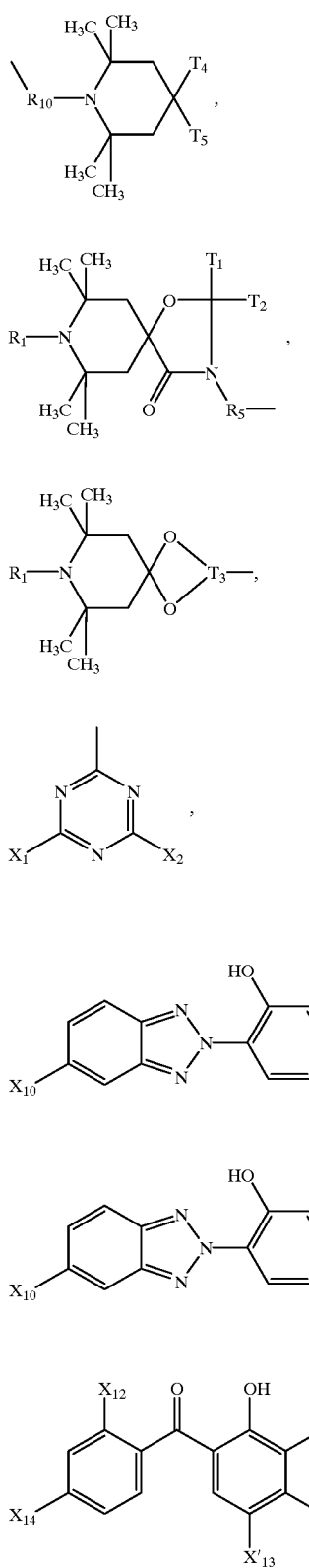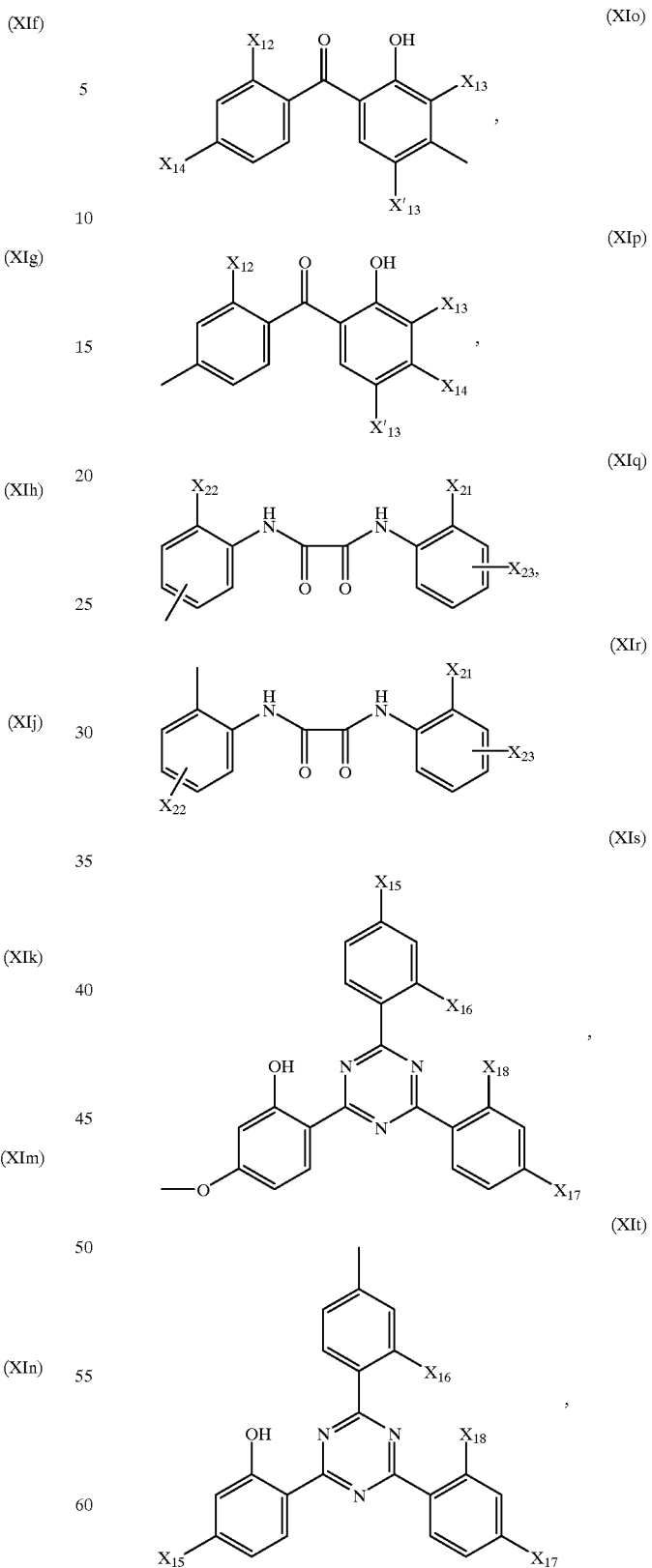

-continued

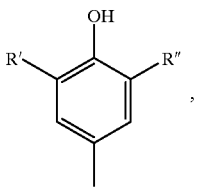
(XIu)

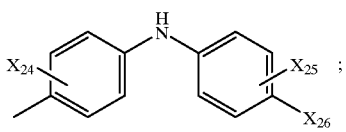
(XIv)

wherein

G" is hydrogen or =O;

R' is $C_1$–$C_{18}$alkyl or cyclohexyl, especially methyl or tert.-butyl;

R" is tert. $C_4$–$C_{18}$alkyl or cyclohexyl, especially tert.-butyl;

$T_1$, and $T_2$, independently, are H; $C_1$–$C_{18}$alkyl; phenyl-$C_1$–$C_4$alkyl; or naphthyl or phenyl which is unsubstituted or substituted by halogen or $C_1$–$C_4$alkyl; or $T_1$ and $T_2$ together with the linking carbon atom form a $C_5$–$C_{12}$cycloalkane ring;

$T_3$ is $C_2$–$C_8$alkanetriyl, especially

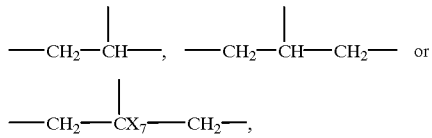

where $X_7$ is $C_1$–$C_5$alkyl;

$T_4$ is H, $C_1$–$C_{18}$alkoxy, $C_3$–$C_8$alkenyloxy or benzyloxy and $T_5$ is as defined for $T_4$, or $T_4$ and $T_5$ together are —O—$C_2$–$C_8$alkylene-O—, and if $T_4$ is H, $T_5$ additionally embraces —OH and —NR'$_{10}$—CO—R'$_{11}$, where R'$_{11}$ is $C_1$–$C_{18}$alkyl, $C_2$–$C_4$alkenyl or phenyl;

$X_1$ is a group of formula (XId); and $X_2$ is as defined for $X_1$ or is $C_1$–$C_{18}$alkoxy or —N(R'$_{14}$)$_2$;

$X_3$ is —NR'$_{10}$—, —NX$_6$—, —O—, or a radical of the formula —O—CO—$X_5$—CO—O—$X_6$, where $X_5$ is $C_1$–$C_{12}$alkanetriyl and $X_6$ is a radical of the formula

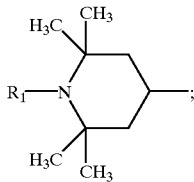

$X_8$ is H, $C_1$–$C_{18}$alkyl, $C_7$–$C_{11}$phenylalkyl, $C_2$–$C_6$alkoxyalkyl or $C_5$–$C_{12}$cycloalkyl;

$X_{10}$ is H, Cl, $C_1$–$C_4$alkyl, $C_1$–$C_4$alkoxy;

$X_{11}$ is $C_1$–$C_{12}$alkyl;

$X'_{11}$ is H or $C_1$–$C_{12}$alkyl;

$X_{12}$ is H or OH;

$X_{13}$ is H, Cl, OH or $C_1$–$C_{18}$alkoxy;

$X'_{13}$ is H, Cl or $C_1$–$C_4$alkyl;

$X_{14}$ is H, Cl, OH or $C_1$–$C_{18}$alkoxy;

$X_{15}$ and $X_{17}$, independently, are H, OH, Cl, CN, phenyl, $C_1$–$C_6$alkyl, $C_1$–$C_{18}$alkoxy, $C_4$–$C_{22}$alkoxy interrupted by O and/or substituted by OH, or are $C_2$–$C_{20}$alkanoylamino or $C_7$–$C_{14}$phenylalkoxy;

$X_{16}$ and $X_{18}$, independently, are H, OH, Cl, $C_1$–$C_6$alkyl or $C_1$–$C_6$alkoxy;

$X_{21}$, $X_{22}$ and $X_{23}$, independently, are H, $C_1$–$C_{18}$alkyl or $C_1$–$C_{18}$alkoxy;

$X_{24}$ and $X_{25}$, independently, are H or $C_1$–$C_8$alkyl; and $X_{26}$ is H, $C_1$–$C_8$alkyl, phenyl, $C_7$–$C_{11}$phenylalkyl, cyclohexyl or —N(R'$_{14}$)$_2$;

and if $X_{25}$ is in ortho-position to $X_{26}$, $X_{25}$ can form, together with $X_{26}$ and the carbon atoms they are attached to, a phenyl ring.

The compounds of the invention may be further reacted in order to obtain other structures than those mentioned above. For example, compounds wherein Hal stands for a halogen atom are often reacted with suitable agents to obtain compounds wherein the halogen atom is replaced by a linking group or the substituent Y—R'$_{14}$, preferably before they are used as stabilizers.

More preferred is a compound of formula A, B, C or D, wherein $R_2$, $R_4$, $R_5'$, $R_6$, $R_7$, $R_8$ and $R_9$ are, independently of one another, $C_1$–$C_{18}$alkyl, $C_3$–$C_8$alkenyl, $C_5$–$C_{12}$cycloalkenyl, or $C_5$–$C_{12}$cycloalkyl; or $R_2$ and $R_3$, $R_4$ and $R_5'$, $R_6$ and $R_7$, $R_8$ and $R_9$ form, together with the carbon atom they are attached to, $C_5$–$C_{12}$cycloalkylene;

$R_3$ is $C_1$–$C_8$hydroxyalkyl, $C_1$–$C_{18}$alkyl or $C_5$–$C_{12}$cycloalkyl;

$R_5$ is $C_1$–$C_4$alkylene; $C_1$–$C_4$alkylene-CO—; and in formula A also may be a direct bond;

$R_{10}$ is $C_2$–$C_8$alkylene; $C_1$–$C_8$alkylene-CO—;

$R'_{10}$ is hydrogen or $C_1$–$C_8$alkyl or $C_5$–$C_{12}$cycloalkyl;

W is —O— or —NR'$_{14}$— and, if m is not 1, W can also be a direct bond;

X' is as defined for X below;

Y is —O— or —NR'$_{14}$—;

Z and Z', independently, are a direct bond or have a meaning given for Y;

when m is 1, X is $C_1$–$C_{18}$alkyl; $C_1$–$C_{18}$alkyl substituted by $C_1$–$C_{18}$alkoxy, —OH, —OCO—R$_{11}$, —COR$_{11}$, —COOR$_{13}$, CN, $C_5$–$C_{12}$cycloalkoxy, allyloxy, halogen, —CON(R'$_{14}$)$_2$, phenoxy; or X is $C_3$–$C_{30}$alkyl which is interrupted by —O— and can be substiituted by OH; $C_5$–$C_{12}$cycloalkyl; $C_3$–$C_6$alkenyl; glycidyl; $C_7$–$C_{15}$phenylalkyl; $C_7$–$C_{15}$phenylalkyl, which is substituted on the phenyl ring by a radical selected from $C_1$–$C_4$alkyl and $C_1$–$C_4$alkoxy; or is a group of formulae IIIa–IIId —CO—R$_{11}$ (IIIa)

—R$_{12}$—COO—R$_{13}$ (IIIb)

—CO—NH—R$_{14}$ (IIIc)

—CO—R$_{18}$—COO—R'$_{17}$ (IIId);

when m is 2, X is $C_2$–$C_{18}$alkylene; $C_4$–$C_{12}$alkylene interrupted by oxygen, phenylene, $C_5$–$C_{12}$cycloalkylene, S and/or substituted by $C_1$–$C_{18}$alkoxy, —OCO—$R_{11}$, —COR$_{11}$, —COOR'$_{17}$, CN, $C_5$–$C_{12}$cycloalkoxy, allyloxy, halogen, —CON(R'$_{14}$)$_2$, phenoxy and/or $C_1$–$C_{18}$alkyl-, $C_1$–$C_{18}$alkoxy- or halo-substituted phenoxy; or X is $C_5$–$C_{12}$cycloalkylene; phenylene; $C_5$–$C_{12}$cycloalkylene-$C_1$–$C_4$alkylene; phenylene-$C_1$–$C_4$alkylene; $C_2$–$C_8$alkylene interrupted by $C_5$–$C_{12}$cycloalkylene and/or phenylene; $C_5$–$C_{12}$cycloalkylene-E-$C_5$–$C_{12}$cycloalkylene; -phenylene-E-phenylene-, wherein E is $C_1$–$C_4$alkylene, —O—, —S—, —SO$_2$—, —CO—; or X is carbonyl or $C_1$–$C_7$alkylene-carbonyl or a group of formulae IVa–IVd;

—CO—$R_{18}$—CO— (IVa)

—COO—$R_{19}$—OCO— (IVb)

—CONH—$R_{20}$—NHCO— (IVc)

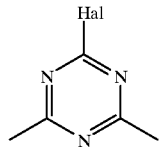
(IVd)

and if the linking group Z or W is a direct bond, X also may be $C_1$alkylene or Y;

when m is 3, X is $C_3$–$C_{18}$alkanetriyl; P; PO; $C_4$–$C_{18}$triacyl; 1,3,5-triazine-2,4,6-triyl; or a group of formula (VIIb);

when m is 4, X is $C_5$–$C_{18}$alkanetetryl; $C_6$–$C_{18}$tetraacyl; or a group of the formula $Z_1$—Y—$R_{20}$—Y—$Z_2$ (VIIIb);

when m is 6, X is $C_9$–$C_{18}$hexaacyl; or a hexavalent residue of the formula IXa' or IXb $Z_1$—NR'$_{10}$—$R_{20}$—N($Z_2$)—$R_{20}$—NR'$_{10}$—$Z_3$ (IXa');

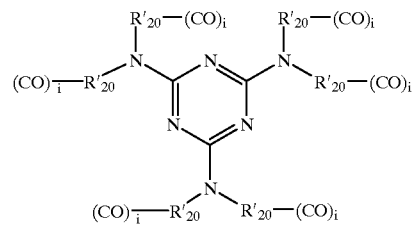
(IXb)

when m is 8, X is $C_9$–$C_{18}$octoacyl; or an octovalent residue of the formula Xa' or Xb'

$Z_1$—NR'$_{10}$—$R_{20}$—N($Z_2$)—$R_{20}$—N($Z_3$)—$R_{20}$—NR'$_{10}$—$Z_4$ (Xa')

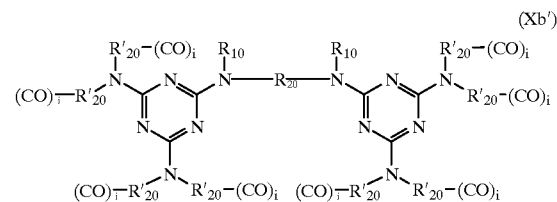
(Xb')

i is 0 or 1;

$R_{11}$ is hydrogen; $C_1$–$C_{18}$alkyl; $C_1$–$C_{18}$alkyl substituted by $C_1$–$C_{18}$alkoxy, —OCO—$R_{111}$, —COR$_{111}$, CN, $C_5$–$C_{12}$cycloalkoxy, allyloxy, halogen, —COOH, —CON(R'$_{14}$)$_2$, phenoxy; $C_5$–$C_{12}$cycloalkyl; $C_5$–$C_{12}$cycloalkyl, which is substituted by 1, 2 or 3 $C_1$–$C_4$alkyl; $C_2$–$C_{17}$alkenyl; phenyl; which is substituted by 1, 2 or 3 radicals selected from $C_1$–$C_4$alkyl, $C_1$–$C_4$alkoxy and hydroxy; $C_7$–$C_{15}$phenylalkyl; $C_7$–$C_{15}$phenylalkyl, which is substituted on the phenyl ring by 1, 2 or 3 radicals selected from $C_1$–$C_4$alkyl, $C_1$–$C_4$alkoxy and hydroxy; or $C_8$–$C_{12}$phenylalkenyl;

R'$_{11}$ is phenyl; phenyl which is substituted by 1, 2 or 3 radicals selected from $C_1$–$C_4$alkyl, $C_1$–$C_4$alkoxy and hydroxy; naphthyl; $C_7$–$C_{15}$phenylalkyl; $C_1$–$C_{17}$alkyl; $C_5$–$C_{12}$cycloalkyl;

$R_{111}$ is $C_1$–$C_{12}$alkyl or phenyl or $C_7$–$C_{15}$alkylphenyl;

$R_{12}$ is a direct bond, $C_1$–$C_{18}$alkylene or carbonyl;

$R_{13}$ is $C_1$–$C_{18}$alkyl; $C_3$–$C_{18}$alkenyl; $C_5$–$C_{12}$cycloalkyl; $C_5$–$C_{12}$cycloalkyl, which is substituted by 1, 2 or 3 $C_1$–$C_4$alkyl;

$R_{14}$ is $C_1$–$C_{18}$alkyl; $C_5$–$C_{12}$cycloalkyl; $C_5$–$C_{12}$cycloalkyl, which is substituted by 1, 2 or 1, 2 or 3 $C_1$–$C_4$alkyl; $C_3$–$C_{17}$alkenyl; $C_2$–$C_8$hydroxyalkyl; $C_7$–$C_{15}$phenylalkyl;

R'$_{14}$ is hydrogen or has one of the meanings given for $R_{14}$;

R'$_{17}$ embraces the meanings given for $R_{13}$ above or is hydrogen or one equivalent of a metal of main group I or II of the periodic system;

$R_{18}$ is a direct bond; $C_1$–$C_{22}$alkylene; $C_2$–$C_{22}$alkylene interrupted by oxygen, phenylene, $C_5$–$C_{12}$cycloalkylene, S, NR'$_{14}$ and/or substituted by OH, $C_1$–$C_{18}$alkoxy, —N(R'$_{14}$)$_2$, —OCO—$R_{11}$, —COR$_{11}$, —COOR$_{13}$, CN, —(O)$_i$—P(=O)$_i$(OR$_{111}$)$_2$, $C_5$–$C_{12}$cycloalkoxy, allyloxy, halogen, —COOH, —CON(R'$_{14}$)$_2$, phenoxy and/or $C_1$–$C_{18}$alkyl-, $C_1$–$C_{18}$alkoxy- or halo-substituted phenoxy; $C_2$–$C_8$alkenylene; $C_2$–$C_8$alkenylene substituted by $R_{21}$; $C_2$–$C_8$alkylene substituted by $R_{21}$; cyclohexylene; cyclohexenylene or phenylene; or $R_{19}$ is $C_2$–$C_{12}$alkylene; $C_4$–$C_{12}$alkylene interrupted by oxygen, phenylene and/or $C_5$–$C_{12}$cycloalkylene; $C_5$–$C_{12}$cycloalkylene; bis($C_5$–$C_{12}$cycloalkylene)-$C_1$–$C_4$alkylene;

$R_{20}$ is $C_2$–$C_{12}$alkylene; $C_5$–$C_{12}$cycloalkylene; or phenylene;

R'$_{20}$ is $C_2$–$C_{12}$alkylene; $C_5$–$C_{12}$cycloalkylene; phenylene; and if i is 1, R'$_{20}$ additionally embraces methylene;

$R_{21}$ is phenyl; phenyl which is substituted by 1, 2 or 3 radicals selected from $C_1$–$C_4$alkyl, $C_1$–$C_4$alkoxy, di($C_1$–$C_4$alkyl)amino, nitro, hydroxy; or is naphthyl; or naphthyl which is substituted by $C_1$–$C_4$alkyl, $C_1$–$C_4$alkoxy, di($C_1$–$C_4$alkyl)amino, nitro; or $R_{21}$ is thienyl; phenoxyphenyl; thiophen-2-yl; phenylthiophenyl; benzo[b]thiophen-2-yl; benzofuran-2-yl; 9H-fluorenyl; biphenylyl; 10-($C_1$–$C_8$alkyl)-10H-phenothiazinyl;

D is a group of the formula XIa, XIc, XId, XIf, XIj, XIk, XIm, XIn, XIo, XIp, XIs, XIt or XIu.

Of special interest is a compound of the formula I, II or III

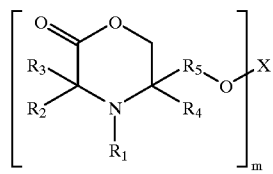 (I)

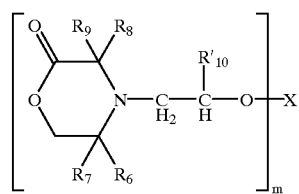 (II)

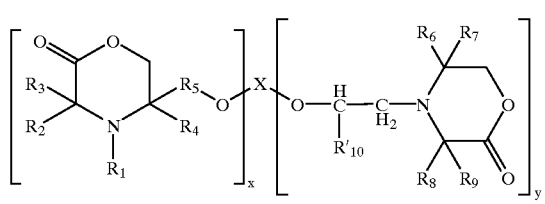 (III)

where m is the valency of X and is an integer from the range 1≠6;

x and y are each integers from the range 1–5 obeying the condition x+y=m;

$R_1$ is hydrogen; $C_1$–$C_{18}$alkyl; oxyl; OH; $CH_2CN$; $C_1$–$C_{18}$alkoxy; $C_5$–$C_{12}$cycloalkoxy; $C_3$–$C_8$alkenyl; $C_3$–$C_8$alkynyl; $C_7$–$C_{12}$phenylalkyl; $C_7$–$C_{15}$phenylalkyl, which is substituted on the phenyl ring by 1, 2 or 3 radicals selected from $C_1$–$C_4$alkyl and $C_1$–$C_4$alkoxy; $C_7$–$C_{15}$phenylalkoxy; $C_7$–$C_{15}$phenylalkoxy, which is substituted on the phenyl ring by 1, 2 or 3 radicals selected from $C_1$–$C_4$alkyl and $C_1$–$C_4$alkoxy; or $R_1$ is $C_1$–$C_8$alkanoyl; $C_3$–$C_5$alkenoyl; $C_1$–$C_{18}$alkanoyloxy; glycidyl; or a group —$CH_2CH(OH)$—G, in which G is hydrogen, methyl or phenyl;

$R_2$, $R_3$, $R_4$, $R_6$, $R_7$, $R_8$ and $R_9$ are, independently of one another, $C_1$–$C_{18}$alkyl or $C_5$–$C_{12}$cycloalkyl;

or $R_2$ and $R_3$, $R_6$ and $R_7$, $R_8$ and $R_9$ form, together with the carbon atom they are attached to, $C_5$–$C_{12}$cycloalkylene;

$R_5$ is $C_1$–$C_4$alkylene;

$R'_{10}$ is hydrogen or $C_1$–$C_4$alkyl;

when m is 1, X is $C_1$–$C_{18}$alkyl; $C_5$–$C_{12}$cycloalkyl; $C_3$–$C_6$alkenyl; glycidyl; $C_7$–$C_{15}C_{15}$phenylalkyl, which is substituted on the phenyl ring by 1, 2 or 3 radicals selected from $C_1$–$C_4$alkyl and $C_1$–$C_4$alkoxy; or is a group of formulae IIIa–IIId —CO—$R_{11}$ (IIIa)

—$R_{12}$—COO—$R_{13}$ (IIIb)

—CO—NH—$R_{14}$ (IIIc)

—CO—$R_{15}$—COO—$R'_{17}$ (IIId)

wherein $R_{11}$ is hydrogen; $C_1$–$C_{17}$alkyl; $C_5$–$C_{12}$cycloalkyl; $C_5$–$C_{12}$cycloalkyl, which is substituted by 1, 2 or 3 $C_1$–$C_4$alkyl; $C_2$–$C_{17}$alkenyl; phenyl; phenyl which is substituted by 1, 2 or 3 radicals selected from $C_1$–$C_4$alkyl, $C_1$–$C_4$alkoxy and hydroxy; $C_7$–$C_{15}$phenylalkyl; $C_7$–$C_{15}$phenylalkyl, which is substituted on the phenyl ring by 1, 2 or 3 radicals selected from $C_1$–$C_4$alkyl, $C_1$–$C_4$alkoxy and hydroxy; or $C_8$–$C_{12}$phenylalkenyl;

$R_{12}$ is a direct bond, $C_1$–$C_{18}$alkylene or carbonyl;

$R_{13}$ is $C_1$–$C_{18}$alkyl; $C_3$–$C_{18}$alkenyl; $C_5$–$C_{12}$cycloalkyl; $C_5$–$C_{12}$cycloalkyl, which is substituted by 1, 2 or 3 $C_1$–$C_4$alkyl;

$R_{14}$ is $C_1$–$C_{18}$alkyl; $C_5$–$C_{12}$cycloalkyl; $C_5$–$C_{12}$cycloalkyl, which is substituted by 1, 2 or 3 $C_1$–$C_4$alkyl; $C_2$–$C_{17}$alkenyl; $C_7$–$C_{15}$phenylalkyl; $C_7$–$C_{15}$phenylalkyl, which is substituted on the phenyl ring by 1, 2 or 3 radicals selected from $C_1$–$C_4$alkyl, $C_1$–$C_4$alkoxy;

$R_{15}$ is $C_1$–$C_4$alkylene; $C_2$–$C_4$oxaalkylene; $C_5$–$C_{12}$cycloalkylene; $C_5$–$C_{12}$cycloalkenylene; phenylene; or a group of the formulae —$CH_2$—$CH(R_{16})$— or —$CH$=$C(R_{17})$—;

$R_{16}$ is $C_1$–$C_{18}$alkyl or $C_3$–$C_8$alkenyl;

$R_{17}$ is hydrogen or $C_1$–$C_4$alkyl;

$R'_{17}$ embraces the meanings given for $R_{13}$ above or is hydrogen or one equivalent of a metal of main group I or II of the periodic system;

when m is 2, X is $C_2$–$C_{12}$alkylene; $C_4$–$C_{12}$alkylene interrupted by oxygen, phenylene and/or $C_5$–$C_{12}$cycloalkylene; $C_5$–$C_{12}$cycloalkylene; bis($C_5$–$C_{12}$cycloalkylene)-$C_1$–$C_4$alkylene; or is a group of formulae IVa–IVf —CO—$R_{18}$—CO— (IVa)

—COO—$R_{19}$—OCO— (IVb)

—CONH—$R_{20}$—NHCO— (IVc)

—$C_tH_{2t}$—CO— (IVd)

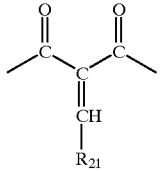 (IVe)

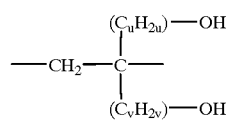 (IVf)

wherein t is zero or an integer from 1 to 7;

u and v, independently of one another, are integers from the range 1–4;

$R_{18}$ is a direct bond; $C_1$–$C_{22}$alkylene; $C_2$–$C_8$alkenylene; cyclohexylene; cyclohexenylene or phenylene;

$R_{19}$ is $C_2$–$C_{12}$alkylene; $C_4$–$C_{12}$alkylene interrupted by oxygen, phenylene and/or $C_5$–$C_{12}$cycloalkylene; $C_5$–$C_{12}$cycloalkylene; bis($C_5$–$C_{12}$cycloalkylene)-$C_1$–$C_4$alkylene;

$R_{20}$ is $C_2$–$C_{12}$alkylene; $C_5$–$C_{12}$cycloalkylene; or phenylene;

$R_{21}$ is phenyl; phenyl which is substituted by 1, 2 or 3 radicals selected from $C_1$–$C_4$alkyl, $C_1$–$C_4$alkoxy, di($C_1$–$C_4$alkyl)amino, nitro, hydroxy; or is naphthyl; or naphthyl which is substituted by $C_1$–$C_4$alkyl, $C_1$–$C_4$alkoxy, di($C_1$–$C_4$alkyl)amino, nitro; or $R_{21}$ is thienyl; indolyl; phenoxyphenyl; phenylthiophenyl; benzo[b]thiophen-2-yl; benzofuran-2-yl; 9H-fluorenyl; biphenyl; 10-($C_1$–$C_8$alkyl)-10H-phenothiazinyl; or is phenyl which is substituted by 1 or 2 radicals of the formulae

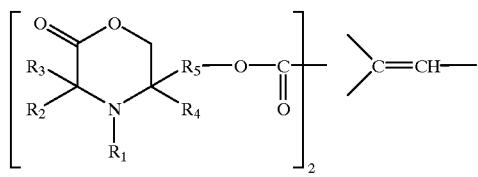

(V)

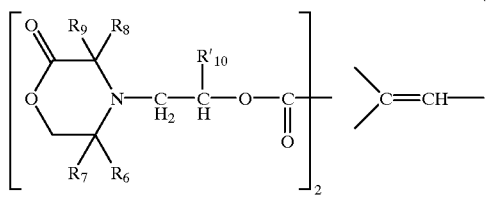

(VI)

when m is 3, X is aliphatic $C_4$–$C_{18}$triacyl, aromatic $C_9$–$C_{18}$triacyl or a group of the formula VII

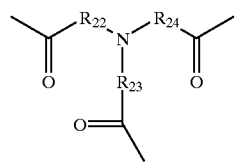

(VII)

wherein $R_{22}$, $R_{23}$ and $R_{24}$, independently of each other, are $C_1$–$C_7$alkylene;

when m is 4, X is aliphatic $C_6$–$C_{18}$tetraacyl, aromatic $C_{10}$–$C_{18}$tetraacyl or a group of the formula VIII

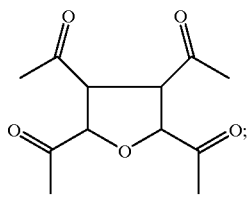

(VIII)

when m is 5, X is aliphatic $C_7$–$C_{18}$pentaacyl or aromatic $C_{10}$–$C_{18}$pentaacyl;

when m is 6, X is aliphatic $C_9$–$C_{18}$hexaacyl or aromatic $C_{12}$–$C_{18}$hexaacyl.

The compounds of the invention can be pure or mixtures of compounds, including pure diastereomers or enantiomers, and mixtures of diastereomers or enantiomers. Preferred mixtures are those of compounds of formula I or II wherein m is 2 and X corresponds to formula IVa with $R_{18}$ being at least 2 different groups —(CH$_2$)$_n$— where n is an integer from the range 1–18. Of special importance are mixtures of mono- and diesters of the invention, as for example a mixture of a compound of formula I or II wherein X is a residue of formula IIId with one wherein X is a residue of formula IVa (mono- and diester).

Residues denoted with the same symbol within the same formula can have identical or different meanings.

Alkyl groups, such as $R_1$, $R_2$, $R_3$, $R_4$, $R_6$, $R_7$, $R_8$, $R_9$, $R'_{10}$, $R_{11}$, $R_{13}$, $R_{14}$, $R_{16}$, $R_{17}$, $R'_{17}$ and X as alkyl are, within the definitions given, for example methyl, ethyl, propyl such as n- or isopropyl, butyl such as n-, iso-, sec- and tert-butyl, pentyl, hexyl, heptyl, octyl, nonyl, decyl, undecyl, dodecyl, tridecyl, tetradecyl, pentadecyl, hexadecyl, heptadecyl or octadecyl.

Alkylene groups, such as $R_5$, $R_{10}$, $R_{15}$, $R_{12}$, $R_{18}$, $R_{19}$, $R_{20}$, $R_{22}$, $R_{23}$, $R_{24}$, X as alkylene are, within the definitions given, for example methylene, 1,2-ethylene, 1,1-ethylene, 1,3-propylene, 1,2-propylene, 1,1-propylene, 2,2-propylene, 1,4-butylene, 1,3-butylene, 1,2-butylene, 1,1-butylene, 2,2-butylene, 2,3-butylene, or —$C_5H_{10}$—, —$C_6H_{12}$—, $C_7H_{14}$, —$C_8H_{16}$—, —$C_9H_{18}$—, —$C_{10}H_{20}$—, —$C_{11}H_{22}$—, —$C_{12}H_{24}$—, —$C_{13}H_{26}$—, —$C_{14}H_{28}$—, —$C_{15}H_{30}$—, —$C_{16}H_{32}$—, —$C_{17}H_{34}$—, —$C_{18}H_{36}$—.

—$R_5$, $R_{22}$, $R_{23}$, $R_{24}$ are especially preferred as methylene.

Cycloalkyl groups, such as $R_1$, $R_{11}$, $R_{13}$, $R_{14}$ or X as $C_5$–$C_{12}$-Cycloalkyl are, for example, cyclopentyl, cyclohexyl, cycloheptyl, cyclooctyl, cyclononyl, cyclodecyl, cycloundecyl or cyclododecyl. $C_5$–$C_{12}$-Cycloalkenyl includes cyclopentenyl, cyclohexenyl, cycloheptenyl, cyclooctenyl, cyclononenyl, cyclodecenyl, cycloundecenyl, cyclododecenyl.

$C_1$–$C_4$alkyl substituted cycloalkyl (containing mainly 1–3, e.g. 1 or 2 alkyl groups) include inter alia 2- or 4-methylcyclohexyl, dimethylcyclohexyl, trimethylcyclohexyl, t-butylcyclohexyl.

Phenylalkyl or phenylalkoxy are alkyl or alkoxy each of which is substituted by phenyl. $R_1$, $R_{11}$, $R_{13}$, $R_{14}$ or X as $C_7$–$C_{15}$phenylalkyl or $C_7$–$C_{15}$phenylalkoxy are, within the definitions given, for example benzyl, benzyloxy, α-methylbenzyl, α-methylbenzyloxy, cumyl, cumyloxy.

$R_{18}$ as $C_2$–$C_{40}$oxaalkylene is, for example, —CH$_2$CH$_2$—O—CH$_2$CH$_2$—. Likewise, X as $C_4$–$C_{12}$alkylene interrupted by oxygen includes —CH$_2$CH$_2$—O—CH$_2$CH$_2$—, —CH$_2$CH$_2$—(O—CH$_2$CH$_2$)$_2$—, —CH$_2$CH$_2$—(O—CH$_2$CH$_2$)$_3$—, —CH$_2$CH$_2$—(O—CH$_2$CH$_2$)$_4$—, —CH$_2$CH$_2$—(O—CH$_2$CH$_2$)$_5$—, or —$C_3H_6$—(O—$C_3H_6$)$_i$—i being 1, 2 or 3.

X as a divalent interrupted residue further includes, for example, —CH$_2$-phenylene-CH$_2$—, $C_1$–$C_4$alkylene-O-1,2-cyclohexylene-O—$C_1$-$C_4$alkylene, bis($C_5$–$C_{12}$cycloalkylene)-$C_1$–$C_4$alkylene such as

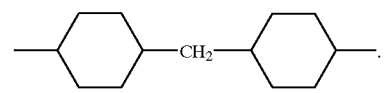

$R_1$ as alkanoyl or alkenoyl includes, for example, formyl, acetyl, propionyl, acryl, methacryl, butanoyl (butyryl), pentanoyl (valeryl), hexanoyl (caproyl); preferred are acetyl, propionyl, acryl, methacryl.

$R_1$ is preferably hydrogen; $C_1$–$C_8$alkyl; oxyl; OH; $CH_2CN$; $C_1$–$C_{18}$alkoxy; $C_5$–$C_{12}$cycloalkoxy; $C_3$–$C_6$alkenyl; $C_7$–$C_{15}$phenylalkyl; $C_7$–$C_{15}$phenylalkyl, which is substituted on the phenyl ring by 1, 2 or 3 radicals selected from $C_1$–$C_4$alkyl and $C_1$–$C_4$alkoxy; or $R_1$ is $C_1$–$C_8$alkanoyl or $C_3$–$C_5$alkenoyl;

$R_1$ preferably being H, $C_1$–$C_4$alkyl, $C_3$–$C_4$alkenyl, $C_3$–$C_4$alkynyl, allyl, benzyl, cyclohexyloxy, $C_1$–$C_{12}$alkoxy, acetyl or acryloyl;

Among the dimeric compounds of formulae I or II (m is 2), compounds are most preferred wherein X is a group of the formula (IVa), the compounds can be pure or mixtures containing at least two different compounds where $R_{18}$ is —$(CH_2)_n$—, where n is an integer from 1 to 18.

Most preferred is a compound of formula A, B, C or D, wherein m is the valency of X and is an integer from the range 1–4 or is 6 or 8;

x is 1 or 2 and y is 1;

$R_1$ is hydrogen; $C_1$–$C_{18}$alkyl; oxyl; OH; $C_1$–$C_{18}$alkoxy; $C_5$–$C_{12}$cycloalkoxy; $C_3$–$C_8$alkenyl; $C_3$–$C_8$alkynyl; $C_3$–$C_8$alkenyloxy; $C_7$–$C_{12}$phenylalkyl; $C_2$–$C_8$alkanoyl; $C_3$–$C_5$alkenoyl; or glycidyl;

$R_2$, $R_4$, $R_5'$, $R_6$, $R_7$, $R_8$ and $R_9$ are, independently of one another, $C_1$–$C_{18}$alkyl, $C_3$–$C_{18}$alkyl, $C_3$–$C_8$alkenyl, or $C_5$–$C_{12}$Cycloalkyl;

$R_3$ is $C_1$–$C_8$hydroxyalkyl, $C_1$–$C_{18}$alkyl or $C_5$–$C_{12}$cycloalkyl;

$R_5$ is $C_1$–$C_4$alkylene; $C_1$–$C_4$alkylene-CO—; and in formula A also may be a direct bond;

$R_{10}$ is $C_2$–$C_8$alkylene; $C_1$–$C_8$alkylene-CO—;

W is —O— or —$NR'_{14}$— and, if m is not 1, W can also be a direct bond;

X' is as defined for X below;

Y is —O— or —$NR'_{14}$—;

Z and Z', independently, are a direct bond or have a meaning given for Y;

when m is 1, X is $C_1$–$C_{18}$alkyl; $C_1$–$C_{18}$alkyl substituted by $C_1$–$C_{18}$alkoxy, —OH, —OCO—$R_{11}$, CN, $C_5$–$C_{12}$cycloalkoxy, allyloxy, halogen, phenoxy; or X is $C_3$–$C_{30}$alkyl which is interrupted by —O— and can be substiituted by OH; $C_5$–$C_{12}$cycloalkyl; $C_3$–$C_6$alkenyl; glycidyl; $C_7$–$C_{15}$phenylalkyl; or is a group of formula IIIa or IIId —CO—$R_{11}$ (IIIa)

—CO—$R_{18}$—COO—$R'_{17}$ (IIId);

$R_{11}$ is $C_1$–$C_{18}$alkyl; $C_1$–$C_{18}$alkyl substituted by $C_1$–$C_{18}$alkoxy, —OCO—$R_{111}$, —$COR_{111}$, CN, $C_5$–$C_{12}$cycloalkoxy, —COOH, $C_5$–$C_{12}$cycloalkyl; $C_5$–$C_{12}$cycloalkyl, which is substituted by 1, 2 or 3 $C_1$–$C_4$alkyl; $C_2$–$C_8$alkenyl; phenyl; $C_7$–$C_{15}$phenylalkyl;

$R'_{14}$ is hydrogen or $C_1$–$C_{18}$alkyl; cyclohexyl; $C_2$–$C_8$hydroxyalkyl; $C_7$–$C_{15}$phenylalkyl;

$R'_{17}$ is hydrogen or $C_1$–$C_{12}$alkyl or an equivalent of a sodium, potassium, magnesium or calcium ion;

when m is 2, X is $C_2$–$C_{18}$alkylene; $C_4$–$C_{12}$alkylene interrupted by oxygen, phenylene, $C_5$–$C_{12}$cycloalkylene, S and/or substituted by $C_1$–$C_{18}$alkoxy, —OH, —OCO—$R_{11}$, CN, $C_5$–$C_{12}$cycloalkoxy, allyloxy, halogen, phenoxy; or X is $C_5$–$C_{12}$cycloalkylene; phenylene; $C_5$–$C_{12}$cycloalkylene-$C_1$–$C_4$alkylene; phenylene-$C_1$–$C_4$alkylene; $C_2$–$C_8$alkylene interrupted by $C_5$–$C_{12}$cycloalkylene and/or phenylene; $C_5$–$C_{12}$cycloalkylene-E-$C_5$–$C_{12}$cycloalkylene; -phenylene-E-phenylene-, wherein E is $C_1$–$C_4$alkylene, —O—, —S—, —$SO_2$—, —CO—; or X is carbonyl or $C_1$–$C_7$alkylene-carbonyl or a group of formula —CO—$R_{18}$—CO— (IVa);

wherein $R_{18}$ is a direct bond; $C_1$–$C_{18}$alkylene; $C_4$–$C_{22}$alkylene interrupted by oxygen, phenylene, $C_5$–$C_{12}$cycloalkylene, S; $C_2$–$C_8$alkenylene; $C_2$–$C_8$alkenylene substituted by $R_{21}$; $C_2$–$C_8$alkylene substituted by $R_{21}$; cyclohexylene; or phenylene;

$R_{20}$ and $R'_{20}$, independently, are $C_2$–$C_{12}$alkylene or cyclohexylene; and if i is 1, $R'_{20}$ additionally embraces methylene;

$R_{21}$ is phenyl; phenyl which is substituted by 1, 2 or 3 radicals selected from $C_1$–$C_4$alkyl, $C_1$–$C_4$alkoxy, hydroxy; or is naphthyl; or naphthyl which is substituted by $C_1$–$C_4$alkyl, $C_1$–$C_4$alkoxy; or $R_{21}$ is thienyl; phenylthiophenyl; thiophen-2-yl; benzo[b]thiophen-2-yl; biphenylyl; 10-($C_1$–$C_8$alkyl)-10H-phenothiazinyl;

when m is 3, X is $C_3$–$C_{18}$alkanetriyl; P; PO; $C_4$–$C_{18}$triacyl; 1,3,5-triazine-2,4,6-triyl;

when m is 4, X is $C_5$–$C_{18}$alkanetetryl; $C_6$–$C_{18}$tetraacyl; or a group of the formula $Z_1$—Y—$R_{20}$—Y—$Z_2$ (VIIIb);

when m is 6, X is a hexavalent residue of the formula IXa' or IXb $Z_1$—$NR'_{10}$—$R_{20}$—$N(Z_2)$—$R_{20}$—$NR'_{10}$—$Z_3$ (IXa');

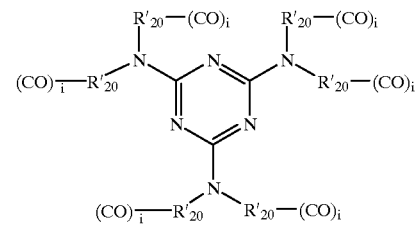

(IXb)

when m is 8, X is octovalent residue of the formula Xa' or Xb'

$Z_1$—$NR'_{10}$—$R_{20}$—$N(Z_2)$—$R_{20}$—$N(Z_3)$—$R_{20}$—$NR'_{10}$—$Z_4$ (Xa')

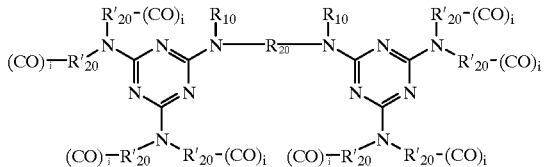

(Xb')

D is a group of the formula XIa, XIc, XId, XIj, XIk, XIm, XIn, XIo, XIp, XIs or XIu;

G" is hydrogen or =O;

R' is cyclohexyl, methyl or tert.-butyl;

R" is cyclohexyl or tert.-butyl;

$X_1$ is a group of formula (XId); and $X_2$ is as defined for $X_1$ or is $C_1-C_{18}$alkoxy or $-N(R'_{14})_2$;

$X_3$ is $-O-$;

$X_{10}$ is H, Cl, $C_1-C_4$alkyl, $C_1-C_4$alkoxy;

$X_{11}$ is $C_1-C_{12}$alkyl;

$X'_{11}$ is H or $C_1-C_{12}$alkyl;

$X_{12}$ is H or OH;

$X_{13}$ is H, Cl, OH or $C_1-C_8$alkoxy;

$X'_{13}$ is H, Cl or $C_1-C_4$alkyl;

$X_{14}$ is H, Cl, OH or $C_1-C_8$alkoxy;

$X_{15}$ and $X_{17}$, independently, are H, OH, Cl, phenyl, $C_1-C_6$alkyl, $C_1-C_{18}$alkoxy, $C_4-C_{22}$alkoxy interrupted by O and/or substituted by OH, or are $C_7-C_{14}$phenylalkoxy; or $C_2-C_{20}$alkanoylamino; and $X_{16}$ and $X_{18}$, independently, are H, OH, methyl or $C_1-C_6$alkoxy;

especially one, wherein x is 1 and y is 1;

$R_1$ is hydrogen; $C_1-C_6$alkyl; oxyl; OH; $C_1-C_{18}$alkoxy; cyclohexyloxy; allyl; allyloxy; $C_2-C_8$alkanoyl; or glycidyl;

$R_2$, $R_3$, $R_4$, $R_5'$, $R_6$, $R_7$, $R_8$ and $R_9$ are, independently of one another, $C_1-C_6$alkyl or cyclohexyl;

$R_5$ is $C_1-C_4$alkylene; and in formula A also may be a direct bond;

$R_{10}$ is $C_2-C_8$alkylene;

W is $-O-$;

when m is 1, X is $C_1-C_{18}$alkyl; $C_1-C_8$alkyl substituted by $C_1-C_8$alkoxy, $-OH$, $-OCO-R_{11}$, cyclohexyloxy; $C_7-C_{15}$phenylalkyl; or is a group of formula IIIa or IIId $-CO-R_{11}$ (IIIa)

$-CO-R_{18}-COO-R'_{17}$ (IIId);

when m is 2, X is $C_2-C_{18}$alkylene; $C_4-C_{12}$alkylene interrupted by oxygen; $C_5-C_{12}$cycloalkylene; phenylene; cyclohexylene-$C_1-C_4$alkylene; phenylene-$C_1-C_4$alkylene; $C_2-C_8$alkylene interrupted by cyclohexylene and/or phenylene; cyclohexylene-E-cyclohexylene; -phenylene-E-phenylene-, wherein E is $C_1-C_4$alkylene, $-O-$, $-S-$, $-SO_2-$, $-CO-$; or X is carbonyl or $C_1-C_7$alkylene-carbonyl or a group of formula $-CO-R_{18}-CO-$ (IVa);

when m is 3, X is $C_4-C_{18}$triacyl; 1,3,5-triazine-2,4,6-triyl;

when m is 4, X is $C_5-C_{18}$alkanetetryl; $C_6-C_{18}$tetraacyl; or a group of the formula $Z_1-Y-R_{20}-Y-Z_2$ (VIIIb);

when m is 6, X is a hexavalent residue of the formula IXa' or IXb $Z_1-NR'_{10}-R_{20}-N(Z_2)-R_{20}-NR'_{10}-Z_3$ (IXa');

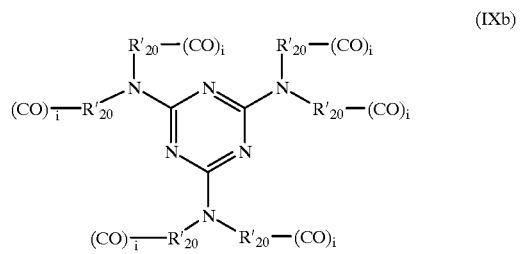

when m is 8, X is octovalent residue of the formula Xa' or Xb'

$Z_1-NR'_{10}-R_{20}-N(Z_2)-R_{20}-N(Z_3)-R_{20}-NR'_{10}-Z_4$ (Xa')

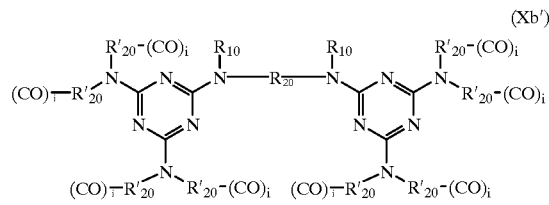

i is 0 or 1;

$R_{11}$ is $C_1-C_{18}$alkyl; $C_1-C_8$alkyl substituted by $C_1-C_8$alkoxy, $C_2-C_8$alkenyl; phenyl; $C_7-C_{15}$phenylalkyl;

$R'_{14}$ is hydrogen or $C_1-C_{18}$alkyl; cyclohexyl; $C_2-C_8$hydroxyalkyl; $C_7-C_{15}$phenylalkyl;

$R_{16}$ is $C_1-C_{18}$alkyl or $C_3-C_8$alkenyl;

$R'_{17}$ is hydrogen or $C_1-C_4$alkyl or an equivalent of a sodium, potassium, magnesium or calcium ion;

$R_{18}$ is a direct bond; $C_1-C_{18}$alkylene; $C_2-C_8$alkenylene; $C_2-C_8$alkenylene substituted by $R_{21}$; $C_2-C_8$alkylene substituted by $R_{21}$; cyclohexylene; or phenylene;

$R_{20}$ and $R'_{20}$, independently, are $C_2-C_{12}$alkylene or cyclohexylene; and if i is 1, $R'_{20}$ additionally embraces methylene;

$R_{21}$ is phenyl; thienyl; thiophen-2-yl;

D is a group of the formula XIa, XIc, XId, XIj, XIk, XIm, XIn, XIo, XIp, XIs or XIu;

G" is hydrogen;

R' is methyl or tert.-butyl;

R" is tert.-butyl;

$X_1$ is a group of formula (XId); and $X_2$ is as defined for $X_1$ or is $-N(R'_{14})_2$;

$X_3$ is $-O-$;

$X_{10}$ is H, Cl, methyl or methoxy;

$X_{11}$ and $X'_{11}$, independently, are $C_1-C_{12}$alkyl;

$X_{12}$ is H or OH;

$X_{13}$ is H or $C_1-C_8$alkoxy;

$X'_{13}$ is H or $C_1-C_4$alkyl;

$X_{14}$ is H or $C_1-C_8$alkoxy;

$X_{15}$, $X_{17}$, $X_{16}$ and $X_{18}$, independently, are H, phenyl or methyl.

Another important class of compounds embraces those of formula I or II, where $R_1$ is hydrogen, $C_1-C_8$alkyl, oxyl, OH, $-CH_2CN$, $C_1-C_{18}$alkoxy, $C_5-C_{12}$cycloalkoxy, $C_3-C_6$alkenyl, $C_7-C_9$phenylalkyl which is unsubstituted or mono-, dior tri-substituted on the phenyl by $C_1$–$C_4$alkyl or $C_1$–$C_4$alkoxy; or aliphatic $C_1$–$C_{18}$acyl;

$R_2$, $R_3$, $R_4$, $R_6$, $R_7$, $R_8$, $R_9$, which are similar or different, are $C_1$–$C_8$alkyl, $C_5$–$C_7$cycloalkyl.

$R_2$ and $R_3$, $R_6$ and $R_7$, $R_8$ and $R_9$ may, when taken together with the carbon atom to which they are attached, be $C_5$–$C_7$cycloalkylene;

$R_5$ is a linear or branched $C_1$–$C_4$alkylene;

$R'_{10}$ is hydrogen or $C_1$–$C_4$alkyl;

when m is 1, X is $C_1$–$C_{18}$alkyl, $C_5$–$C_{12}$cycloalkyl, $C_3$–$C_6$alkenyl, $C_7$–$C_9$phenylalkyl which is unsubstituted or mono-, di- or tri-substituted on the phenyl by $C_1$–$C_4$alkyl or $C_1$–$C_4$alkoxy; or X is also one of the groups of the formulae (IIIa)–(IIIc)

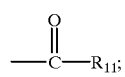
(IIIa)

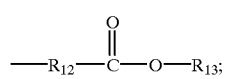
(IIIb)

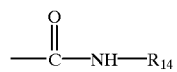
(IIIc)

in which $R_{11}$ is hydrogen, $C_1$–$C_{17}$alkyl, $C_5$–$C_{12}$cycloalkyl, which is unsubstituted or mono-, di- or tri-substituted by $C_1$–$C_4$alkyl; $C_2$–$C_{17}$alkenyl, phenyl which is unsubstituted or mono-, di- or tri-substituted by $C_1$–$C_4$alkyl, $C_1$–$C_4$alkoxy or OH groups; $C_7$–$C_9$phenylalkyl which is unsubstituted or mono-, di- or tri-substituted on the phenyl by $C_1$–$C_4$alkyl, $C_1$–$C_4$alkoxy or —OH groups;

$R_{12}$ is a direct bond, $C_1$–$C_7$alkylene, carbonyl or a group

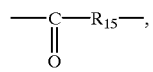

the group $R_{15}$ being bound to the group

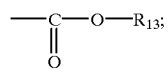

$R_{13}$ is $C_1$–$C_{18}$alkyl, $C_3$–$C_{18}$alkenyl, $C_5$–$C_{12}$cycloalkyl which is unsubstituted or mono-, di- or tri substituted by $C_1$–$C_4$alkyl;

$R_{14}$ is $C_1$–$C_{18}$alkyl, $C_5$–$C_{12}$cycloalkyl which is unsubstituted or mono-, di- or tri-substituted by $C_1$–$C_4$alkyl; or $C_7$–$C_9$phenylalkyl unsubstituted or mono-, di- or tri-substituted on the phenyl by $C_1$–$C_4$alkyl or $C_1$–$C_4$alkoxy;

$R_{15}$ is a linear $C_1$–$C_4$alkylene, a group

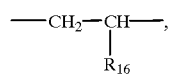

a group

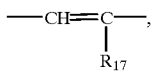

$C_2$–$C_4$oxaalkylene, $C_5$–$C_7$cycloalkyl-1,2-ene, $C_5$–$C_7$cycloalken-1,2-ylene or 1,2-phenylene;

$R_{16}$ is $C_1$–$C_{18}$alkyl or $C_3$–$C_8$alkenyl and $R_{17}$ is hydrogen or $C_1$–$C_4$alkyl;

when $R_{12}$ is a group

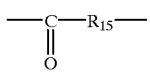

where $R_{15}$ is as defined above, $R_{13}$ can be also hydrogen, sodium or potassium;

X is also a glycidyl group;

when m is 2,

X is $C_2$–$C_{12}$alkylene, $C_4$–$C_{12}$alkylene interrupted by 1, 2 or 3 oxygen atoms, $C_4$–$C_{12}$alkenylene, $C_5$–$C_7$cycloalkylene, $C_5$–$C_7$cycloalkylene di($C_1$–$C_4$alkylene), $C_1$–$C_4$alkylene di($C_5$–$C_7$cycloalkylene), $C_2$–$C_4$alkylidene di($C_5$–$C_7$cycloalkylene), phenylene di($C_1$–$C_4$alkylene) or one of the groups of the formula (IVa)–(IVf);

(IVa)

(IVb)

(IVc)

(IVd)

(IVe)

(IVf)

in which $R_{18}$ is a direct bond, $C_1$–$C_{22}$alkylene, $C_2$–$C_8$alkenylene, cyclohexylene, cyclohexenylene or phenylene;

$R_{19}$ is $C_2$–$C_{12}$alkylene, $C_4$–$C_{12}$alkylene interrupted by 1, 2 or 3 oxygen atoms; $C_5$–$C_7$cycloalkylene, $C_5$–$C_7$cycloalkylene di($C_1$–$C_4$alkylene) or $C_1$–$C_4$alkylidene di($C_5$–$C_7$cycloalkylene), $C_2$–$C_4$alkylidene di($C_5$–$C_7$cycloalkylene), phenylene di($C_1$–$C_4$alkylene);

$R_{20}$ is $C_2$–$C_{12}$alkylene, $C_5$–$C_7$cycloalkylene, phenylene;

t is zero or an integer 1 to 7;

$R_{21}$ is phenyl which is unsubstituted or mono-, di- or tri-substituted by $C_1$–$C_4$alkyl, $C_1$–$C_4$alkoxy, —OH, di($C_1$–$C_4$alkyl)amino or nitro group or is mono-, or di-substituted by a group of the formula (V) or (VI)

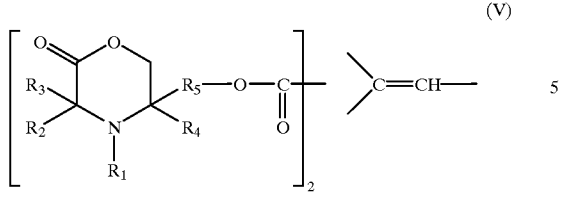

(V)

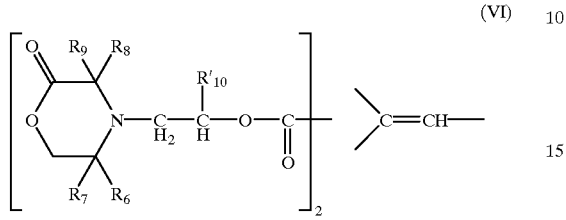

(VI)

in which $R_1, R_2, R_3, R_4, R_5, R_6, R_7, R_8, R_9$ and $R_{10}$ are as defined above;

or $R_{21}$ is naphthyl which is unsubstituted or monosubstituted by $C_1$–$C_4$alkyl, $C_1$–$C_4$alkoxy, di($C_1$–$C_4$alkyl) amino or nitro group, thienyl, phenoxyphenyl, phenylthiophenyl, benzo[b]thiophen-2-yl, benzofuran-2-yl, 9H-fluorenyl, biphenyl, 10($C_1$–$C_8$alkyl)-10H-phenothiazinyl;

u and v, which are similar or different, are integer 1 to 4;

when m is 3,

X is aliphatic $C_4$–$C_{18}$triacyl, aromatic $C_9$–$C_{18}$triacyl or a group of the formula (VII)

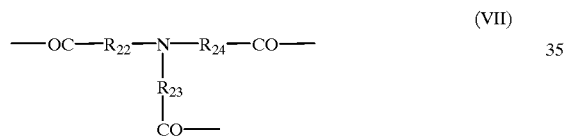

(VII)

where $R_{22}$, $R_{23}$ and $R_{24}$, which are similar or different are $C_1$–$C_7$alkylene;

when m is 4,

X is aliphatic $C_6$–$C_{18}$tetraacyl, aromatic $C_{10}$–$C_{18}$tetraacyl or a group of the formula (VIII)

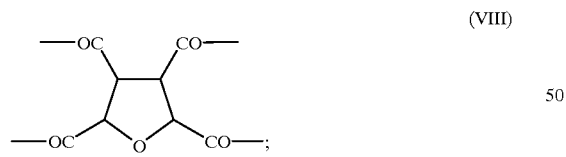

(VIII)

when m is 6, X is 1,2,3,4,5,6 cyclohexane carboxy residue;

when m is 2 and X is a group of the formula (IVa), the compounds of the formula (I) can be pure or mixtures containing at least two different compounds being $R_{18}$ a group of the formula —$(CH_2)_n$—, where n is an integer from 1 to 18.

Of special interest therein are compounds of formula I or II, wherein m is an integer from the range 1–4;

$R_1$ is hydrogen; $C_1$–$C_{18}$alkyl; oxyl; OH; $C_1$–$C_{18}$alkoxy; $C_5$–$C_{12}$cycloalkoxy; allyl; benzyl; benzyloxy; $C_2$–$C_8$alkanoyl; $C_3$–$C_5$alkenoyl;

$R_2, R_3, R_4, R_6, R_7, R_8$ and $R_9$ are, independently of one another, $C_1$–$C_4$alkyl or cyclohexyl;

or $R_2$ and $R_3$, $R_6$ and $R_7$, $R_8$ and $R_9$ form, together with the carbon atom they are attached to, $C_5$–$C_{12}$cycloalkylene;

$R_5$ is $C_1$–$C_4$alkylene;

$R'_{10}$ is hydrogen or methyl;

when m is 1, X is $C_5$–$C_{18}$alkyl; $C_5$–$C_{12}$cycloalkyl; allyl; glycidyl; $C_7$–$C_9$phenylalkyl; $C_7$–$C_9$phenylalkyl, which is substituted on the phenyl ring by methyl or methoxy; or is a group of formulae IIIa–IIIc —CO—$R_{11}$ (IIIa)

—$R_{12}$—COO—$R_{13}$ (IIIb)

—CO—NH—$R_{14}$ (IIIc)

wherein $R_{11}$ is $C_1$–$C_{17}$alkyl; $C_5$–$C_{12}$cycloalkyl; cyclohexyl, which is substituted by $C_1$–$C_4$alkyl; $C_2$–$C_3$alkenyl; phenyl; phenyl which is substituted by $C_1$–$C_4$alkyl, methoxy and/or hydroxy; $C_7$–$C_9$phenylalkyl;

$R_{12}$ is a direct bond, $C_1$–$C_{18}$alkylene or carbonyl;

$R_{13}$ and $R_{14}$, independently of each other, are $C_1$–$C_{18}$alkyl; $C_3$–$C_{18}$alkenyl; $C_5$–$C_{12}$cycloalkyl; $C_5$–$C_{12}$cycloalkyl, which is substituted by 1, 2 or 3 $C_1$–$C_4$alkyl;

when m is 2, X is $C_2$–$C_{12}$alkylene; $C_4$–$C_{12}$alkylene interrupted by oxygen; or is a group of formulae IVa–IVd —CO—$R_{18}$—CO— (IVa)

—COO—$R_{19}$—OCO— (IVb)

—CONH—$R_{20}$—NHCO— (IVc)

—$C_tH_{2t}$—CO— (IVd)

wherein t is zero or an integer from 1 to 7;

$R_{18}$ is a direct bond; $C_1$–$C_{22}$alkylene; $C_2$–$C_8$alkenylene; cyclohexylene; or phenylene;

$R_{19}$ is $C_2$–$C_{12}$alkylene; $C_4$–$C_{12}$alkylene interrupted by oxygen; cyclohexylene;

$R_{20}$ is $C_2$–$C_{12}$alkylene; cyclohexylene; or phenylene;

when m is 3, X is a trivalent residue of an alkane tricarboxylic acid having 4–12 carbon atoms, phenyltriacyl or a group of the formula VII

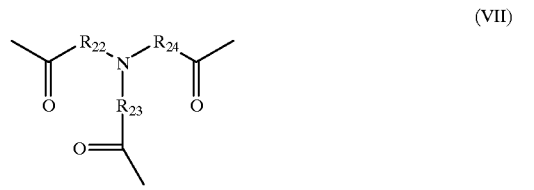

(VII)

wherein $R_{22}$, $R_{23}$ and $R_{24}$ are methylene;

when m is 4, X is a tetravalent residue of an alkane tetracarboxylic acid having 6–12 carbon atoms or phenyltetraacyl;

especially those, wherein m is an integer from the range 1–4;

$R_1$ is hydrogen; $C_1$–$C_8$alkyl; $C_5$–$C_{12}$alkoxy; cyclohexyloxy; benzyl; benzyloxy; $C_2$–$C_8$alkanoyl; $C_3$–$C_5$alkenoyl;

$R_2$, $R_3$, $R_4$, $R_6$, $R_7$, $R_8$ and $R_9$ are, independently of one another, $C_1-C_4$alkyl;

or $R_2$ and $R_3$, $R_6$ and $R_7$, $R_8$ and $R_9$ form, together with the carbon atom they are attached to, $C_5-C_{12}$cycloalkylene;

$R_5$ is $C_1-C_4$alkylene;

$R'_{10}$ is hydrogen or methyl;

when m is 1, X is $C_5-C_{18}$alkyl; $C_5-C_{12}$cycloalkyl; allyl; glycidyl; benzyl or benzyl, which is substituted on the phenyl ring by methyl or methoxy; or is a group of formulae IIIa —CO—$R_{11}$ (IIIa)

wherein $R_{11}$ is $C_1-C_{17}$alkyl; $C_5-C_{12}$cycloalkyl; cyclohexyl, which is substituted by $C_1-C_4$alkyl; $C_2-C_3$alkenyl; phenyl; benzyl;

when m is 2, X is $C_2-C_{12}$alkylene; or is a group of formulae IVa

—CO—$R_{18}$—CO— (IVa)

wherein $R_{18}$ is a direct bond; $C_1-C_{22}$alkylene; $C_2-C_8$alkenylene; cyclohexylene; or phenylene;

when m is 3, X is phenyltriacyl or a group of the formula VII

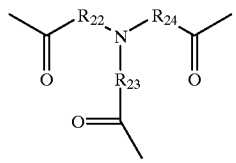

(VII)

wherein $R_{22}$, $R_{23}$ and $R_{24}$ are methylene;

when m is 4, X is phenyltetraacyl;

particularly those, wherein m is 1 or 2;

$R_1$ is hydrogen or $C_1-C_8$alkyl;

$R_2$, $R_3$, $R_4$, $R_6$, $R_7$, $R_8$ and $R_9$ are, independently of one another, methyl or ethyl;

$R_5$ is methylene;

$R'_{10}$ is hydrogen or methyl;

when m is 1, X is a group —CO—$R_{11}$ wherein $R_{11}$ is $C_1-C_{17}$alkyl;

when m is 2, X is a group —CO—$R_{18}$—CO— wherein $R_{18}$ is a direct bond or $C_1-C_{12}$alkylene.

The compounds of the present invention can be prepared in analogy to methods known in the art, for example by etherification, esterification or substitution of amines. Such methods are described, for example, in U.S. Pat. No. 3,840,494, U.S. Pat. No. 3,640,928, in "The Chemistry of the ether linkage" edited by S. Patai, Interscience Publishers, London, 1967, or in U.S. Pat. No. 5,449,776. Further methods which can be applied in analogous manner for introducing a variety of substituents on the N atom in the morpholinone structure are described, for example, by L. B. Volodorsky et al., synthetic chemistry of stable nitroxide, CRC Press, Boca Raton 1994; T. J. Connolly et al., Tetr. Lett. 37, 4919 (1996); I. Li et al., Polym. Prep. 36, 469 (1996); and in EP-A-375612 and publications cited therein, as well as U.S. Pat. No. 5,449,776, example 8, for the methylation of piperidine derivatives.

The reactions can be effected in an inert organic solvent, such as an aromatic or aliphatic hydrocarbon, ether, amide or alcohol, for example toluene, xylene, trimethylbenzene, tetrahydrofuran, dioxane, tert-amylalcohol, dimethyl formamide, N,N-dimethylacetamide, operating at a temperature from 40° C. to 180° C., preferably from 80° C. to 160° C.

Suitable starting materials are, for example, 2-morpholinone compounds as described in EP-A-248494, in U.S. Pat. Nos. 4,528,370, 4,914,232, 5,089,614, especially examples Nos. 2A–C and 7A–F, or by J. T. Lai in Synthesis (1984), 122, especially compounds Nos. 4a–e. These and other starting compounds having the 2-morpholinone structure can be prepared according to or in analogy to the methods described in these documents, e.g. in U.S. Pat. No. 4,528,370, column 4, line 67, to column 5, line 14, and in a more detailed manner in column 7, lines 15–56.

The preparation of their precursurs, i.e. substituted hydroxyethylaminoacetates (HEAA), is described in U.S. Pat. No. 4,528,370 from column 3, line 65, to column 4, line 66, in column 5, lines 47–58, and more detailed from column 6, line 26, to column 7, line 13. Further precursors (HEAA) can be obtained in analogy to the methods described e.g. in U.S. Pat. Nos. 4,528,370, 4,914,232 or 5,089,614.

For instance, a useful educt for the preparation of present compounds is a compound of the formula

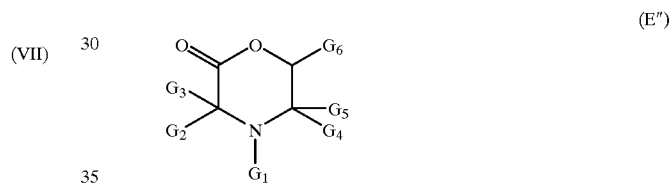

(E″)

containing one group —$R_{10}$—ZH or —$R_5$—ZH;

wherein $G_1$ is hydrogen; $C_1-C_{18}$alkyl; $C_2-C_{18}$hydroxyalkyl; oxyl; OH; $C_2-C_{12}$cyanoalkyl; $C_2-C_{12}$cyanoalkoxy; $C_1-C_{18}$alkoxy; $C_5-C_{12}$cycloalkoxy; $C_3-C_8$alkenyl; $C_3-C_8$alkynyl; $C_3-C_8$alkenyloxy; $C_7-C_{12}$phenylalkyl; $C_7-C_{12}$phenylalkyl substituted by hydroxy, $C_1-C_4$alkyl and/or $C_1-C_4$alkoxy; $C_7-C_{15}$phenylalkoxy; $C_7-C_{15}$phenylalkoxy, which is substituted by $C_1-C_4$alkyl and/or $C_1-C_4$alkoxy; or $G_1$ is $C_1-C_8$alkanoyl; $C_3-C_5$alkenoyl; $C_1-C_{18}$alkanoyloxy; $C_3-C_8$epoxyalkyl;

or $G_1$ is the group —$R_{10}$—ZH;

$G_2$ and $G_4$ are, independently of one another, $C_1-C_{18}$alkyl, $C_5-C_{12}$cycloalkenyl, $C_6-C_{12}$bicycloalkyl; $C_6-C_{12}$bicycloalkenyl or $C_5-C_{12}$cycloalkyl;

$G_3$ is as defined for $G_2$ or is $C_1-C_8$hydroxyalkyl; or $G_2$ and $G_3$ together are $(CH_2)_e$, where e is a number from 4 to 11;

or $G_3$ is the group —$R_5$—ZH;

$G_5$ is as defined for $G_4$ or is $C_1-C_8$hydroxyalkyl; or $G_4$ and $G_5$ together are $(CH_2)_e$, where e is a number from 4 to 11;

or $G_5$ is the group —$R_5$—ZH;

$G_6$ is as defined for $G_4$ or is hydrogen;

or $G_6$ is the group —$R_5$—ZH;

$R_5$ is $C_1-C_8$alkylene; $C_1-C_8$alkylene-CO—; or $C_1-C_8$alkylene substituted by OH or OCOR$_{15}$;

$R_{10}$ is $C_1$–$C_8$alkylene or $C_1$–$C_8$alkylene-CO—;

$R_{15}$ is hydrogen; $C_1$–$C_{17}$alkyl; $C_3$–$C_{50}$alkyl interrupted by O; $C_5$–$C_{12}$cycloalkyl; $C_5$–$C_{12}$cycloalkyl, which is substituted by $C_1$–$C_4$alkyl; $C_2$–$C_{17}$alkenyl; phenyl; phenyl which is substituted by $C_1$–$C_4$alkyl, $C_1$–$C_4$alkoxy and/or hydroxy; $C_7$–$C_{15}$phenylalkyl; $C_7$–$C_{15}$phenylalkyl, which is substituted by $C_1$–$C_4$alkyl, $C_1$–$C_4$alkoxy and/or hydroxy; or is $C_8$–$C_{12}$phenylalkenyl;

$R'_{14}$ is hydrogen, $C_1$–$C_{18}$alkyl; $C_5$–$C_{12}$cycloalkyl; $C_5$–$C_{12}$cycloalkyl, which is substituted by $C_1$–$C_4$alkyl; $C_2$–$C_{17}$alkenyl; $C_7$–$C_{15}$phenylalkyl; $C_7$–$C_{15}$phenylalkyl, which is substituted by $C_1$–$C_4$alkyl, $C_1$–$C_4$alkoxy; and ZH is —OH, —NHR'$_{14}$, —SH, oxiranyl, or halogen.

Examples are morpholinones of the formula (X)

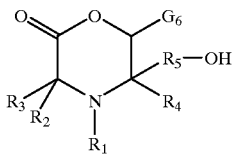

(X)

where $R_1$, $R_2$, $R_3$, $R_4$, $R_5$, $G_6$ have the above mentioned meanings.

These compounds can be prepared by known methods or in analogy to these methods, see passages of U.S. Pat. No. 4,528,370 cited above, especially columns 19 and 20, example 7E.

Compounds of the formula E" or X may be further reacted, e.g. etherified or esterified as described above to obtain compounds of the invention.

An alternative path to present compounds, e.g. of the formula I, which are substituted on the N atom, starts with compounds of the formulae E", F, I or X wherein $R_1$ is hydrogen by introducing a substituent on the N atom in the morpholinone structure in analogy to methods described in publications cited above. For example, these compounds may be methylated on the N-atom following the general procedure described in EP-A-375612 and publications cited therein, as well as U.S. Pat. No. 5,449,776, example 8, for the methylation of piperidine derivatives.

Expediently, this reaction is carried out in an inert solvent, such as a hydrocarbon, ether or alcohol, especially a tertiary alcohol such as tert.amylalcohol in the temperature range from 20–150, especially 50–120° C. Formaldehyde, especially paraformaldehyde, and formic acid are preferably added in large excess relative to the unmethylated starting compound, often an excess from 1.2 to 20 fold, for example 2–12 fold excess of paraformaldehyde and formic acid, independently, is used.

Working up can be achieved in a conventional manner, often by neutralizing, e.g. by addition of alkali or alkali earth carbonates, oxides or hydroxides such as sodium or potassium carbonate, separation of the organic phase containing the product and removing the solvent, optionally after drying.

Examples for compounds obtainable in analogy to known methods are compounds of the formula (XI)

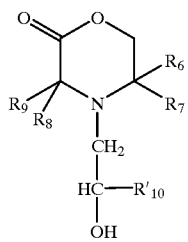

(XI)

where $R_6$, $R_7$, $R_8$, $R_9$, $R'_{10}$ have the above mentioned meanings. These compounds can be prepared in analogy to methods known in the art for piperidine derivatives, e.g. in EP-A-58434, page 24, line1 7, to page 25, line 19, and examples.

Compounds of the formula (XI) can expediently be prepared by reacting a compound of the formula (XII)

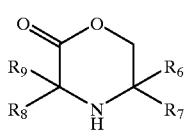

(XII)

where $R_6$, $R_7$, $R_8$, $R_9$ are as previously defined, with the suitable epoxide of the formula (XIII)

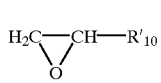

(XIII)

where $R'_{10}$ is as previously defined. Expediently, the addition reaction is carried out in an alcoholic solvent such as methanol, ethanol propanol at a temperature from 60° C. to 180° C., preferably from 100° C. to 160° C. The reaction can be carried out in all pressure ranges; preferred is a pressure from about 1 to 20 bars, e.g. 2 to 20 bars, preferably from 2 to 5 bars.

The compound of the formula (XII) can be prepared according to the general procedure and examples given in U.S. Pat. No. 4,528,370 (see above).

Further analoguous methods for preparing compounds of the invention are described in the examples further below.

Some of the intermediates used for preparing stabilizers of present formula F are novel compounds. The invention therefore also pertains to a compound of the formula E'

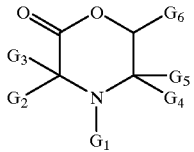

(E')

containing one group —$R_{10}$—ZH or —$R_5$—ZH;
wherein
  $G_1$ is hydrogen; $C_1$–$C_{18}$alkyl; $C_2$–$C_{18}$hydroxyalkyl; oxyl; OH; $C_2$–$C_{12}$cyanoalkyl; $C_2$–$C_{12}$cyanoalkoxy; $C_1$–$C_{18}$alkoxy; $C_5$–$C_{12}$cycloalkoxy; $C_3$–$C_8$alkenyl; $C_3$–$C_8$alkynyl; $C_3$–$C_8$alkenyloxy; $C_7$–$C_{12}$phenylalkyl; $C_7$–$C_{12}$phenylalkyl substituted by hydroxy, $C_1$–$C_4$alkyl and/or $C_1$–$C_4$alkoxy; $C_7$–$C_{15}$phenylalkoxy; $C_7$–$C_{15}$phenylalkoxy, which is substituted by $C_1$–$C_4$alkyl and/or $C_1$–$C_4$alkoxy; or $G_1$ is $C_1$–$C_8$alkanoyl; $C_3$–$C_5$alkenoyl; $C_1$–$C_{18}$alkanoyloxy; $C_3$–$C_8$epoxyalkyl;

or $G_1$ is the group —$R_{10}$—ZH;

$G_2$ and $G_4$ are, independently of one another, $C_1$–$C_{18}$alkyl, $C_5$–$C_{12}$cycloalkenyl, $C_6$–$C_{12}$bicycloalkyl; $C_6$–$C_{12}$bicycloalkenyl or $C_5$–$C_{12}$cycloalkyl;

$G_3$ is as defined for $G_2$ or is $C_1$–$C_8$hydroxyalkyl; or $G_2$ and $G_3$ together are $(CH_2)_e$, where e is a number from 4 to 11;

or $G_3$ is the group —$R_5$—ZH;

$G_5$ is as defined for $G_4$ or is $C_1$–$C_8$hydroxyalkyl; or $G_4$ and $G_5$ together are $(CH_2)_e$, where e is number from 4 to 11;

and if $G_1$ is not hydrogen, $G_5$ also may be the group —$R_5$—ZH;

$G_6$ is as defined for $G_4$ or is hydrogen;

or $G_6$ is the group —$R_5$—ZH;

$R_5$ is $C_1$–$C_8$alkylene; $C_1$–$C_8$alkylene-CO—; or $C_1$–$C_8$alkylene substituted by OH or $OCOR_{15}$;

$R_{10}$ is $C_1$–$C_8$alkylene or $C_1$–$C_8$alkylene-CO—;

$R_{15}$ is hydrogen; $C_1$–$C_{17}$alkyl; $C_3$–$C_{50}$alkyl interrupted by O; $C_5$–$C_{12}$cycloalkyl; $C_5$–$C_{12}$cycloalkyl, which is substituted by $C_1$–$C_4$alkyl; $C_2$–$C_{17}$alkenyl; phenyl; phenyl which is substituted by $C_1$–$C_4$alkyl, $C_1$–$C_4$alkoxy and/or hydroxy; $C_7$–$C_{15}$phenylalkyl, which is substituted by $C_1$–$C_4$alkyl, $C_1$–$C_4$alkoxy and/or hydroxy; or is $C_8$–$C_{12}$phenylalkenyl;

$R'_{14}$ is hydrogen, $C_1$–$C_{18}$alkyl; $C_5$–$C_{12}$cycloalkyl; $C_5$–$C_{12}$cycloalkyl, which is substituted by $C_1$–$C_4$alkyl; $C_2$–$C_{17}$alkenyl; $C_7$–$C_{15}$phenylalkyl; $C_7$–$C_{15}$phenylalkyl, which is substituted by $C_1$–$C_4$alkyl, $C_1$–$C_4$alkoxy; and ZH is —OH, —$NHR'_{14}$, —SH, oxiranyl, or halogen; and the compound 3-methyl-3-ethyl-5-hydroxymethyl-5-ethyl-2-morpholinone.

Preferred are intermediates of the formula E' containing 1 or 2 free hydroxy groups, for example those wherein 1 or 2 of the residues $G_1$, $G_3$ and $G_5$ are hydroxyalkyl and other residues $G_1$–$G_6$ have one of the meanings initially defined as preferred within the definitions given for formula E.

Some of the most preferred novel intermediates are of the formula (XI)

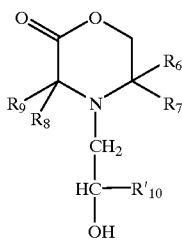

(XI)

where $R_6$, $R_7$, $R_8$, $R_9$, $R'_{10}$ are as previously defined, used as an intermediate for preparing compounds of the formula II are novel and form therefore another subject of the invention.

Novel precursors of the HEAA type of the formula XIV

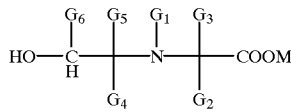

(XIV)

wherein $G_1$ is hydrogen; $C_1$–$C_{18}$alkyl; $C_2$–$C_{18}$hydroxyalkyl; oxyl; OH; $C_2$–$C_{12}$cyanoalkyl; $C_2$–$C_{12}$cyanoalkoxy; $C_1$–$C_{18}$alkoxy; $C_5$–$C_{12}$cycloalkoxy; $C_3$–$C_8$alkenyl; $C_3$–$C_8$alkynyl; $C_3$–$C_8$alkenyloxy; $C_7$–$C_{12}$phenylalkyl; $C_7$–$C_{12}$phenylalkyl substituted by hydroxy, $C_1$–$C_4$alkyl and/or $C_1$–$C_4$alkoxy; $C_7$–$C_{15}$phenylalkoxy; $C_7$–$C_{15}$phenylalkoxy, which is substituted by $C_1$–$C_4$alkyl and/or $C_1$–$C_4$alkoxy; or $G_1$ is $C_1$–$C_8$alkanoyl; $C_3$–$C_5$alkenoyl; $C_1$–$C_{18}$alkanoyloxy; $C_3$–$C_8$epoxyalkyl;

$G_2$, $G_3$, $G_4$ and $G_5$ are, independently of one another, $C_1$–$C_{18}$alkyl, $C_5$–$C_{12}$cycloalkenyl, $C_6$–$C_{12}$bicycloalkyl; $C_6$–$C_{12}$bicycloalkenyl or $C_5$–$C_{12}$cycloalkyl;

$G_6$ is $C_1$–$C_{18}$alkyl; $C_1$–$C_{18}$alkyl interrupted by O or substituted by $C_5$–$C_{12}$cycloalkyl, phenyl, OH, phenoxy, $C_1$–$C_{18}$alkoxy, $C_5$–$C_{12}$cycloalkoxy, halogen, $COOR_{15}$ or O—$COR_{15}$; or wherein $G_6$ is $C_2$–$C_{18}$alkenyl; phenyl; phenyl substituted by alkyl or OH, $C_5$–$C_{12}$cycloalkyl;

M is a negative charge or alkali metal;

$R_{15}$ is hydrogen; $C_1$–$C_{17}$alkyl; $C_5$–$C_{12}$cycloalkyl; $C_5$–$C_{12}$cycloalkyl, which is substituted by $C_1$–$C_4$alkyl; $C_2$–$C_{17}$alkenyl; phenyl; phenyl which is substituted by $C_1$–$C_4$alkyl, $C_1$–$C_4$alkoxy and/or hydroxy; $C_7$–$C_{15}$phenylalkyl; $C_7$–$C_{15}$phenylalkyl, which is substituted by $C_1$–$C_4$alkyl, $C_1$–$C_4$alkoxy and/or hydroxy; or is $C_8$–$C_{12}$phenylalkenyl, are a further object of the invention.

Preferred meanings for residues in formula XIV are as defined above for morpholinone compounds of the invention.

Although the novel intermediates of formulae XI, XIV and E' find their use mainly in the preparation of present compounds of the formula F, they are also active as stabilizer and can be used accordingly, alone or in combination with present compound of formula F or a conventional stabilizer.

The novel compounds of present invention, for example those of formula F, especially those of formula I, II or III, can be employed with advantage for stabilizing organic material against the damaging effect of light, oxygen and/or heat. They are notable for high substrate compatibility and good persistence in the substrate.

The materials to be stabilized can, for example, be oils, fats, waxes, cosmetics or biocides. Particular interest attaches to use in polymeric materials, as in plastics, rubbers, coating materials, photographic materials or adhesives. Examples of polymers and other substrates which can be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or ($\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or ($\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4, -trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore also provides compositions comprising
A) an organic material which is sensitive to oxidative, thermal and/or actinic degradation, and
B) at least one compound of the formula F, e.g. of the formula I, II and/or III, and provides for the use of compounds of the formula F for stabilizing organic material against oxidative, thermal or actinic degradation.

The invention likewise comprises a method of stabilizing organic material against thermal, oxidative and/or actinic degradation, which comprises adding to this material at least one compound of the formula F.

Of particular interest is the use of compounds of the formula F as stabilizers in synthetic organic polymers, reprographic, especially photographic material, coatings or cosmetic formulations, especially in thermoplastic polymers and corresponding compositions as well as in coating compositions. Thermoplastic polymers of most importance in present compositions are polyolefines and their copolymers, such as listed above under items 1–3, thermoplastic polyolefin (TPO), thermoplastic polyurethan (TPU), thermoplastic rubber (TPR), polycarbonate, such as in item 19 above, and blends, such as in item 28 above. Of utmost importance are polyethylene (PE), polypropylene (PP), polycarbonate (PC) and polycarbonate blends such as PC/ABS blends.

Some of the above compounds of the formula F are especially well suitable for grafting them onto organic polymers having suitable functional groups. These are mainly compounds of the formula F carrying a hydroxy or epoxy group or an ethylenic double bond.

The invention therefore also pertains to a process for grafting a compound of the formula F carrying a hydroxy or epoxy group or an ethylenic double bond onto an onto polymer carrying suitable functional groups.

Compounds of the formula F suitable for grafting and carrying a hydroxy group are preferably compounds of the formula F, wherein m is 1 and X is hydroxyalkyl or epoxyalkyl or carboxyalkyl; or wherein one of $G_1$, $G_3$ or $G_5$ is hydroxyalkyl; or wherein $G_1$ is epoxyalkyl.

Polymers having suitable functional groups for the reaction with the hydroxy compounds of formula F are mainly organic polymers containing carboxy, anhydride or epoxy groups. Vice versa, polymers containing hydroxy groups are suitable for reactive bonding with present compounds of the formula F, which contain an epoxy or carboxy group.

Compounds of the formula F suitable for grafting and carrying an epoxy group are preferably compounds of the formula F, wherein m is 1 and X or $G_1$ is $C_3$–$C_{12}$epoxyalkyl, especially glycidyl.

Polymers having suitable functional groups for the reaction with these epoxy compounds are mainly organic polymers containing carboxy and/or hydroxy groups.

Compound s of the formula F suitable for grafting and carrying an ethylenic double bond are preferably compounds of the formula F, wherein m is 1 and X contains a $C_3$–$C_8$alkenyl moiety or $G_1$ is $C_3$–$C_8$ alkenyl or $C_3$–$C_8$alkenyloxy. Grafting is preferably effected by exposure to UV light (photografting).

Polymer s having suitable functional groups for the reaction with these double bonds are mainly unsaturated organic polymers containing ethylenic double bonds in the main chain or in side chains.

Difunctional groups of present formula F, for example compounds containing 2 hydroxy groups, also can act as crosslinkers when used together with suitable polymers as described.

Grafting reactions can be carried out in close analogy to methods known in the art, e.g. to methods described in EP-A-526399, pages 6–16, or to methods described in U.S. Pat. No. 5,189,084. Modified polymers thus obtained are highly stable against deleterious effects of light, oxygen and heat. If they contain reactively bonded units of present formula F in a sufficient amount, e.g. in an amount of 0.5 to 50 g, especially 2 to 20 g units of the formula F on 100 g of the final polymer, these modified polymers themselves can be used as stabilizers.

Other materials to be stabilized with the novel compositions are recording materials. By such materials are meant, for example, those described in Research Disclosure 1990, 31429 (pages 474–480), or in GB-A-2319523 or DE-A-1 9750906, page 22, line 15, until page 105, line 32, for photographic reproduction and other reprographic techniques.

Of special importance is the stabilization of non-silver reprographic materials, for example, those for pressure-sensitive copying systems, microcapsule photocopier systems, heat-sensitive copier systems and ink-jet printing.

The novel recording materials feature an unexpectedly high quality, especially in terms of their light stability.

The novel recording materials have a structure which is known per se and which corresponds to the utility. They consist of a base, for example paper or plastic film, on which one or more coatings are applied. Depending on the type of material, these coats contain the suitable components required, in the case of photographic material for example silver halide emulsions, colour couplers, dyes and the like. The material intended especially for ink-jet printing has a customary base on which there is an absorption layer suitable for ink. Uncoated paper can likewise be employed for ink-jet printing; in this case, the paper functions simultaneously as a base and has the absorbent for the ink. Suitable material for ink-jet printing is described, inter alia, in U.S. Pat. No. 5,073,448, the disclosure content of which is regarded as part of the present description.

The recording material can also be transparent, for example in the case of projection films.

The compound or compounds of the formula F can be incorprated into the material even in the course of manufacture; in papermaking, for example, by addition to the pulp. Another method of use is the spraying of the material with an aqueous solution of compound(s) of the formula F, or the addition thereof to the coating.

Coatings for transparent recording materials for projection must not contain any light-scattering particles such as pigments or fillers.

The colour-binding coatings can contain further additives, for example antioxidants, light stabilizers (including UV absorbers or hindered amine light stabilizers which are not included among the novel compounds of formula F), viscosity improvers, brighteners, biocides and/or antistats.

The coating is usually prepared as follows:

The water-soluble components, for example the binder, are dissolved in water and mixed. The solid components, for example fillers and other additives as already described, are dispersed in this aqueous medium. Dispersion is advantageously brought about with the aid of equipment such as ultrasonic devices, turbine agitators, homogenizers, colloid mills, bead mills, sand mills, high-speed stirrers and the like. A particular advantage of the compounds of the formula F is their ease of incorporation into the coating.

As mentioned, the novel recording materials cover a broad field of use. Compounds of the formula F can be employed, for example, in pressure-sensitive copier systems. They can be added to the paper to protect the microencapsulated dye precursors against light, or to the binder of the developer layer for protecting the dyes formed therein.

Photocopier systems with light-sensitive microcapsules which are developed by pressure are described, inter alia, in U.S. Pat. Nos. 4,416,966; 4,483,912; 4,352,200; 4,535,050; 4,536,5463; 4,551,407; 4,562,137 and 4,608,330; and also in EP-A-139479; EP-A-162664; EP-A-164931; EP-A-237024; EP-A-237025 and EP-A-260129. In all these systems the compounds of the formula F can be added to the colour-accepting layer. Alternatively, the compounds of the formula F can be added to the donor layer for protecting the colour formers against light.

The compounds of the formula F can also be employed in recording materials which are based on the principle of photopolymerization, photosoftening or the rupture of microcapsules, or when heat-sensitive or photosensitive diazonium salts, leuco dyes with oxidizing agent or colour lactones with Lewis acids are used.

Heat-sensitive recording material exploits the colour-imparting reaction between a colourless or weakly coloured base dye and an organic or inorganic colour developer, the recorded image being produced by heat-induced contact of the two materials. This type of heat-sensitive recording material is very widespread, not only as the recording medium for faxes, computers, etc., but also in many other fields, for example in label printing.

The heat-sensitive recording material according to the present invention is composed of a base, a heat-sensitive colour-forming recording layer on this base, and, optionally, a protective layer on the heat-sensitive, colour-forming recording layer. The heat-sensitive, colour-forming recording layer contains as its principal constituent a colour-imparting compound and a colour-developing compound, and also a compound of the formula F. If the said protective layer is present, the compound of the formula F can also be incorporated into the protective layer.

Heat-sensitive recording materials are described, for example, in JP-A 8-267 915.

Further fields of use are recording materials for dye diffusion transfer printing, thermal wax transfer printing and dot matrix printing, and for use with electrostatic, electrographic, electrophoretic, magnetographic and laser-electrophotographic printers, recorders or plotters.

Of the materials mentioned, preference is given to recording materials for dye diffusion transfer printing, as are described, for example, in EP-A-507,734.

Compounds of the formula F can also be employed in inks, preferably for ink-jet printing, for example those as described in U.S. Pat. No. 5,098,477, the disclosure content of which is regarded as part of the present description. The invention therefore also provides an ink comprising at least one compound of the formula F as stabilizer. The ink, especially for ink-jet printing, contains preferably water. Inks contain the stabilizer of the formula F usually in a concentration of from 0.01 to 20% by weight, in particular from 0.5 to 10% by weight.

The novel recording materials, for example photographic recording materials, also offer the advantage over materials comprising conventional HALS that the stabilizers of the formula F are required in a comparatively small amount, meaning also that the thickness of the stabilizer-containing layer remains low, a factor which has a positive effect, inter alia, on the imaging properties. Another advantage of the novel stabilizers is their heightened inherent stability under extreme climatic conditions, especially at high humidity and high temperature. The novel photographic material can be a black and white or a colour photographic material; colour photographic material is preferred.

Examples of colour photographic materials are colour negative films, colour reversal films, colour positive films, colour photographic paper, colour reversal photographic paper, colour-sensitive materials for the dye diffusion transfer process or the silver dye bleach process. Details of the photographic material to be stabilized according to the invention and components which can be employed in the novel material are given, inter alia, in GB-A-2319523, DE-A-19750906, page 23, line 20, until page 105, line 32, and in U.S. Pat. No. 5,538,840, column 25, line 60, to column 106, line 31; these parts of U.S. Pat. No. 5,538,840 are incorporated herein by way of reference.

The compounds of the invention are also valuable light stabilizers in cosmetic, pharmaceutical or veterinary formulations. The substrate to be protected in these applications may be the formulation itself or components thereof, or human or animal skin or hair. The compounds of the invention may be used in dissolved or micronized state. The invention therefore also pertains to a cosmetic formulation containing at least one compound of the formula F and cosmetically acceptable carriers or auxiliary agents. A more detained description of the cosmetic formulations which can be stabilized according to the invention can be found in GB-A-2319523.

The organic polymeric materials to be protected are preferably natural, semisynthetic or, preferably, synthetic organic materials. Particular preference is given to synthetic organic polymers or mixtures of such polymers, especially thermoplastic polymers such as polyolefins, especially polyethylene and polypropylene (PP), and coating compositions.

In general the compounds of the formula F are added to the material to be stabilized in amounts of from 0.1 to 10%, preferably from 0.01 to 5%, in particular from 0.01 to 2% (based on the material to be stabilized). Particular preference is given to the use of the novel compounds in amounts of from 0.05 to 1.5%, especially from 0.1 to 0.5%.

Incorporation into the materials can be effected, for example, by mixing in or applying the compounds of the formula F and, if desired, further additives by the methods which are customary in the art. Where polymers are involved, especially synthetic polymers, incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the compounds of the formula F into polymers is to add them before, during or directly after the polymerization of the corresponding monomers or prior to crosslinking. In this context the compound of the formula F can be added as it is or else in encapsulated form (for example in waxes, oils or polymers). In the case of addition prior to or during the polymerization, the compounds of the formula F can also act as a regulator of the chain length of the polymers (chain terminator).

The compounds of the formula F can also be added in the form of a masterbatch containing said compound in a concentration, for example, of from 2.5 to 25% by weight to the polymers that are to be stabilized.

The compounds of the formula F can judiciously be incorporated by the following methods:
- as emulsion or dispersion (e.g. to latices or emulsion polymers),
- as a dry mixture during the mixing in of additional components or polymer mixtures,
- by direct introduction into the processing apparatus (e.g. extruders, internal mixers, etc),
- as solution or melt.

Novel polymer compositions can be employed in various forms and/or processed to give various products, for example as (to give) films, fibres, tapes, moulding compositions, profiles, or as binders for coating materials, adhesives or putties.

In addition to the compounds of the formula F the novel compositions may as additional component C comprise one or more conventional additives such as, for example, those indicated below.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl- 4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tertbutyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3, 5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl N,N'-di-sec-butyl-p-phenylenediamine, diphenylamine, N-allyidiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N', N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl- 2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO—$CH_2CH_2$]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl) phenyl]benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2-{2-hydroxy-4-[1-octyloxycarbonyl-ethoxy]phenyl}-4,6-bis(4-phenylphenyl)-1,3,5-triazine wherein the octyl moiety is a mixture of different isomers.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-di-yl)phosphite.

Especially preferred are the following phosphites:

Tris(2,4-di-tert-butylphenyl) phosphite (Irgafos®168, Ciba-Geigy), tris(nonylphenyl) phosphite,

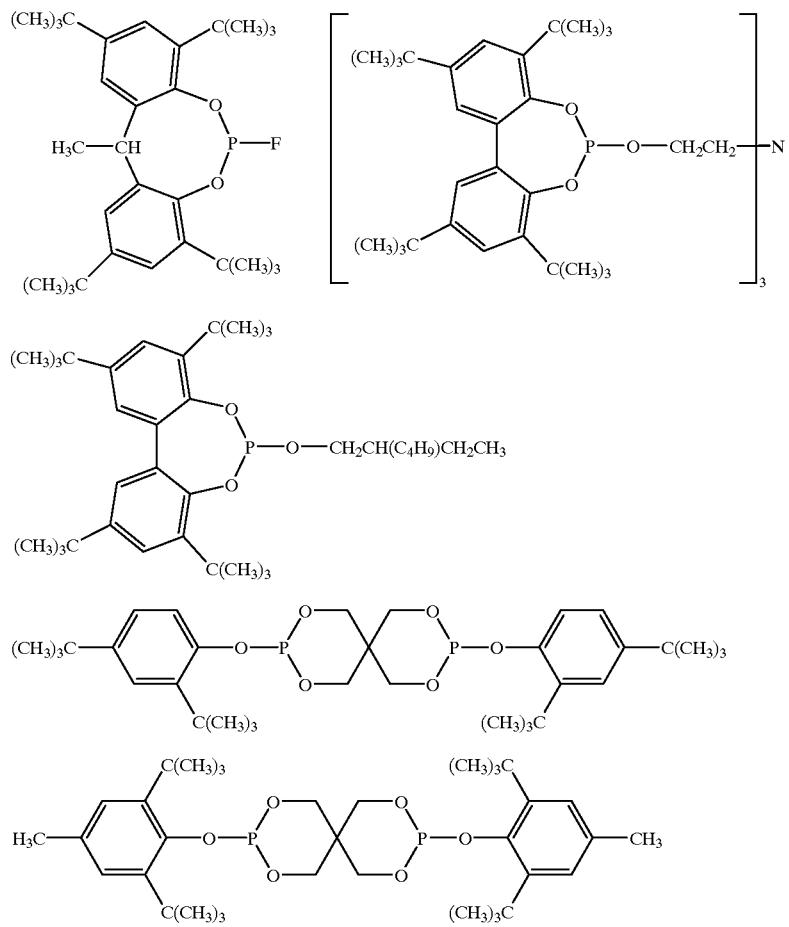

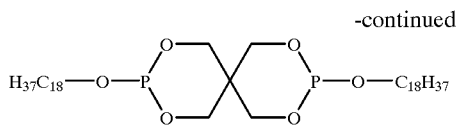 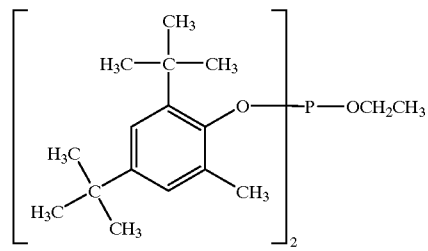

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhy-droxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The conventional additives are judiciously employed in amounts of 0.1–10% by weight, for example 0.2–5% by weight, based on the material to be stabilized.

Costabilizers optionally to be added to the stabilizer mixture of the invention are preferably further light stabilizers, for instance those of the 2-hydroxyphenyl-benztriazole, 2-hydroxyphenyl-triazine, benzophenone or oxalanilide classes, e.g. as described in EP-A-453396, EP-A-434608, U.S. Pat. No. 5,298,067, WO 94/18278, GB-A-2297091 and WO 96/28431, and/or further hindered amines derived from 2,2,6,6-tetraalkylpiperidine containing at least one group of the formula

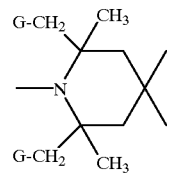

in which G is hydrogen or methyl, especially hydrogen; examples of tetraalkylpiperidine derivatives which can be used as costabilizers with mixtures of the invention are given in EP-A-356 677, pages 3–17, sections a) to f). These sections of this EP-A are regarded as part of the present description.

Especially preferred as costabilizers are 2-hydroxyphenyl-benztriazoles and/or 2-hydroxyphenyl-triazines such as a benzotriazole of formula K, L, M or N

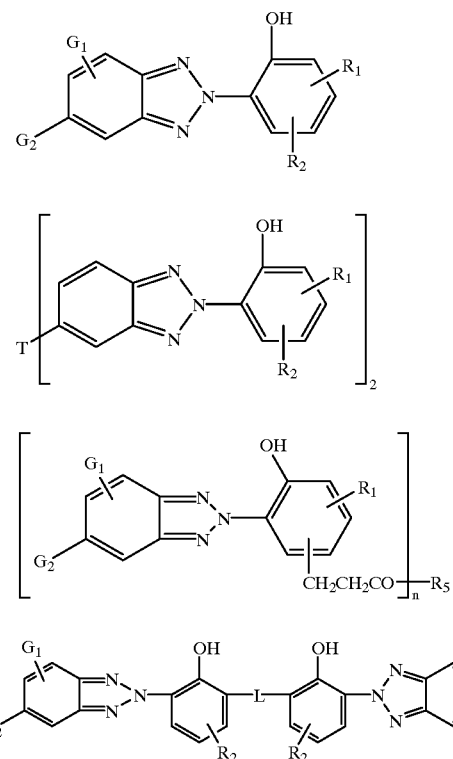

wherein $G_1$ is hydrogen or halogen, $G_2$ is hydrogen, halogen, nitro, cyano, $R_3SO$—, $R_3SO_2$—, —$COOG_3$, $CF_3$—, —$P(O)(C_6H_5)_2$, —CO—$G_3$, —CO—NH—$G_3$, —CO—N$(G_3)_2$, —N$(G_3)$—CO—$G_3$,

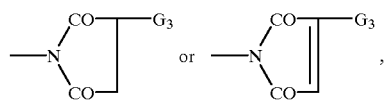

especially H, Cl, $C_1$–$C_4$alkyl or $C_1$–$C_4$alkoxy;

$G_3$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, $R_1$ is hydrogen or straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, $R_2$ is hydrogen or straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $R_2$ is hydroxyl or —$OR_4$ where $R_4$ is straight or branched chain alkyl of 1 to 24 carbon atoms; or said alkyl substituted by one or more —OH, —OCO—$R_{11}$, —$OR_4$, —NCO or —$NH_2$ groups or mixtures thereof; or said alkyl or said alkenyl interrupted by one or more —O—, —NH— or —$NR_4$— groups or mixtures thereof and which can be unsubstituted or substituted by one or more —OH, —$OR_4$ or —$NH_2$ groups or mixtures thereof; or $R_2$ is —$SR_3$, —$NHR_3$ or —$N(R_3)_2$; or $R_2$ is —$(CH_2)_m$—CO—X—$(Z)_p$—Y—$R_{15}$ wherein X is —O— or —$N(R_{16})$—, Y is —O— or —$N(R_{17})$—, Z is $C_2$–$C_{12}$-alkylene, $C_4$–$C_{12}$-alkylene interrupted by one to three nitrogen atoms, oxygen atoms or a mixture thereof, or is $C_3$–$C_{12}$-alkylene, butenylene, butynylene, cyclohexylene or phenylene, each substituted by a hydroxyl group, m is zero, 1 or 2, p is 1, or p is also zero when X and Y are —$N(R_{16})$— and —$N(R_{17})$—, respectively, $R_{15}$ is a group —CO—$C(R_{18})$=$C(H)R_{19}$ or, when Y is —$N(R_{17})$—, forms together with $R_{17}$ a group —CO—CH=CH—CO—, wherein $R_{18}$ is hydrogen or methyl, and $R_{19}$ is hydrogen, methyl or —CO—X—$R_{20}$, wherein $R_{20}$ is hydrogen, $C_1$–$C_{12}$-alkyl or a group of the formula

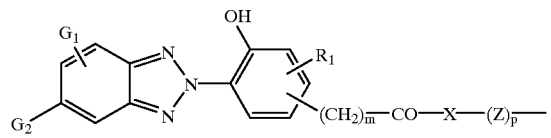

wherein the symbols $R_1$, $R_3$, X, Z, m and p have the meanings defined above, and $R_{16}$ and $R_{17}$ independently of one another are hydrogen, $C_1$–$C_{12}$-alkyl, $C_3$–$C_{12}$-alkyl interrupted by 1 to 3 oxygen atoms, or is cyclohexyl or $C_7$–$C_{15}$aralkyl, and $R_{16}$ together with $R_{17}$ in the case where Z is ethylene, also forms ethylene, n is 1 or 2, when n is 1, $R_5$ is Cl, $OR_6$ or $NR_7R_8$, or $R_5$ is —$PO(OR_{12})_2$, —$OSi(R_{11})_3$ or —OCO—$R_{11}$, or straight or branched chain $C_1$–$C_{24}$alkyl which is interrupted by —O—, —S— or —$NR_{11}$ and which can be unsubstituted or substituted by —OH or —OCO—$R_{11}$, $C_5$–$C_{12}$ cycloalkyl which is unsubstituted or substituted by —OH, straight chain or branched $C_2$–$C_{18}$alkenyl which is unsubstituted or substituted by —OH, $C_7$–$C_{15}$aralkyl, —$CH_2$—CHOH—$R_{13}$ or glycidyl, $R_6$ is hydrogen, straight or branched chain $C_1$–$C_{24}$alkyl which is unsubstituted or substituted by one or more OH, $OR_4$ or $NH_2$ groups, or —$OR_6$ is —$(OCH_2CH_2)_w$OH or —$(OCH_2CH_2)_wOR_{21}$ where w is 1 to 12 and $R_{21}$ is alkyl of 1 to 12 carbon atoms, $R_7$ and $R_8$ are independently hydrogen, alkyl of 1 to 18 carbon atoms, straight or branched chain $C_3$–$C_{18}$alkyl which is interrupted by —O—, —S— or —$NR_{11}$—, $C_5$–$C_{12}$cycloalkyl, $C_6$–$C_{14}$aryl or $C_1$–$C_3$hydroxylalkyl, or $R_7$ and $R_8$ together with the N atom are a pyrrolidine, piperidine, piperazine or morpholine ring, when n is 2, $R_5$ is a divalent radical —O—$R_9$—O— or —$N(R_{11})$—$R_{10}$—$N(R_{11})$—, $R_9$ is $C_2$–$C_8$alkylene, $C_4$–$C_8$alkenylene, $C_4$alkynylene, cyclohexylene, straight or branched chain $C_4$–$C_{10}$alkylene which is interrupted by —O— or by —$CH_2$—CHOH—$CH_2$—O—$R_{14}$—O—$CH_2$—CHOH—$CH_2$—, $R_{10}$ being straight or branched chain $C_2$–$C_{12}$alkylene which may be interrupted by —O—, cyclohexylene, or

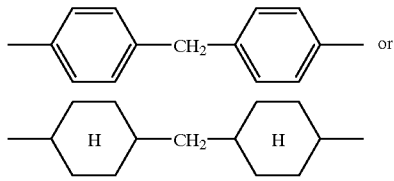

or $R_{10}$ and $R_{11}$ with the two nitrogen atoms form a piperazine ring, $R_{14}$ is straight or branched chain $C_2$–$C_8$alkylene, straight or branched chain $C_4$–$C_{10}$alkylene which is interrupted by —O—, cycloalkylene, arylene or

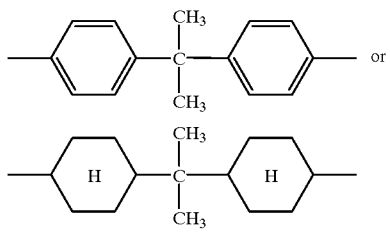

where $R_7$ and $R_8$ are independently hydrogen, alkyl of 1 to 18 carbon atoms or $R_7$ and $R_8$ together are alkylene of 4 to 6 carbon atoms, 3-oxapentamethylene, 3-iminopentamethylene or 3-methyliminopentamethylene, $R_{11}$ is hydrogen, straight or branched chain $C_1$–$C_{18}$alkyl, $C_5$–$C_{12}$cycloalkyl, straight or branched chain $C_3$–$C_8$alkenyl, $C_6$–$C_{14}$aryl or $C_7$–$C_{15}$aralkyl, $R_{12}$ is straight or branched chain $C_1$–$C_{18}$alkyl, straight or branched chain $C_3$–$C_{18}$alkenyl, $C_5$–$C_{10}$cycloalkyl, $C_6$–$C_{16}$aryl or $C_7$–$C_{15}$aralkyl, $R_{13}$ is H, straight chain or branched $C_1$–$C_{18}$alkyl which is substituted by —PO(O$R_{12}$)$_2$, phenyl which is unsubstituted or substituted by OH, $C_7$–$C_{15}$aralkyl or —$CH_2$O$R_{12}$, $R_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, L is alkylene of 1 to 12 carbon atoms, alkylidene of 2 to 12 carbon atoms, benzylidene, p-xylylene or cycloalkylidene, and T is —SO—, —$SO_2$—, —SO—E—SO—, —$SO_2$—E—$SO_2$—, —CO—, —CO—E—CO—, —COO—E—OCO—, —CO—$NG_3$—E—$NG_3$—CO— or —$NG_3$—CO—E—CO—$NG_3$—, where E is alkylene of 2 to 12 carbon atoms, cycloalkylene of 5 to 12 carbon atoms, or alkylene interrupted or terminated by cyclohexylene of 8 to 12 carbon atoms; and where usually at least one of the radicals $R_1$ and $R_2$ in formulae A or B are not hydrogen;

and/or a 2-hydroxyphenyltriazine of formulae P and/or Q

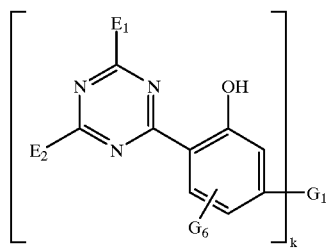

(P)

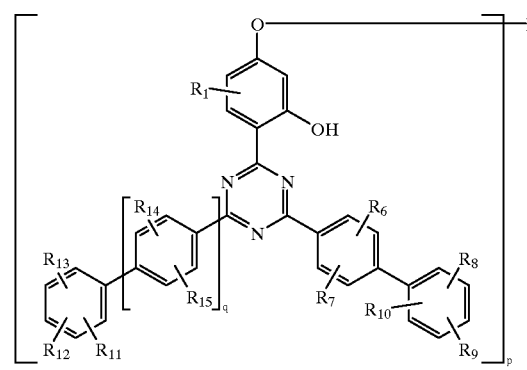

(Q)

wherein in formula P
$G_1$ is H or —OG;
k is 1 or 2; and if k=1
$E_1$ and $E_2$, independently, are a group of formula Fa or Fb

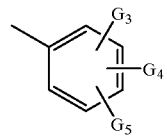

(Fa)

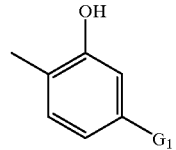

(Fb)

and

G is H or $C_1$–$C_{18}$-Alkyl; or $C_1$–$C_{18}$-Alkyl, which is substituted by OH, $C_1$–$C_{18}$alkoxy, $C_5$–$C_{12}$cycloalkoxy, allyloxy, halogen, =O, —COOH, —COO$G_8$, —CON$H_2$, —CONH$G_9$, —CON($G_9$)($G_{10}$), —N$H_2$, —NH$G_9$, =N$G_9$, —N($G_9$)($G_{10}$), —NHCO$G_{11}$, —CN, —OCO$G_{11}$, phenoxy and/or phenoxy, which is substituted by $C_1$–$C_{18}$alkyl, $C_1$–$C_{18}$alkoxy or halogen; or G is $C_3$–$C_{50}$alkyl, which is interrupted by —O— and may additionally be substituted by OH; or G is $C_3$–$C_6$alkenyl; glycidyl; $C_5$–$C_{12}$cycloalkyl; $C_5$–$C_{12}$cycloalkyl, which is substituted by OH, $C_1$–$C_4$alkyl or —OCO$G_{11}$; $C_7$–$C_{11}$phenylalkyl, which is unsubstituted or substituted by OH, Cl, $C_1$–$C_{18}$alkoxy or $C_1$–$C_{18}$alkyl; or is —CO—$G_{12}$ or —$SO_2$—$G_{13}$;

$G_3$, $G_4$ and $G_5$, independently, are H, $C_1$–$C_{12}$alkyl; $C_2$–$C_6$alkenyl; $C_1$–$C_{18}$alkoxy; $C_5$–$C_{12}$cycloalkoxy;

$C_2$–$C_{18}$alkenoxy; halogen; —C≡N; $C_1$–$C_4$haloalkyl; $C_7$–$C_{11}$phenylalkyl; —COOG$_8$; CONH$_2$; CONHG$_9$; CONG$_9$G$_{10}$; sulfone; $C_2$–$C_{18}$acylamino; OCOG$_{11}$; phenyloxy; or phenyloxy, $C_1$–$C_{12}$alkyl or $C_1$–$C_{18}$alkoxy, each of which is substituted by $C_1$–$C_{18}$alkyl, $C_1$–$C_{18}$alkoxy or halogen; and G$_3$ in formula Fa additionaly embraces —NG$_{16}$G$_{17}$;

G$_6$ has the meanings given for R$_1$ in formula Q below;

G$_8$ is $C_1$–$C_{18}$alkyl; $C_3$–$C_{18}$alkenyl; $C_3$–$C_{50}$alkyl, which is interrupted by O, NH, NG$_9$ or S and/or substituted by OH; —P(O)(OG$_{14}$)$_2$, —N(G$_9$)(G$_{10}$), —OCOG$_{11}$ and/or OH substituted $C_1$–$C_4$alkyl; glycidyl; $C_5$–$C_{12}$cycloalkyl; $C_1$–$C_4$alkylcyclohexyl; phenyl; $C_7$–$C_{14}$alkylphenyl; $C_6$–$C_{15}$bicycloalkyl; $C_6$–$C_{15}$bicycloalkenyl; $C_6$–$C_{15}$tricycloalkyl; $C_6$–$C_{15}$bicycloalkyl-alkyl; or $C_7$–$C_{11}$phenylalkyl;

G$_9$ and G$_{10}$ independently are $C_1$–$C_{12}$alkyl; $C_3$–$C_{12}$alkoxyalkyl; $C_2$–$C_{18}$alkanoyl; $C_4$–$C_{16}$dialkylaminoalkyl or $C_5$–$C_{12}$cycloalkyl; or G$_9$ and G$_{10}$ together are $C_3$–$C_9$alkylene or -oxaalkylene or -azaalkylene;

G$_{11}$ is $C_1$–$C_{18}$alkyl; $C_1$–$C_{12}$alkoxy; $C_2$–$C_{18}$alkenyl; $C_7$–$C_{11}$phenylalkyl; $C_7$–$C_{11}$phenylalkoxy; $C_6$–$C_{12}$cycloalkyl; $C_6$–$C_{12}$cycloalkoxy; phenoxy or phenyl; or $C_3$–$C_{50}$alkyl, which is interrupted by —O— and may be substituted by OH;

G$_{12}$ is $C_1$–$C_{18}$alkyl; $C_2$–$C_{18}$alkenyl; phenyl; $C_1$–$C_{18}$alkoxy; $C_3$–$C_{18}$alkenyloxy; $C_3$–$C_{50}$alkoxy, which is interrupted by O, NH, NG$_9$ or S and/or substituted by OH; cyclohexyloxy; phenoxy; $C_7$–$C_{14}$alkylphenoxy; $C_7$–$C_{11}$phenylalkoxy; $C_1$–$C_{12}$alkylamino; phenylamino; tolylamino or naphthylamino;

G$_{13}$ is $C_1$–$C_{12}$alkyl; phenyl; naphthyl or $C_7$–$C_{14}$alkylphenyl;

G$_{14}$ is $C_1$–$C_{12}$alkyl, methylphenyl or phenyl;

G$_{16}$ is H or $C_1$–$C_{20}$alkyl;

G$_{17}$ is H, $C_1$–$C_{20}$alkyl, $C_7$–$C_{13}$phenylalkyl, —C(=O)—G$_{19}$, —C(=O)—NH—G$_{16}$; and G$_{19}$ is $C_1$–$C_{20}$alkyl; $C_2$–$C_{20}$alkyl, which is interrupted by 1 to 6 oxygen atoms and/or substituted by OH, halogen, NH$_2$, NHG$_9$ or NG$_9$G$_{10}$; $C_1$–$C_{20}$alkoxy; phenyl; $C_7$–$C_{13}$phenylalkyl or $C_2$–$C_{20}$alkenyl;

and if k is 2

E$_1$ and E$_2$ are a group of formula Fa;

G is $C_2$–$C_{16}$alkylene, $C_4$–$C_{12}$alkenylene, xylylene, O interrupted and/or OH substituted $C_3$–$C_{20}$alkylene, or a group of one of the formulae —CH$_2$CH(OH)CH$_2$O—G$_{20}$—OCH$_2$CH(OH)CH$_2$—, —CO—G$_{21}$—CO—, —CO—NH—G$_{22}$—NH—CO—, —(CH$_2$)$_j$—COO—G$_{20}$—OOC—(CH$_2$)$_j$—, wherein j is a number from the range 1 to 3, or

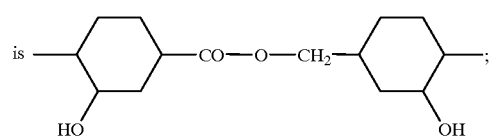

G$_{20}$ is $C_2$–$C_{10}$alkylene; $C_4$–$C_{50}$alkylene which is interrupted by O, phenylene, or a group -phenylene-E-phenylene-, wherein E is —O—, —S—, —SO$_2$—, —CH$_2$—, —CO—, or —C(CH$_3$)$_2$—;

G$_{21}$ is $C_2$–$C_{10}$alkylen, $C_2$–$C_{10}$oxaalkylen, $C_2$–$C_{10}$thiaalkylen, $C_6$–$C_{12}$arylen or $C_2$–$C_6$alkenylen;

G$_{22}$ is $C_2$–$C_{10}$alkylene, phenylene, tolylene, diphenylenmethane or a group

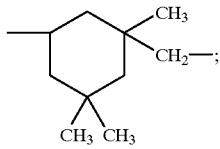

and all other residues have the meanings given for k=1;
and wherein in formula Q R$_1$ is H; $C_1$–$C_{24}$alkyl or $C_5$–$C_{12}$cycloalkyl; or $C_1$–$C_{24}$alkyl or $C_5$–$C_{12}$cycloalkyl, each of which is substituted by 1 to 9 halogen, —R$_4$, —OR$_5$, —N(R$_5$)$_2$, =NR$_5$, =O, —CON(R$_5$)$_2$, —COR$_5$, —COOR$_5$, —OCOR$_5$, —OCON(R$_5$)$_2$, —CN, —NO$_2$, —SR$_5$, —SOR$_5$, —SO$_2$R$_5$, —P(O)(OR$_5$)$_2$, morpholinyl-, piperidinyl-, 2,2,6,6-tetramethylpiperidinyl-, piperazinyl- or N-methylpiperazinyl- or combinations thereof; or is $C_1$–$C_{24}$alkyl or $C_5$–$C_{12}$cycloalkyl, each of which is interrupted by 1 to 6 phenylene-, —O—, —NR$_5$—, —CONR$_5$—, —COO—, —OCO—, —CH(R$_5$)—, —C(R$_5$)$_2$— or —CO— or combinations thereof; or R$_1$ is $C_2$–$C_{24}$alkenyl; halogen; —SR$_3$, SOR$_3$; SO$_2$R$_3$; —SO$_3$H; or SO$_3$M;

R$_3$ is $C_1$–$C_{20}$alkyl; $C_3$–$C_{18}$alkenyl; $C_5$–$C_{12}$cycloalkyl; $C_7$–$C_{15}$phenylalkyl, unsubstituted or by 1 to 3 $C_1$–$C_4$alkyl substituted $C_6$–$C_{12}$aryl;

R$_4$ is unsubstituted $C_6$–$C_{12}$aryl; or $C_6$–$C_{12}$aryl substituted by 1 to 3 halogen, $C_1$–$C_8$alkyl or $C_1$–$C_8$alkoxy or combinations thereof; $C_5$–$C_{12}$cycloalkyl; unsubstituted $C_7$–$C_{15}$phenylalkyl; or $C_7$–$C_{15}$phenylalkyl substituted on the phenyl ring by 1 to 3 halogen, $C_1$–$C_8$alkyl, $C_1$–$C_8$alkoxy or combinations thereof; or $C_2$–$C_8$alkenyl;

R$_5$ is R$_4$; H; $C_1$–$C_{24}$alkyl; or a radical of the formula

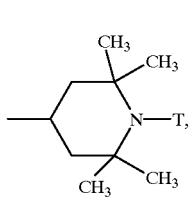

(1a)

wherein

T is H; $C_1$–$C_8$alkyl; $C_2$–$C_8$alkyl substituted by one or more hydroxy or acyloxy; oxyl; hydroxy; —CH$_2$CN; $C_1$–$C_{18}$alkoxy; $C_5$–$C_{12}$cycloalkoxy; $C_3$–$C_6$alkenyl; $C_7$–$C_9$phenylalkyl; $C_7$–$C_9$phenylalkyl substituted on the phenyl ring by 1–3 $C_1$–$C_4$alkyl; or is aliphatic $C_1$–$C_8$alkanoyl;

R$_6$, R$_7$, R$_8$, R$_9$, R$_{10}$, R$_{11}$, R$_{12}$, R$_{13}$, R$_{14}$ and R$_{15}$, independently, are H; hydroxy; —C≡N; $C_1$–$C_{20}$alkyl; $C_1$–$C_{20}$alkoxy; $C_7$–$C_{20}$phenylalkyl; $C_4$–$C_{12}$cycloalkyl; $C_4$–$C_{12}$cycloalkoxy; halogen; halo-$C_1$–$C_5$-alkyl; sulfonyl; carboxyl; acylamino; acyloxy; $C_1$–$C_{12}$alkoxycarbonyl; aminocarbonyl; —O—Y; or O—Z; or R$_8$ and R$_9$ together with the phenyl radical they are bound to form a carbocyclic residue which is interrupted by one or more O or N; and R$_{11}$ if q is 0, additionally embraces —NG$_{16}$G$_{17}$, where G$_{16}$ and G$_{17}$ are as defined above;

M is alkaline metal;
p is 1 or 2;
q is 0 or 1;
and if p is 1
X, Y and Z, independently, are $R_y$; $R_x$ substituted $C_1$–$C_{24}$alkyl; $C_2$–$C_{50}$alkyl interrupted by one or more oxygen atoms and substituted by one or more OH and/or $R_x$; $C_4$–$C_{12}$cycloalkyl substituted by $R_x$ or —$OR_y$; $C_4$–$C_{20}$alkenyl interrupted by one or more oxygen atoms; or a group of one of the formulae —CH(($CH_2$)$_n$—$R_2$)—CO—O—($CH_2$)$_m$—$R'_2$; —CH(($CH_2$)$_n$—$R_2$)—CO—(NR')—($CH_2$)$_m$—$R'_2$;

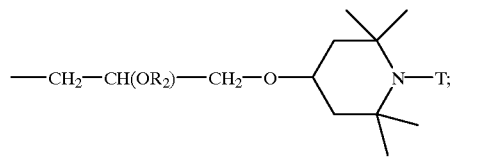

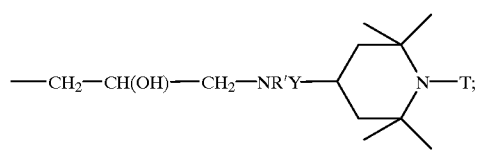

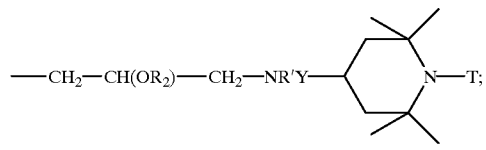

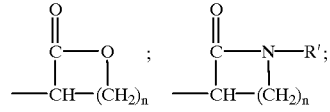

—CO—($CH_2$)$_n$—$R_2$; —CO—O—($CH_2$)$_n$—$R_2$; —$CH_2$—CH(—O—(CO)—$R_2$)—$R'_2$; —CO—NR'—($CH_2$)$_n$—$R_2$;

$R_2$ and $R'_2$, independently, if bound to a carbon atom, are $R_x$; and if bound to another atom than carbon, are $R_y$;
n is 0 to 20; and
m is 0 to 20; and
if p is 2,
Y and Z, independently, have the same meanings as defined for p=1; and
X is $C_2$–$C_{12}$alkylene; —CO-($C_2$–$C_{12}$alkylene)-CO—; —CO-phenylene-CO—; CO-biphenylene-CO—; CO—O-($C_2$–$C_{12}$alkylene)-O—CO—; —CO—O-phenylene-O—CO—; —CO—O-biphenylene-O—CO—; —CO—NR'-($C_2$–$C_{12}$alkylene)-NR'—CO—; —CO—NR'-phenylene-NR'—CO—; —CO—NR'-biphenylene-NR'—CO—; —$CH_2$—CH(OH)—$CH_2$—; —$CH_2$—CH($OR_2$)—$CH_2$—; —$CH_2$—CH(OH)—$CH_2$—O—D—O—$CH_2$—CH(OH)—$CH_2$; —CH(($CH_2$)$_n$$R_2$)—COO—D—OOC—CH(($CH_2$)$_n$$R_2$)—; —$CH_2$—CH($OR_2$)—$CH_2$—O—D—O—$CH_2$—CH($OR_2$)—$CH_2$— ist;
D is $C_2$–$C_{12}$alkylene; $C_4$–$C_{50}$alkylene interrupted by one or more oxygen atoms; phenylene; biphenylene or phenylene-E-phenylene;
E is —O—; —S—; —$SO_2$—; —$CH_2$—; —CO—; or —C($CH_3$)$_2$—;
$R_x$ is H; hydroxy; $C_1$–$C_{20}$alkyl; $C_4$–$C_{12}$cycloalkyl; $C_1$–$C_{20}$alkoxy; $C_4$–$C_{12}$cycloalkoxy; $C_4$–$C_{12}$cycloalkyl or $C_4$–$C_{12}$cycloalkyloxy, each of which is interrupted by one or more oxygen atoms; $C_6$–$C_{12}$aryl; hetero-$C_3$–$C_{12}$aryl; —$OR_z$; $NHR_z$; $R_z$; CONR'R"; allyl; $C_2$–$C_{20}$alkenyl; $C_4$–$C_{12}$cycloalkenyl; $C_4$–$C_{12}$cycloalkenyl interrupted by one or more oxygen atoms; $C_3$–$C_{20}$alkinyl; or $C_6$–$C_{12}$cycloalkinyl; or $C_1$–$C_{20}$alkyl, $C_2$–$C_{20}$alkoxy or $C_4$–$C_{12}$cycloalkyl, each of which is substituted by hydroxy, —$NH_2$, —NH—$C_1$–$C_8$alkyl, —NH-cyclohexyl, —N($C_1$–$C_8$alkyl)$_2$, dicyclohexylamino, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkinyl, $C_6$–$C_{12}$cycloalkinyl, $C_6$–$C_{12}$aryl, acylamin, acyloxy, sulfonyl, carboxyl, (meth)acryloxy, (meth)acrylamino,

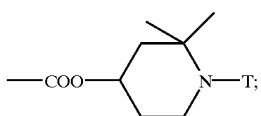

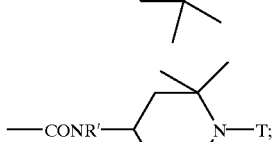

$R_y$ is H; $C_1$–$C_{20}$alkyl; $C_4$–$C_{12}$cycloalkyl; $C_4$–$C_{12}$cycloalkyl interrupted by one or more oxygen atoms; $C_6$–$C_{12}$aryl; hetero-$C_3$–$C_{12}$aryl; $R_z$; allyl; $C_2$–$C_{20}$alkenyl; $C_4$–$C_{12}$cycloalkenyl; $C_4$–$C_{12}$cycloalkenyl interrupted by one or more oxygen atoms; $C_3$–$C_{20}$alkinyl; or $C_6$–$C_{12}$cycloalkinyl; or $C_1$–$C_{20}$alkyl or $C_4$–$C_{12}$cycloalkyl, each of which is substituted by hydroxy, —$NH_2$, —NH—$C_1$–$C_8$alkyl, —NHcyclohexyl, —N($C_1$–$C_8$alkyl)$_2$, dicyclohexylamino, halogen, $C_1$–$C_{20}$alkyl, $C_1$–$C_{20}$alkoxy, $C_4$–$C_{12}$cycloalkyl, $C_4$–$C_{12}$cycloalkoxy, $C_2$–$C_{20}$alkenyl, $C_4$–$C_{12}$cycloalkyl, $C_3$–$C_{20}$alkinyl, $C_6$–$C_{12}$cycloalkinyl, $C_6$–$C_{12}$aryl, acylamin, acyloxy, sulfonyl, carboxyl, (meth)acryloxy, (meth)acrylamino,

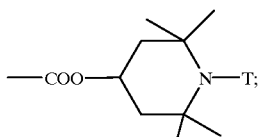

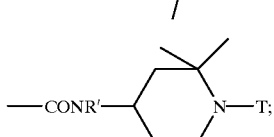

$R_z$ is —COR'; —COOR'; —CONR'R"; —CO—CH=$CH_2$; —CO—C($CH_3$)=$CH_2$; R' and R", independently, are H; $C_1$–$C_{20}$alkyl; $C_4$–$C_{50}$alkyl interrupted by one or more oxygen atoms; $C_4$–$C_{12}$cycloalkyl; $C_4$–$C_{12}$cycloalkyl interrupted by one or more oxygen atoms; $C_2$–$C_{20}$alkenyl; $C_4$–$C_{20}$-Alkenyl interrupted by one or more oxygen atoms; or are $C_6$–$C_{12}$aryl; or $C_1$–$C_{20}$alkyl or $C_4$–$C_{12}$cycloalkyl, each of which is substituted by hydroxy, —$NH_2$, —NH—$C_1$-$C_8$alkyl, —NHcyclohexyl, —N($C_1$-$C_8$alkyl)$_2$, dicyclohexylamino, halogen, $C_1$-$C_{20}$alkyl, $C_1$-$C_{20}$alkoxy, $C_4$-$C_{12}$cycloalkyl, $C_4$-$C_{12}$cycloalkoxy, $C_2$-$C_{20}$alkenyl, $C_4$-$C_{12}$cycloalkyl, $C_3$-$C_{20}$alkinyl, $C_6$-$C_{12}$cycloalkinyl, $C_6$-$C_{12}$aryl, acylamin, acyloxy, sulfonyl, carboxyl, (meth)acryloxy, (meth)acrylamino,

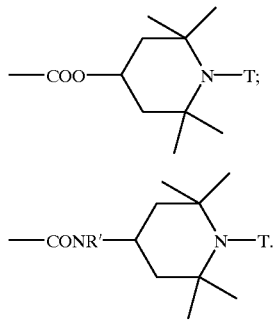

Examples for a benzotriazole of formula K, L, M or N are listed above under item 2.1; examples for a 2-hydroxyphenyltriazine of formulae P and/or Q are listed above under item 2.8.

Likewise of particular interest is the use of the novel mixtures comprising compounds of the formula F as stabilizers for coatings, for example for paints. The invention therefore also relates to those compositions whose component (A) is a film-forming binder for coatings.

The novel coating composition preferably comprises 0.01–10 parts by weight of (B), in particular 0.05–10 parts by weight of (B), especially 0.1–5 parts by weight of (B), per 100 parts by weight of solid binder (A).

Multilayer systems are possible here as well, where the concentration of the novel stabilizer (component (B)) in the outer layer can be relatively high, for example from 1 to 15 parts by weight of (B), in particular 3–10 parts by weight of (B), per 100 parts by weight of solid binder (A).

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates.

The binder (component (A)) can in principle be any binder which is customary in industry, for example those described in Ullmann's Encyclopedia of Industrial Chemistry, 5th Edition, Vol. A18, pp. 368–426, VCH, Weinheim 1991. In general, it is a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component (A) can be a cold-curable or hot-curable binder; the addition of a curing catalyst may be advantageous. Suitable catalysts which accelerate curing of the binder are described, for example, in Ullmann's Encyclopedia of Industrial Chemistry, Vol. A18, p.469, VCH Verlagsgesellschaft, Weinheim 1991.

Preference is given to coating compositions in which component (A) is a binder comprising a functional acrylate resin and a crosslinking agent.

Examples of coating compositions containing specific binders are:

1. paints based on cold- or hot-crosslinkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking, if desired with addition of a melamine resin;
4. one-component polyurethane paints based on a Tris-alkoxycarbonyltriazine crosslinker and a hydroxyl group containing resin such as acrylate, polyester or polyether resins;
5. one-component polyurethane paints based on aliphatic or aromatic urethaneacrylates or polyurethaneacrylates having free amino groups within the urethane strukture and melamine resins or polyether resins, if necessary with curing catalyst;
6. two-component paints based on (poly)ketimines and aliphatic or aromatic isocyanates, isocyanurates or polyisocyanates;
7. two-component paints based on (poly)ketimines and an unsaturated acrylate resin or a polyacetoacetate resin or a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and acrylate resins containing anhydride groups, or unsaturated acrylate resins, or aliphatic or aromatic isocyanates, isocyanurates or polyisocyanates;
12. two-component paints based on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins.

In addition to components (A) and (B), the coating composition according to the invention preferably comprises as component (C) a light stabilizer of the sterically hindered amine type, the 2-(2-hydroxyphenyl)-1,3,5-triazine and/or 2-hydroxyphenyl-2H-benzotriazole type, for example as mentioned in the above list in sections 2.1, 2.6 and 2.8. Further examples for light stabilizers of the 2-(2-hydroxyphenyl)-1,3,5-triazine type advantageously to be added can be found e.g. in the publications U.S. Pat. No. 4,619,956, EP-A-434608, U.S. Pat. No. 5,198,498, U.S. Pat. No. 5,322,868, U.S. Pat. No. 5,369,140, U.S. Pat. No. 5,298,067, WO-94/18278, EP-A-704437, GB-A-2297091, WO-96/28431. Of special technical interest is the addition of the 2-(2-hydroxyphenyl)-1,3,5-triazines and/or 2-hydroxyphenyl-2H-benzotriazoles, especially the 2-(2-hydroxyphenyl)-1,3,5-triazines.

To achieve maximum light stability, it is of particular interest to add sterically hindered amines as set out in the abovementioned list under 2.6. The invention therefore also relates to a coating composition which in addition to components (A) and (B) comprises as component (C) a light stabilizer of the sterically hindered amine type.

This stabilizer is preferably a 2,2,6,6-tetraalkylpiperidine derivative containing at least one group of the formula

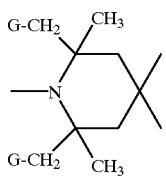

in which G is hydrogen or methyl, especially hydrogen.

Component (C) is preferably used in an amount of 0.05–5 parts by weight per 100 parts by weight of the solid binder.

Examples of tetraalkylpiperidine derivatives which can be used as component (C) are given in EP-A-356 677, pages 3–17, sections a) to f). These sections of this EP-A are regarded as part of the present description. It is particular expedient to employ the following tetraalkylpiperidine derivatives:

bis(2,2,6,6-tetramethylpiperid-4-yl)succinate,
bis(2,2,6,6-tetramethylpiperid-4-yl)sebacate,
bis(1,2,2,6,6-pentamethylpiperid-4-yl)sebacate,
di(1,2,2,6,6-pentamethylpiperid-4-yl)butyl-(3,5-di-tert-butyl-4-hydroxybenzyl)malonate,
bis(1-octyloxy-2,2,6,6-tetramethylpiperid-4-yl)sebacate,
tetra(2,2,6,6-tetramethylpiperid-4-yl)butane-1,2,3,4-tetracarboxylate,
tetra(1,2,2,6,6-pentamethylpiperid-4-yl)butane-1,2,3,4-tetracarboxylate,
2,2,4,4-tetramethyl-7-oxa-3,20-diaza-21-oxo-dispiro [5.1.11.2]heneicosane,
8-acetyl-3-dodecyl-1,3,8-triaza-7,7,9,9-tetramethylspiro [4.5]decane-2,4-dione,
1,1-bis-(1,2,2,6,6-pentamethylpiperidine-4-yl-oxycarbonyl)-2-(4-methoxyphenyl)-ethene, or a compound of the formulae

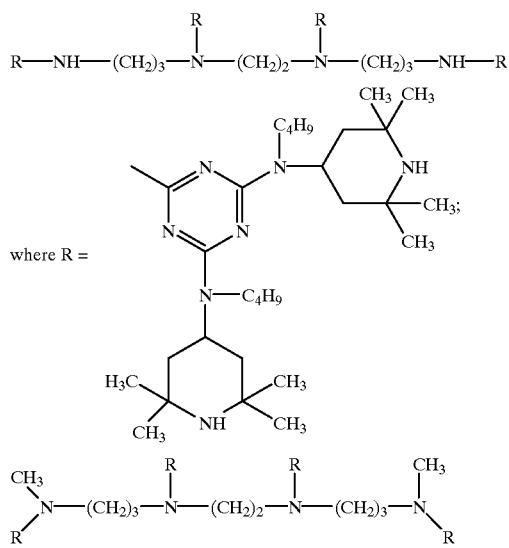

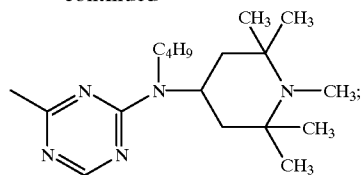

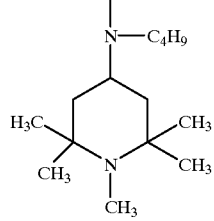

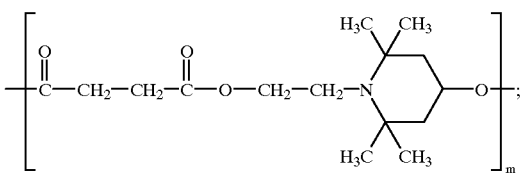

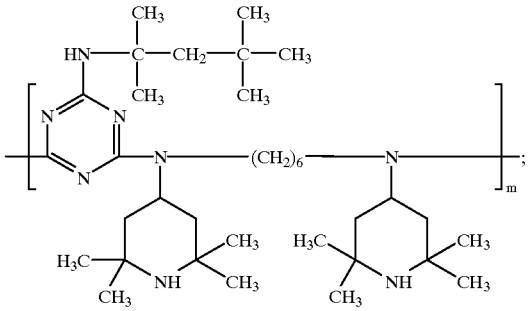

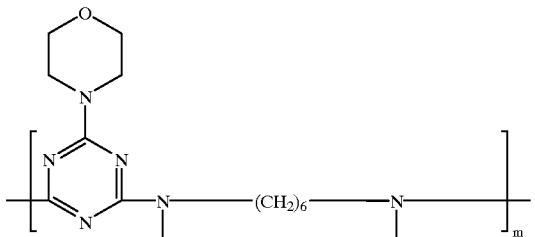

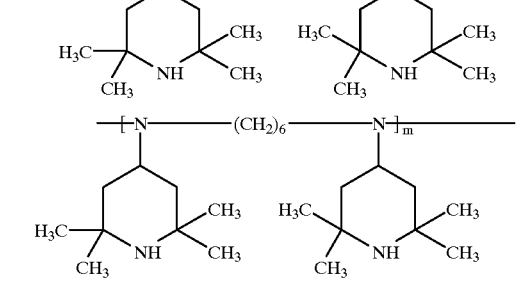

in which m is 5–50.

Apart from components (A), (B) and, if used, (C), the coating composition can also comprise further components, examples being solvents, pigments, dyes, plasticizers, stabilizers, thixotropic agents, drying catalysts and/or levelling agents. Examples of possible components are those described in Ullmann's Encyclopedia of Industrial Chemistry, 5th Edition, Vol. A18, pp. 429–471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalyst used can also be a phosphine, for example triphenylphosphine.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation-curable coating compositions, the novel stabilizers can also be employed without the addition of sterically hindered amines.

The coating compositions according to the invention can be applied to any desired substrates, for example to metal, wood, plastic or ceramic materials. They are preferably used as topcoat in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. The coatings are preferably cured at 50–150° C., and in the case of powder coatings or coil coatings even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formula F according to the invention. The paint is preferably a topcoat for automobiles. The invention furthermore relates to a process for stabilizing a coating based on organic polymers against damage by light, oxygen and/or heat, which comprises mixing with the coating composition a mixture comprising a compound of the formula F, and to the use of mixtures comprising a compound of the formula F in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition may be a high-solids paint or can be solvent-free (e.g. a powder coating material). Powder coatings are, for example, those described in Ullmann's Encyclopedia of Industrial Chemistry, 5th Ed., A18, pages 438–444. The additive of present invention can be used therein e.g. as described e.g. in EP-A-856563, especially page 22, line 21, until page 26, line 29, and literature cited in this reference.The powder coating material may also have the form of a powder-slurry (dispersion of the powder preferably in water).

Examples of resins for powder coatings are:
1. Carboxy- or hydroxy-functionalised polyester resins, based on monomers such as terephthalic acid, isophthalic acid, neopentyl glycol, 2-methyl-1,3-propandiol, tris-1,1,1-(hydroxymethyl)propane etc.
2. Epoxy resins based on bisphenols, such as bisphenol A or Novolac® epoxy resins for thermal or uv-cure with cationic photoinitiators.
3. Hydroxy-, carboxy- or glycidyl-functionalised acrylate polymers and copolymers. Suitable comonomers include styrene, alkyl methacrylates, acrylamide, acrylonitrile etc.
4. Unsaturated polyester resins for uv-cureable powder coatings, typically used in conjunction with multifuntional vinyl ethers or acrylate esters.

Powder coating based on resins with carboxy functionality are typically used together with crosslinking agents of the following classes:
1) polyfunctional epoxy compounds, such as epoxy resins, triglycidylisocyanurate, epoxidised unsaturated fatty acid esters (such as Uranox® resins from DSM), and esters and ethers of glycidol (such as Araldit® PT910 from Ciba Specialty Chemicals).
2) β-hydroxyalkylamides, such as Primid® types XL552 and QM1260 from Ems Chemie.
3) derivatives of melamine, benzoguanimine and glycoluril, such as Powderlink® 1174 from American Cyanamid.

Crosslinking agents for resins of hydroxy functionality include anhydrides and especially blocked diisocyanates and uretdiones, etc.

Powder coatings based on resins with epoxy functionality are typically used together with crosslinking agents such as diacids (such as 1,12-dodecanedioic acid), carboxy-functional polyesters, carboxy-functional copolymers of acrylates and methacrylates, anhydrides (such as the anhydride prepared from 1,12-dodecanedioic acid).

Other additives that can be used together with the compounds of the invention in powder coatings include: degassing agents, flow promoters, tribocharging additives cure catalysts, sensitisers, cationic and free-radical photoinitiators, as well as typical liquid paint additives.

A particular advantage of the compounds of the invention is their low basicity, as basic compounds often catalyse the crosslinking reactions of powder coatings to cause poor flow and degassing, and reduced storage stability. This is particularly useful in formulations of high reactivity, such as the glycidylmethacrylate-functionalised acrylics. Here, the combination of the compounds of the invention together with uv-absorbers, especially of the hydroxyphenyltriazine class, can be used to improve the weatherability without causing catalysis. In other binder systems and with other classes of uv-absorbers, such as those previously mentioned to be of particular use in automotive paints, synergistic effects on the weatherability are also found.

In powder coatings the compounds of the invention can also be used to improve the oxidative stability and reduce yellowing on curing and overbaking. Here not only is the low basicity advantageous, but also the ability of the hindered morpholinones to withstand and prevent yellowing caused by oxides of nitrogen in gas-fired ovens. Use together particularly with phosphite and phosphonite costabilisers, as disclosed in EP-A-816442, and dialkylesters of dithiopropionic acid is particularly beneficial. The compounds of the invention can, where appropriate also be used to stabilise polyester during manufacture as well as at all stages of its subsequent use.

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

The examples below illustrate the invention further. All parts or percentages, in the examples as in the remainder of the description and in the claims, are by weight, unless stated otherwise. Whenever room temperature is mentioned, this denotes a temperature in the range 20–25° C. In the examples, the following abbreviations are used:

| | |
|---|---|
| % w/w | percent by weight; |
| m.p. | melting point or range; |
| mmHg | torr; 1 torr is 133.322 Pa; |
| NMR | nuclear magnetic resonance (of ¹H, if not otherwise indicated); |
| THF | tetrahydrofuran; |
| DMSO | dimethylsulfoxide. |

A: PREPARATION EXAMPLES

Example A1

5-Hydroxymethyl-3,3,5-trimethyl-2-morpholinone
(U.S. Pat. No. 4,528,370, Example 7E)

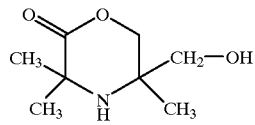

To a solution of 126.2 g (1.2 moles) of 2-amino-2-methyl-1,3-propanediol in 214.9 g (1.8 moles) of chloroform and 696 g (12 moles) of acetone, cooled to 0° C.÷5° C., 240 g (6 moles) of ground sodium hydroxide are added.

After the addition, the mixture is maintained under stirring at room temperature overnight. The solid is then filtered and suspended in a solution of 131.8 ml (1.6 moles) of HCl 37.27% (% w/w) in 400 ml of water.

The suspension is heated to reflux for 2 hours, filtered and concentrated in vacuo (90° C./10 mbar). The residue is taken up with 300 ml of toluene and the mixture heated to reflux being the residual water distilled off by azeotropation.

The organic solution is then added with 121.2 g (1.2 moles) of triethylamine and heated to reflux for 2 hours.

After cooling to room temperature, the mixture is filtered and the organic solution is concentrated in vacuo (60° C./10 mbar). The oil residue is distilled at 160° C./0.5 mbar giving an oil product.

NMR Analysis (300 MHz, CDCl₃, δ (ppm): 1.00 (s, 3H), 1.26 (s, 3H), 1.29 (s, 3H), 3.24 (s, 2H), 4.05 (d, 1H), 4.35 (d, 1H)

Example A2

Preparation of N-(2-hydroxyethyl)-3,3,5,5-tetramethyl-2-morpholinone

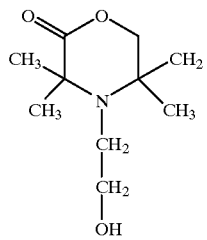

45.0 g (0.29 moles) of 3,3,5,5-tetramethyl-2-morpholone are dissolved in 450 ml of methanol. The solution is poured into an autoclave, added with 1 ml of concentrated HCl (37%) (% w/w) and pressurized with ethylene oxide (2 bars).

The solution is maintained at 120° C. under stirring for 12 hours and for further 48 hours at 130° C.

The mixture is then cooled to room temperature purged with nitrogen and evaporated in vacuo (60° C./10 mbar). A white solid product is obtained with m.p.: 114° C.

Example A3

Preparation of 5-hydroxymethyl-3,3,4,5-tetramethyl-2-morpholinone.

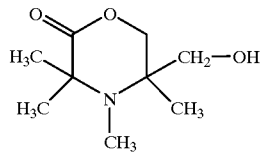

12.5 g (72 mmoles) of the product from Example A1 are dissolved in 100 ml of tert-amyl alcohol and added with 6.5 g (210 mmoles) of paraformaldehyde and 3.9 g (866 mmoles) of formic acid.

The mixture is then heated to reflux and maintained at reflux for 12 hours.

The mixture is then cooled to room temperature, added with a solution of 12 g (866 mmoles) of potassium carbonate in 30 ml of water, stirred for 1 hour and the organic phase separated. The organic phase is then evaporated in vacuo (70° C./14 mbar). The oil residue is then destilled at 165–168° C./0.4 mbar giving an oil product.

NMR Analysis (300 Mhz, CDCl$_3$, δ (ppm)): 1.03 (s, 3H), 1.41 (s, 3H), 1.42 (s, 3H), 2.27 (s, 3H), 3.25 (d, 1H), 3.60 (d, 1H), 4.05 (d, 1H), 4.35 (d, 1H)

Example A4

Preparation of the Compound of the Formula

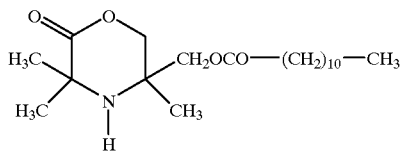

20 g (116 mmoles) of the product from Example A1 is dissolved in 300 ml of xylene, added with 24.7 g (116 mmoles) of dodecanoic acid methyl ester and with 0.1 g of dibutyltin(IV)oxide.

The mixture is heated to reflux and maintained at reflux for 16 hours being the methanol formed during the reaction distilled off by azeotropation.

The mixture is then concentrated to 150 ml, 150 ml of xylene being distilled off.

The mixture is then cooled to room temperature, washed with water, dried, filtered and evaporated in vacuo (60° C./10 mbar). The initial oil product obtained, NMR analysis (300 Mhz) conforming with the expected structure, slowly crystallizes showing a melting point of 24° C.

Example A5

Preparation of the Compound of the Formula

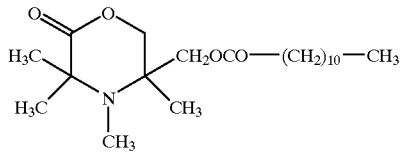

Following the procedure described in example A4, 8.0 g (43 mmoles) of the product from example A3 are reacted with 9.6 g (47 mmoles) of dodecanoic acid methylester and with 0.1 g of dibutyltin(IV)oxide in 100 ml of xylene. An oil product is obtained; $^1$H-NMR analysis (300 MHz, CDCl3, δ (ppm)): 0.85 (t, 3H), 1.08 (s, 3H), 1.22 (broad signal, 16H), 1.36 (s, 3H), 1.39 (s, 3H), 1.58 (m, 2H), 2.25 (t, 2H), 2.32 (s, 3H), 3.95 (d, 1H), 4.15 (m, 2H), 4.35 (d, 1H).

Example A6

Preparation of the Compound of the Formula

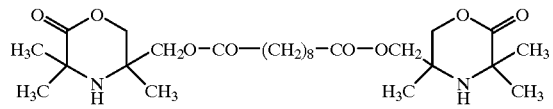

Following the procedure described in example A4, 50.0 g (289 mmoles) of the product from example A1 are reacted with 29.9 g (130 mmoles) of sebacic acid dimethylester in 200 ml of xylene in the presence of 0.25 g of dibutyltin(IV) oxide. The initial oil product obtained, NMR analysis (300 Mhz) conforming with the expected structure, slowly crystallizes: m.p. 45° C.

Example A7

Preparation of the Compound of the Formula

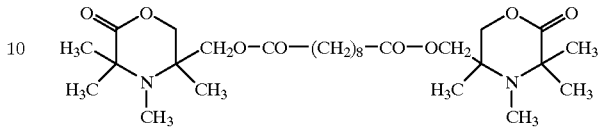

Following the procedure described in example A4, 15.7 g (85 mmoles) of the product from example A3 are reacted with 9.2 g (40 mmoles) of sebacic acid dimethylester in 100 ml of xylene and in the presence of 0.15 g of dibutyltin(IV) oxide. An oil product is obtained. $^1$H-NMR analysis (300 MHz, CDCl3, δ (ppm)): 1.03 (s, 3H), 1.22 (broad signal, 8H), 1.34 (s, 6H), 1.37 (s, 6H), 1.60 (m, 4H), 2.23 (t, 4H), 2.28 (s, 6H), 3.90 (d, 2H), 4.00 (d, 2H), 4.05 (d, 2H), 4.17 (d, 2H).

Example A8

Preparation of the Compound of the Formula

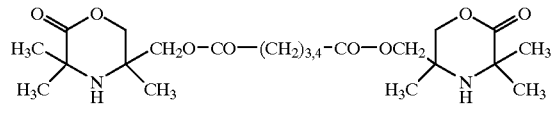

Following the procedure described in example A4, 35.0 g (202 mmoles) of the product from example A1 are reacted with 14.9 g (91 mmoles) of DBE-2® (a mixture 3:1 of glutaric acid dimethylester: adipic acid dimethyl ester, from Dupont-USA) in 150 ml of xylene and in the presence of 0.25 g of dibutyltin(IV)oxide. The initial oil product slowly crystallizes: m.p. 35° C.

Example A9

Preparation of the Compound of the Formula

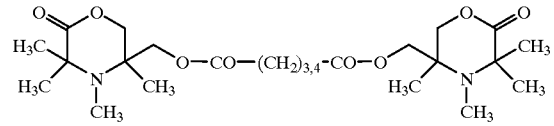

Following the procedure described in example A4, 37.3 g (202 mmoles) of the product from example A3 are reacted with 14.9 g (91 mmoles) of DBE-2® (a mixture 3:1 of glutaric acid dimethyl ester: adipic acid dimethylester, from Dupont-USA) in 150 ml of xylene and in the presence of 0.25 g of dibutyltin(IV)oxide. An oil product is obtained whose $^1$H and $^{13}$C NMR analysis conforms with the expected structure.

1H NMR Analysis (300 MHz, CDCl3, δ (ppm)): 1.01 (s, 6H), 1.3 (s, 6H), 1.35 (s, 6H), 2.31 (t, 4H), 2.29 (s, 3H).

Example A10

Preparation of the Compound of the Formula

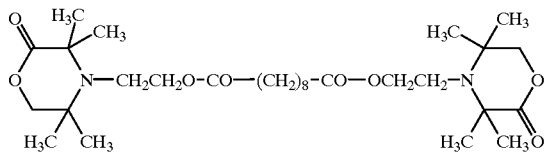

Following the procedure described in example A4, 12 g (69 mmoles) of the product from example A2 are reacted with 6.2 g (27 mmoles) of sebacic acid dimethyl ester in 100 ml of xylene and in the presence of 0.2 g of lithium amide. An oil product ist obtained whose $^1$H NMR (300 MHz, CDCl3) analysis conforms with the expected structure (δ (ppm)): 1.07 (s, 12H), 1.25 (broad signal, 8H), 1.37 (s, 12H), 1.60 (m, 4H), 2.20 (t, 4H), 2.75 (t, 4H), 3.90 (t, 4H), 3.94 (t, 4H).

Example A11

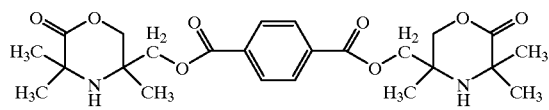

Following the procedure described in example A4, 19.0 g (0.11 mol) of the product from example A1 are reacted with 9.7 g (0.05 mol) of dimethylterephthalate in presence of 0.5 g dibutyltin(IV)oxide in 300 ml of xylene. The above compound crystallizes from the reaction mixture, m.p. 179–186° C. $^1$H-NMR analysis (300 MHz) conforms with the expected structure.

Example A12

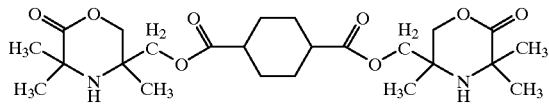

Following the procedure described in example A11 but replacing dimethylterephthalate by cyclohexane-1,4-dicarboxylic acid dimethylester leads to the above compound, m.p. 140–152° C. $^1$H-NMR analysis (300 MHz) conforms with the expected structure.

Example A13
a) Preparation of the Intermediate of Formula

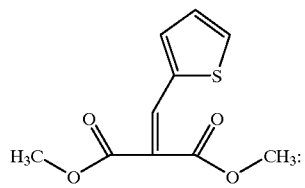

A mixture of 80.0 g (0.71 mol) of 2-thiophenecarboxaldehyde and 141.4 g (1.07 mol) of dimethylmalonate, 5.2 g (0.04 mol) benzoic acid and 22 g (0.26 mol) piperidine in 360 ml of toluene are heated to reflux for a period of 4 hours, water being distilled off by azeotropation. After cooling to room temperature, 10.0 g of $K_2CO_3$ are added, the mixture is filtered and the filtrate distilled at 119–121° C. at 0.5 mmHg.

b)

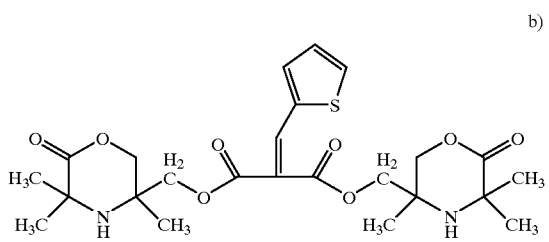

Following the procedure described in example A4, 31.2 g (0.18 mol) of the product from example A1 are reacted with 18.5 g (0.082 mol) of the product of part a) of this example in presence of 0.5 g dibutyltin(IV)oxide in 300 ml of xylene. Workup as described in example A4 leads to the above product. $^1$H-NMR analysis (300 MHz, CDCl$_3$) conforms with the expected structure (δ/ppm): 1.18–1.2 (2s, 6H); 1.3–1.4 (4s, 12H); 4.0–4.3 (m, 8H); 7.0–7.4 (m, 3H); 7.87 (s, 1H).

Example A14

3-Methyl-3-ethyl-5-hydroxymethyl-5-ethyl-2-morpholinone

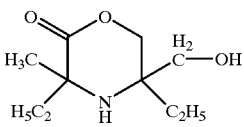

To a solution of 50.0 g (0.42 mol) of 2-amino-2-ethyl-1,3-propanediol in 75.3 g (0.63 moles) of chloroform and 302 g (4.2 moles) of 2-butanone, cooled to (0–5)° C., 84 g (2.1 moles) of ground sodium hydroxide are added.

After the addition, the mixture is maintained under stirring at room temperature overnight. To the mixture water is added in order to dissolve the salts. The water layer is separated and 70.0 ml (0.84 moles) of HCl 37% (% w/w) were added. The suspension is heated to reflux for 2 hours, concentrated in vacuum (90° C./10 mbar). The residue is taken up with 300 ml of toluene and the mixture heated to reflux being the residual water distilled off by azeotropation.

The organic solution is then added with 46 g (0.46 moles) of triethylamine and heated to reflux for 2 hours. After cooling to room temperature, the mixture is filtered and the organic solution is concentrated in vacuum (60° C./10 mbar). NMR Analysis (300 MHz, CDCl3) confirms the structure: δ=0.83 (m, 6H); 1.5 (m, 6H); 3.28 (d, 2H); 4.25 (m, 2H).

Example A15

Preparation of the Compound of the Formula

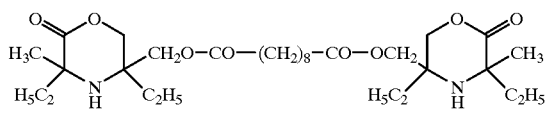

21.8 g (0.098 moles) of the product from Example A14 are dissolved in 300 ml of xylene and 10.2 g (0.044 moles) of sebacic acid dimethylester and 0.25 g of dibutyltin(IV) oxide are added. The mixture is heated to reflux and maintained at reflux for 18 hours while methanol formed during the reaction is distilled off by azeotropation. The mixture is then cooled to room temperature, washed with water, dried, filtered and evaporated in vacuum (60° C./10 mbar). A product is obtained whose NMR analysis (300 Mhz, CDCl3) conforms with the expected structure: δ=0.85–0.9 (m, 12H); 1.24 (broad s, 8H); 1.29 (s, 3H); 1.31 (s, 3H); 1.5 (m, 12H); 2.25 (t, 4H); 3.75–3.9 (m, 4H); 4.1–4.25 (m, 4H)

Example A16

Preparation of the Compound of the Formula

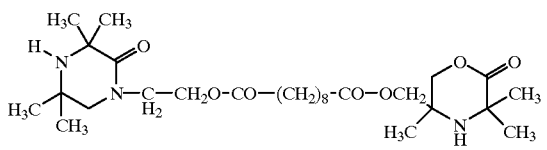

a) Preparation of 1-(2-hydroxyethyl)-3,3,5,5-tetramethyl-piperazin-2-one of the Formula

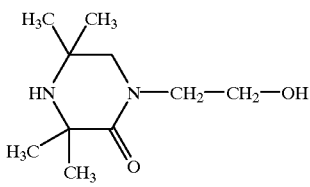

To a solution of 450 g (7.40 moles) of ethanolamine in 1000 ml of isopropanol, 607.8 g (6.55 moles) of 2-nitropropane and 100 ml of water are added. The solution is stirred at room temperature and 225.4 g (7.5 moles) of paraformaldehyde and 7 ml of 20% aqueous solution of sodium hydroxide (% w/v) are added, under stirring and maintaining the temperature at room temperature for 16 hours. The mixture is then heated to 50° C. being nitrogen bubbled into the mixture to eliminate the formaldehyde in excess. The mixture is then used for the reaction, without any isolation of the product 2-(2-nitro-2-methyl-propylamino)-ethanol.

The mixture so obtained is transferred into an autoclave and 100 g of Ni Raney arae added. The autoclave is closed and purged with nitrogen. Hydrogen is then added until to a pressure of 50 bars. The mixture is then maintained under a pressure of 50 bars of hydrogen, at room temperature and under stirring, for 8 hours and then heated to 50° C. at the same pressure. The catalyst is then separated off by filtration and the mixture is distilled under vacuum. A white oil is obtained (b.p. 100–105° C./13.3 mbar). N.M.R. analysis (¹H) conforms with the expected structure of 2-(2-amino-2-methyl-propylamino)-ethanol.

To 180 g (1.36 moles) of 2-(2-amino-2-methyl-propylamino)-ethanol in 1204 ml of acetone, 244.2 g (2.05 moles) of choroform are added.

The mixture is cooled to 5° C. under stirring and a solution of 327 g (8.18 moles) of sodium hydroxide in 327 ml of water is added slowly being the temperature of the mixture maintained at 0–5° C. during the addition.

The mixture is then stirred at 0–5° C. for further 2 hours and at room temperature for 15 hours. The pH of the aqueous solution is then corrected at 11 and the mixture is then stirred for further 4 hours.

The mixture is then filtered and the residue is washed with acetone.

The filtrate and acetone of washing are collected and evaporated under vacuum (70° C./24 mbar).

The residue is then distilled giving a white oil product (b.p. 115° C./2.66 mbar) that after some time gives the solid product (a; m.p. 91–93° C.).

b) 17.3 g (0.10 moles) of the product from the Example A1 and 20.0 g (0.10 moles) of 1-(2-hydroxyethyl)-3,3,5,5-tetramethyl-piperazin-2-one (a) and 14.9 g (0.19 moles) of pyridine are dissolved in 400 ml of dichloromethane. The solution is cooled to 0° C., 22.5 g (0.094 moles) of sebacoyl chloride are added slowly. After 1 hour the mixture is warmed to the room temperature and it is washed with a solution of K₂CO₃ and with distilled water, dried, filtered and evaporated in vacuum (60° C./10 mbar). A product is obtained whose NMR analysis (300 MHz, CDCl3) conforms with the expected structure: δ=1.06 (s, 3H); 1.08 (s, 6H); 1.23 (s, 6H); 1.29 (s, 3H); 1.32 (s, 3H); 2.17 (m, 4H); 3.16 (s, 2H); 3.51 (s, 2H); 3.83 (s, 2H).

Example A17 a) Preparation of the Compound of the Formula

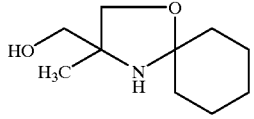

52.5 g (0.50 moles) of 2-amino-2-methyl-1,3-propanediol and 49.0 g (0.50 moles) of cyclohexanone are added to 300 ml of n-hexane, the mixture is heated to reflux and maintained for 20 hours being the water formed during the reaction distilled off by azeotropation. The mixture is evaporated in vacuum (40° C./10 mbar). A solid product is obtained whose NMR analysis (300 MHz) conforms with the expected structure.

b) Preparation of the Compound of the Formula

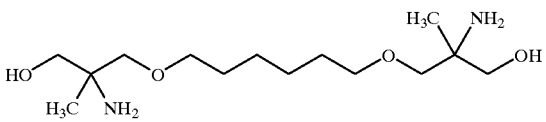

50.0 g (0.27 moles) of the product from the Example A17a are dissolved in 500 ml of toluene. 6.5 g (0.27 moles) of sodium hydride are added slowly to the solution cooled at 0° C. After that, the mixture is heated to the reflux for 5 hours. After cooling to 0° C., 33.0 g (0.135 moles) of 1,6-dibromohexane are added to the mixture then heated to the reflux for 10 hours. The mixture is washed with water, the organic phase is concentrated and dissolved in HCl 1M and the solution is heated to the reflux for 5 hours. A 10% (w/w) solution of NaOH is added until pH 12 is reached. The mixture is washed with dichloromethane; the water phase is evaporated in vacuum (80° C./10 mbar), 200 ml of THF is added to the residual, and the solution is dried, filtered and evaporated in vacuum (60° C./10 mbar). A product is obtained whose NMR analysis (300 MHz) conforms with the expected structure.

c) Preparation of the Compound of the Formula

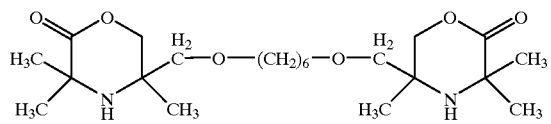

To a solution of 22.5 g (0.077 moles) of the product from the Example A17b in 27.6 g (0.23 moles) of chloroform and 89.4 g (1.54 moles) of acetone, cooled to (0–5)° C., 30.8 g (0.77 moles) of ground sodium hydroxide are added. After addition, the mixture is maintained under stirring at room temperature overnight. Then water is added in order to dissolve the salts, and 23 ml of HCl 37% (w/w) are added to the solution. The mixture is concentrated in vacuum. The residue is taken up with 300 ml of toluene and the mixture heated to reflux being the residual water distilled off by azeotropation. The organic solution is then added with 17.1 g (0.17 moles) of triethylamine and heated to reflux for 1 hour. After cooling to room temperature, the mixture is filtered and the organic solution is washed with water, dried, filtered and concentrated in vacuum (60° C./10 mbar). A product is obtained whose NMR analysis (300 MHz, CDCl3) conforms with the expected structure: δ=1.03 (s, 6H); 1.28 (s, 6H); 1.31 (s, 6H); 1.44 (broad, 4H); 3.1 (m, 4H); 3.3 (m, 4H; 4.06 (d, 2H); 4.26 (d, 2H).

Example A18

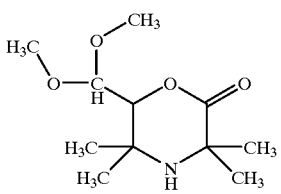

a) Henry Reaction

To a solution of 2-nitropropane (4.5 ml, 50 mmol) and Aliquar® (2.25 ml, 5 mmol) in NaOH (0.025 M, 150 ml) is added monomethylacetal of glyoxal (50 mmol) at 0° C. After 48 h the reaction is quenched with saturated brine and extracted with ether. The organic layer is dried (MgSO$_4$) and after concentration 8.6 g (90% yield) of product, 1,1-dimethoxy-3-nitro-3-methyl-butane-2-ol, is obtained.

$^1$H NMR (400 MHz, CDCl$_3$): δ 4.33 (1 H, d, J=5.6 Hz), 4.11 (1 H, dd, J=5.6, 4.6 Hz), 3.45 (3 H, s), 3.40 (3 H, s), 2.64 (1 H, d, J=4.6 Hz), 1.62 (3 H, s), 1.59 (3 H, s).

b) Reduction to 1,1-dimethoxy-3-amino-3-methyl-butane-2-ol

To a solution of the nitroalcohol (2 g, 10 mmol) prepared under (a) in methanol and THF (200 ml of a solution 1:1) is added Pd/C (500 mg, Fluka reagent) and then ammonium formiate (3.5 g, 55 mmol). The reaction is monitored by means of tlc until the reagent is consumed. After filtration of the catalyst the pure compound is obtained (1.3 g, 80% yield) by distillation at 75° C. (0.1 Torr).

$^1$H NMR (200 MHz, CDCl$_3$): δ 4.41 (1 H, d, J=5.3 Hz), 3.71 (1 H, d, J=5.3), 3.46 (3 H, s), 3.43 (3 H, s), 2.40–1.90 (3 H, bs), 1.15 (3 H, s), 1.09 (3 H, s).

c) Carboxylation and Cyclization

To a solution of the aminoalcohol (6.52 g, 40 mmol, as prepared in step b) in acetone (29.37 ml, 400 mmol) and chloroform (4.8 ml, 60 mmol) kept at 0° C. is added powdered NaOH (8 g, 200 mmol) with stirring during 7 hours. After this period the mixture is allowed to warm. The suspension is filtered and a white solid is obtained. The solid is dissolved in water and HCl is added up to pH=3. The solution is brought to reflux (ca. 110° C.). After two hours most water is evaporated at the rotoevaporator. Toluene is added (ca. 10 ml) to remove azeotropically the residual water. After adding triethylamine, the solution is refluxed for 1.5 h, cooled and filtered. The filtrate is concentrated to obtain the morpholinone (1.38 g, 15% yield).

Carboxylate: (CH$_3$O)$_2$CH—CH(OH)—C(CH$_3$)$_2$—NH—C(CH$_3$)$_2$—COONa $^1$H NMR (200 MHz, D$_2$O): δ 4.38 (1 H, d, J=4.46 Hz), 3.36 (3 H, s), 3.33 (3 H, s), 3.29 (1 H, d, J=4.46), 2.40–1.90 (1 H, bs), 1.20 (6 H, s), 1.11 (3 H, s), 1.04 (3 H, s).

Title Compound $^1$H NMR (200 MHz, CDCl$_3$): δ 4.44 (1 H, d, J=4.45 Hz), 4.20 (1 H, d, J=4.45), 3.48 (3 H, s), 3.45 (3 H, s), 1.85 (1 H, bs), 1.44 (3 H, s), 1.42 (3 H, s), 1.28 (3 H, s), 1.17 (3 H, s).

Example A19

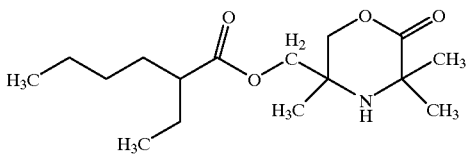

Following the procedure described in example A4 but replacing dodecanoic acid methyl ester by 2-ethylhexanoic acid methyl ester, leads to the above compound. It is obtained as an oil product whose $^1$H-NMR analysis (300 MHz, CDCl$_3$) conforms with the expected structure: δ=0.74–0.80 (m, 6H); 1.07 (s, 3H); 1.13–1.25 (m, 4H); 1.28 (s, 3H); 1.32 (s, 3H); 1.32–1.63 (m, 4H); 2.2 (m, 1 H); 3.83–3.84 (m, 2H); 4.07–4.25 (dd, 2H).

Example A20

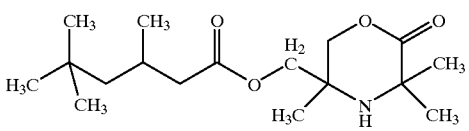

Following the procedure described in example A4 but replacing dodecanoic acid methyl ester by 3,5,5-trimethylhexanoic acid methyl ester, leads to the above compound. The title product is obtained as white solid, m.p. 60–65° C.

Example A21

Preparation of the Compound of the Formula

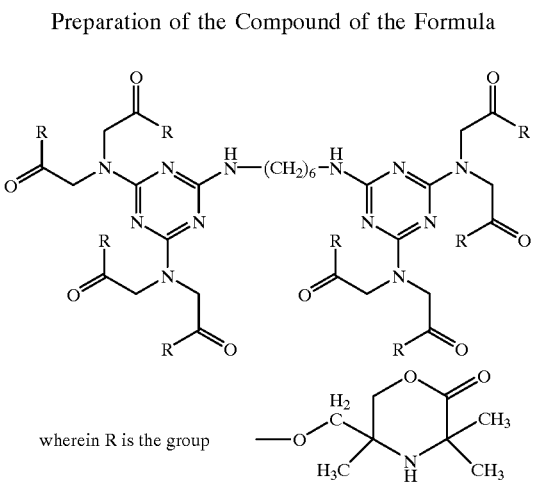

wherein R is the group

A) To a solution of 132 g (0.72 mol) of cyanuric chloride in 1400 ml of methylenechloride, 260 g (1.61 mol) of (methoxycarbonylmethyl-amino)-acetic acid methyl ester in 100 ml of methylenechloride are added drop by drop within 30 minutes. The solution is allowed to react for 2 hours at room temperature and 99.5 g (0.72 mol) of potassium carbonate in 75 ml of water are added. The mixture is heated at 40° C. and left to react for additional 2 hours. The mixture is then cooled to room temperature and 109.5 g (0.79 mol) of potassium carbonate are added. After 5 hours at 40° C. the mixture is cooled to room temperature and 150 ml of water are added. The organic layer is separated and washed twice with water, dried with sodium sulfate and evaporated under vacuum.

B) To a solution of 360 g (0.829 mol) of product from step A in 1800 ml of xylene, 48.1 g (0.415 mol) of dihexylamine are added. The solution is heated at 60° C. for 3 hours and for additional at 80° C. The mixture is cooled to 20° C. and 33 g (0.830 mol) of NaOH in 33 ml of water are added. The mixture is allowed to react for additional 4 hours at 80° C. The mixture is cooled to room temperature and a white solid is filtered off. The product is then washed twice with xylene.

C) To a solution of 16.6 g (0.0182 mol) of the product from step B in xylene, 35 g (0.202 mol) of 5-hydroxymethyl-3,3,5,-trimethyl-2-morpholone (product of example A1) are added. The mixture is heated to reflux and maintained at reflux for 40 hours being the methanol formed during the reaction distilled off by azeotropation. The mixture is then cooled to room temperature, washed with a 40% solution of sodium carbonate in water and twice with water, then it is dried under sodium sulfate, filtered and evaporated under vacuum. A white powder with melting point 62–68° C. is recovered.

Example A22

Preparation of the Compound of the Formula

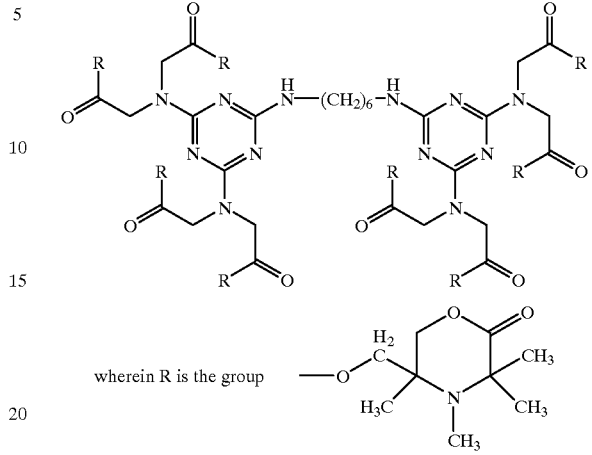

wherein R is the group

Following the procedure described in example A21 and using in step C the product of example A3 instead under the same experimental conditions, the compound of the above formula is obtained as a yellow powder of m.p. 70–75° C. Proton and carbon NMR confirm the structure.

Example A23

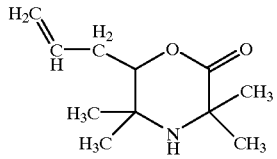

a) Synthesis of N-(tert-butoxycarbonyl)-2-amino-2-methyl-1-propanol

To solution of 2-amino-2-methyl-1-propanol (87 mmol, 8.3 ml) in 200 ml of $CH_2Cl_2$ is added di-tert-butyl dicarbonate (96 mmol, 21.52 g) in 50 ml of $CH_2Cl_2$. After 14 hours under argon, the solvent is evaporated under vacuum and 16.08 g (98% yield of pure compound is obtained.

$^1$H NMR (200 MHz, $CDCl_3$): δ 4.70 (1 H, bs), 4.09 (1 H, bs), 3.57 (1H, d, J=6.0), 1.42 (9 H, s), 1.24 (6 H, s).

b) Synthesis of N-(tert-butoxycarbonyl)-2-amino-2-methyl-propanal

To a solution of oxalyl chloride (66 mmol, 5.78 ml) in 150 ml of THF, DMSO is added (72 mmol, 5.1 ml) at −78° C. After 15 min, 60 mmol (11.35 g) of the product of step a in 75 ml of THF is added. The reaction is allowed to warm to −35° C. and triethylamine is added (300 mmol, 42 ml). The temperature is allowed to raise up to 20° C. and after one hour the reaction is quenched with 120 ml of aq. $NH_4Cl$. The organic layer is separated while the aqueous one is extracted with diethylether (3×50 ml). The combined organic phase is washed with brine and anhydrified ($MgSO_4$). After filtration the solvent is evaporated affording 10.78 g (96% yield) of pure compound.

$^1$H NMR (200 MHz, $CDCl_3$): δ 9.43 (1 H, s), 4.95 (1 H, bs), 1.44 (9 H. s), 1.33 (6 H, s).

c) Synthesis of N-(tert-butoxycarbonyl)-5-amino-5-methyl-1-hexen-4-ol

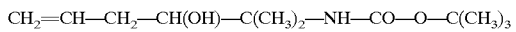

To a solution of the product of step b (20 mmol, 3.74 g) in 20 ml of $CH_2Cl_2$ at −78° C., 22 ml of a solution 1 M of $TiCl_4$ in $CH_2Cl_2$ is added. After 10 min, trimethyallylsilane (22 mmol, 3.5 ml) in 20 ml of $CH_2Cl_2$ is added. After one hour the reaction is quenched with water. The organic layer is separated and extracted with $CH_2Cl_2$ (3×25 ml). The solution is anhydrified ($Na_2SO_4$) and after concentration 1.14 g of product is obtained.

$^1$H NMR (200 MHz, $CDCl_3$): δ 6.10–5.80 (1 H, m), 5.20–5.05 (2 H, m), 4.68 (1 H. bs), 3.88 (1 H, bs), 3.60–3.50 (1 H, m), 3.40–1.95 (2 H, m), 1.43 (9 H, s), 1.36 (3 H, s), 1.22 (6 H, s).

d) Synthesis of the Title Product 5-allyl-2,2,6,6,-tetramethylmorpholinone

To a solution of the product of step c (5 mmol aminoalcohol) in acetone (2.44 ml, 50 mmol) and chloroform (0.6 ml, 7 mmol) kept at 0° C. is added powdered NaOH (1 g, 25 mmol) during 7 hours. After this period the mixture is allowed to warm. The suspension is filtered and the carboxylate of the formula

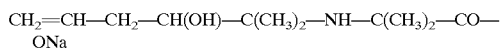

is obtained as a white solid.

The solid is dissolved in water and HCl is added up to pH=3. The solution is brought to reflux (ca. 110° C.). After 5 hours most water is evaporated at the rotoevaporator. Toluene is added (ca 10 ml) to remove azeotropically the residual water. After adding triethylamine, the solution is refluxed 1.5 h, cooled and filtered. The filtrate is concentrated to obtain the title product.

$^1$H NMR (200 MHz, $CDCl_3$): δ 6.05–5.70 (5.20–4.90 (2 H, m), 4.22 (1 H, d, J=6.4 Hz), 4.17 (1 H, d, J=6.4 Hz), 1.44 (3 H, s), 1.43 (3 H, s), 1.14 (3 H, s), 1.12 (3 H, s).

Example A24

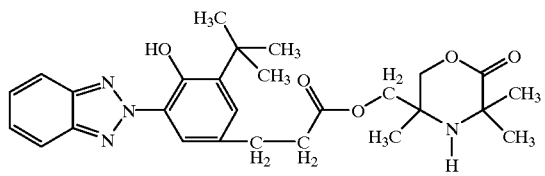

Following the procedure described in example A4, 15.0 g (87 mmoles) of the product from example A1 are reacted with 25.6 g (72.5 mmoles) of 3-(3-{2-benztriazolyl}4-hydroxy-5-tert.butylphenyl)propionic acid methyl ester in 100 ml xylene in the presence of 0.8 g dibutyltin(IV)oxide. The reaction mixture is filtered through silica, evaporated to dryness and the resulting solid recrystallized from ethylacetate, giving the title compound of m.p. 137° C.

Example A25

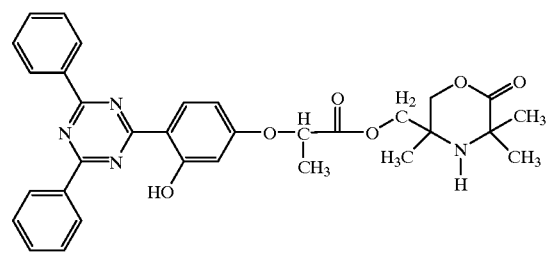

Following the procedure described in example A24 and replacing 3-(3-{2-benztriazolyl}4-hydroxy-5-tert.butylphenyl)propionic acid methyl ester by 31.0 g (72.5 mmoles) of 2,4-diphenyl-6(2-hydroxy-4-{1-ethoxycarbonylethoxy}phenyl)-1,3,5-triazine and recrystallizing the product from ethyl acetate yields the title product of m.p. 168° C.

Example A26

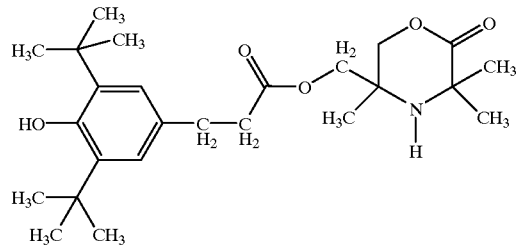

Following the procedure described in example A24 and replacing 3-(3-{2-benztriazolyl}4-hydroxy-5-tert.butylphenyl)propionic acid methyl ester by 25.1 g (72.5 mmoles) of 4-hydroxy-3,5-di-tert.butylphenyl-propionic acid methyl ester and recrystallizing the product from hexane yields the above compound of m.p. 99° C.

Example A27

Replacing in the procedure described in example A26 the product of example A1 by 18.0 g (96 mmoles) of the product of example A3 yields the compound of formula

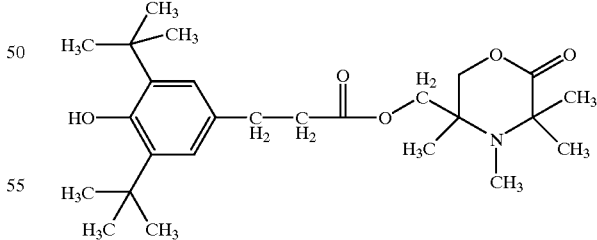

of m.p. 93° C.

B: APPLICATION EXAMPLES

Example B1

Light-stabilizing Action in Polypropylene Tapes a) 1 g of each of the compounds listed in the following Table 1a, 1 g of tris[2,4-di-tert-butylphenyl]phosphite, 0.5 g of pentaerythritol tetrakis[3-(3,5-di-tert-butyl-4-hydroxyphenyl)propionate] and 1 g of calcium stearate are mixed in a turbomixer with 1000 g of polypropylene powder having a melt index of 3.7 (measured at 230° C. and 2.16 kg). The mixtures are extruded at 200–220° C. to give polymer granules which are subsequently converted to stretched tapes of 50 μm thickness and 2.5 mm width, using a semi-industrial type of apparatus (®Leonard-Sumirago (VA)) and working under the following conditions:

| | |
|---|---|
| Extruder temperature: | 210–230° C. |
| Head temperature: | 240–260° C. |
| Stretch ratio | 1:6 |

The tapes thus prepared are mounted on or white card and exposed in a Weather-O-Meter 65 WR (ASTM D 2565–85) with a black panel temperature of 63° C.

The residual tenacity is measured, by means of a constant velocity tensometer, on a sample taken after various light exposure times; from this, the exposure time (in hours) required to halve the initial tenacity (T50) is measured.

By way of comparison, tapes prepared under the same conditions as indicated above, but without the addition of the stabilizers of the present invention are exposed.

The results are shown in Table 1a.

TABLE 1a

| Stabilizer | $T_{50}$ (hours) |
|---|---|
| without stabilizer | 500 |
| Compound of Example A6 | 1930 |
| Compound of Example A8 | 1940 |
| Compound of Example A22 | 1600 | b) Further tapes of thickness 50 μm are prepared and tested as described above under (a) but using the double amount of the costabilizer pentaerythritol tetrakis[3-(3,5-di-tert-butyl-4-hydroxyphenyl)propionate] (1.0 g instead of 0.5 g on 1000 g polypropylene powder). The results are shown in Table 1b.

TABLE 1b

| Stabilizer | $T_{50}$ (hours) |
|---|---|
| none | 500 |
| Compound of Example A9 | 2320 |

Example B2

Light Stabilizing Action in Polypropylene Plaques.

1 g each of the compounds indicated in Table 2a, 1 g of tris(2,4-di-t-butylphenyl)phosphite, 0.5 g of pentaerythritol tetrakis[3-(3,5-di-t-butyl-4-hydroxyphenyl)propionate], 1 g of calcium stearate and 1 g of Filofin Blue 4G are mixed in a turbo mixer with 1000 g of polypropylene powder of melt index=2 g/10 minutes (measured at 230° C. and 2.16 kg).

The mixtures obtained are extruded at a temperature of 200–230° C. to give polymer granules which are then converted into plaques of 2 mm thickness by injection moulding at 200–230° C. The plaques obtained are exposed in a model 65 WR Weather-O-Meter (ASTM D2565-85) with a black panel temperature of 63° C. until surface embrittlement (chalking) starts. A plaque of polypropylene prepared under the same conditions as indicated above but without the addition of the compounds of the invention is exposed for comparison. In Table 2a, the exposure time needed to reach this start of embrittlement is given in hours. The longer the time, the better is the stabilizing effect.

TABLE 2a

| Stabilizer | Chalking time (hours) |
|---|---|
| without stabilizer | 570 |
| Compound of Example A4 | 6530 |
| Compound of Example A7 | 4550 |
| Compound of Example A9 | 5100 |

Example B3

Stabilizing a 2-coat Metallic Coating Material

The novel light stabilizers indicated in Tables 3a and 3b are dissolved in 30 g of Solvesso® 100 and tested in a clearcoat of the following composition:

| | |
|---|---|
| Synthacryl ® SC 303[1] | 27.51 |
| Synthacryl ® SC 370[2] | 23.34 |
| Maprenal ® MF 650[3] | 27.29 |
| Butyl acetate/Butanol (37/8) | 4.33 |
| Isobutanol | 4.87 |
| Solvesso ® 150[4] | 2.72 |
| Crystal Oil K-30[5] | 8.74 |
| Levelling assistant Baysilon ® MA[6] | 1.20 |
| | 100.00g |

[1] Acrylate resin from Hoechst AG; 65% solution in xylene/butanol 26:9
[2] Acrylate resin from Hoechst AG; 75% solution in Solvesso ® 100[4]
[3] Melamine resin from Hoechst AG; 55% solution in isobutanol
[4] Aromatic hydrocarbon mixture, boiling range 182–203° C. (Solvesso ® 150) or 161–178° C. (Solvesso ® 100); (manufacturer: Esso)
[5] Aliphatic hydrocarbon mixture: boiling range 145–200° C.; (manufacturer: Shell)
[6] 1% in Solvesso ® 150[4]; (manufacturer: Bayer AG)

1.0% of the novel compounds, based on the solids content of the coating material, are added to the clearcoat. A clearcoat prepared in the same way but containing no novel compound is used for comparison.

The clearcoat is diluted to spray viscosity with Solvesso® 100 and applied by spraying to a prepared aluminium panel (UNIPRIME® Epoxy, silver-metallic basecoat) and is stoved at 130° C. for 30 minutes, to give a dry film thickness of 40–50 μm of clearcoat.

The samples are then weathered in an UVCON® weathering apparatus (from Atlas Corporation; UVB-313 lamps) with a cycle of 8 hours of UV radiation at 70° C. and 4 hours of condensation at 50° C.

The surface gloss (20° gloss in accordance with DIN 67530) of the samples is measured at regular intervals. The results are illustrated in Tables 3a and 3b below. High gloss values indicate a good stabilization.

TABLE 3a

20° gloss after x hours of weathering under UVCON (UVB-313)

| | x hours | | | |
|---|---|---|---|---|
| Compound of: | x = 0 | 400 | 800 | 1200 |
| Unstabilized | 91 | 82 | 37 | 15* |
| Example A6 | 93 | 93 | 83 | 62 |

TABLE 3a-continued

20° gloss after x hours of weathering under UVCON (UVB-313)

| | x hours | | | |
|---|---|---|---|---|
| Compound of: | x = 0 | 400 | 800 | 1200 |
| Example A7 | 93 | 92 | 81 | 65 |
| Example A10 | 93 | 92 | 76 | 52 |

*sample shrinks

TABLE 3b

20° gloss after x hours of weathering under UVCON (UVB-313)

| | x hours | | | |
|---|---|---|---|---|
| Compound of: | x = 0 | 400 | 800 | 1200 |
| Unstabilized | 90 | 84 | 41 | |
| Example A5 | 91 | 88 | 74 | |
| Example A9 | 91 | 89 | 82 | |

Example B4

Curing of an Acid Catalyzed High Solid TSA Clearcoat

The novel light stabilizers indicated in Tables 4a and 4b are dissolved in 2–3 g of Xylene and tested in a clearcoat of the following composition:

| | |
|---|---|
| Cymel ® 303[1] | 19.18g |
| Joncryl ® 510[2] | 56.16g |
| Butanol | 14.16g |
| Methyl-amyl-ketone (MAK)[3] | 9.89g |
| DC-57 (10% by weight solution in MAK)[4] | 0.61g |
| | 100.00g |

[1] Melamine crosslinker from American Cyanamide Corp.
[2] High solid acrylic resin from Johnson Polymer
[3] Solvent
[4] Flow control agent from Dow Corning 0.8% by weight of the resin solids of p-toluene sulfonic acid is added as curing catalyst.

1% of stabilizer is added to the clearcoat, based on the solids content of the coating material. The control is a clearcoat containing no light stabilizer.

The clearcoat is applied using the draw down technique to a previously prepared black coated iron panel and is cured at 90° C. for 30 minutes. The resulting dry film thickness of the clearcoat is 40–50 μm. Subsequently, the surface hardness (pendulum hardness as defined in DIN 53157) is determined. The results are compiled in Tables 4a and 4b. A high measure indicates high surface hardness and good cure.

TABLE 4a

Pendulum Hardness (DIN 53157) of Clearcoat after Cure

| Light Stabilizer of: | Pendulum Hardness |
|---|---|
| control (unstabilized) | 100 s |
| Example A6 | 98 s |
| Example A7 | 97 s |
| Example A10 | 96 s |

TABLE 4b

Pendulum Hardness (DIN 53157) of Clearcoat after Cure

| Light Stabilizer of: | Pendulum Hardness |
|---|---|
| control (unstabilized) | 101 s |
| Example A9 | 101 s |

The results show that the use of stabilizers of the invention has no negative impact on the curing.

Example B5

Measuring the Discolouration of Cured Powder Coatings Based on a Carboxy-functional Polyester with Araldit™ PT910.

A powder coating composition (see Table 5a) is prepared by mixing the different components, with the exception of the stabiliser, and extruding the mixture using a Buss PLK46L type extruder at 40° C. (screw and zone 1) and at 100° C. (zone 2) at 125 rpm. The melting temperature in the extruder is about 96° C. The powder coating composition is then ground to an average particle size of about 40 μm. Instead of spraying the formulation dry as powder coating, it is dissolved or dispersed in a solvent mixture (see Table 5b) together with the corresponding amount of stabiliser and is then applied to a white aluminium coil coat sheet using a 150 μm casting knife.

TABLE 5a

| | Sample (amounts in gram) | |
|---|---|---|
| Components | 1a | 1b to 1g |
| Alftalat ™ 9936/A[a] | 893 | 893 |
| Araldit ™ PT910[b] | 83 | 83 |
| Resiflow ™ PV88 | 20 | 20 |
| benzoin | 4 | 4 |
| titanium dioxide type 2160[c] | 500 | 500 |
| stabilisers (see Table 5c) | 0 | 8.93 |
| total: | 1500 | 1508.9 |

[a] Carboxy-functional polyester, of Vianova Resins s.P.A., Italy.
[b] Araldit ™ PT910 is an epoxy crosslinker, of Ciba Specialty Chemicals, Basel, Switzerland
[c] TiO$_2$, of Kronos Titan International, Leverkusen, Germany.

TABLE 5b

| Components | Amounts |
|---|---|
| dry acetone/dichloromethane 4:1 v/v | 541 g |
| Byk ™ 300[d] | 7 g |
| Fluorad ™ FC170C[e] | 2 g |
| powder coating composition (acc. to Table 5a) | 450 g |

[d] Byk ™ 300 is an anticratering agent based on dimethylpolysiloxane, of Byk Chemie, D-4230 Wesel, Germany.
[e] Fluorad ™ FC170C is a nonionic fluorinated alkylpolyoxyethylene ethanol crosslinker, of 3M Industrial Chemical Products Division, St. Paul, MN 55144-1000, USA.

After a 48 hour drying time, the coatings are stoved in an electric furnace. The chosen oven temperatures and stoving times correspond in practice to severe overbaking conditions. The colour after stoving is measured using a spectrophotometer according to DIN 6174, taking b* as measure of the yellowing. High b* values denote severe yellowing. The results are compiled in Table 5c.

TABLE 5c

| Sample | Stabiliser | Colour after stoving in an electric furnace (b*) for 90 min at 180° C. |
|---|---|---|
| a | none | 2.58 |
| b | Example A6 | 2.13 |
| c | Example A8 | 2.22 |
| e | Example A4 | 2.15 |
| f | Example A7 | 2.17 |
| g | Example A9 | 2.30 |
| h | Example A22 | 2.42 |
| i | Example A5 | 2.22 |

Example B6

Measuring the Discolouration of Cured Powder Coatings Based on a Carboxy-functional Polyester with Primid™ XL552.

White powder coating compositions are prepared which comprise a stabiliser according to this invention and a phosphite or phosphonite as costabiliser. The powder coating compositions according to Table 6a are mixed well and extruded on a Prism 16 mm twin-screw extruder at 110° C. and at 300 rpm; amounts are given in grams.

The extrudate is ground to about 40 μm and is sieved through a 125 μm sieve. The powder coating so obtained is applied to white coil coat aluminium panels using a Wagner Corona-Star gun at 60 kV corona voltage.

A gas reactor is used to cure the powder paints, which simulates conditions in a real industrial gas oven. The gas reactor consists of an annealed, non-distorting stainless steel plate with a tightly-fitting steel lid of external dimensions (including lid) of 370×180×32 mm. The steel plate has a cavity of size 320×140×7 mm in which the test panels are cured. At one end of the reactor a preheated mixture of air and $NO_2$ gas is let in and at the other end allowed to escape. A flow rate of 450 NL/hr is used, which is sufficient to flush the apparatus in a minimum time without causing disturbance of the surface of the powder paint. The gas flow is controlled by two thermal mass flow controllers supplied by Bronkhorst Hi-Tec NV, Netherlands. The gas reactor is mounted on insulating supports and fitted inside a standard laboratory oven, together with a large helical steel tube (85 m×5 mm internal diameter) which is used to preheat the air/$NO_2$ mixture.

The coating thickness after stoving is 90 μm. The colour after stoving at 190° C. is measured as described in example B5, high b* values denote severe yellowing. Results are compiled in Table 6b.

TABLE 6a

| | Sample/Amount (g) | | | | | |
|---|---|---|---|---|---|---|
| Component | a | b | c | d | e | f |
| Uralac ™ P3401[a)] | 570 | 570 | 570 | 570 | 570 | 570 |
| Primid ™ XL552[b)] | 30 | 30 | 30 | 30 | 30 | 30 |
| Kronos ™ 2160 | 300 | 300 | 300 | 300 | 300 | 300 |
| Resiflow ™ PV5 | 9 | 9 | 9 | 9 | 9 | 9 |
| benzoin | 2.5 | 2.5 | 2.5 | 2.5 | 2.5 | 2.5 |
| C[c)] | — | 5.7 | — | — | 2.85 | — |
| D[d)] | — | — | 5.7 | — | — | 2.85 |
| cmpd of Ex. A6) | — | — | — | 5.7 | 2.85 | 2.85 |

[a)]Carboxy-functional polyester, of DSM N.V., Zwolle, Netherlands.
[b)]Primid ™ XL552 is a hydroxyalkylamide crosslinker, of Ems Chemie AG, Domat/Ems, Switzerland.
[c)]Costabiliser C is a commercially available phosphite of formula $C_2H_5O$—$P(OR)_3$, wherein R is 2,4-di-tert-butyl-6-methylphenyl.
[d)]Costabiliser D is a commercially available phosphonite which contains a main component of formula

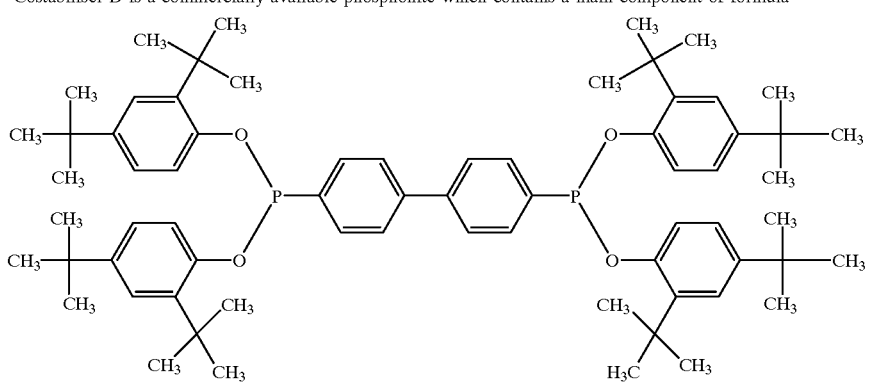

TABLE 6b

Effect of a Morpholinone Stabiliser on the Colour of a Polyester/Primid XL552 white Powder Coating; Yellowing (b*) after baking at 190° C. for the indicated period

| | | b* after baking at 190° C. for | | | |
|---|---|---|---|---|---|
| No. | Stabiliser(s) | 20 min. | 80 min. | 20 min; +50 ppm NOx | 20 min.; +200 ppm NOx |
| a | none | 4.0 | 5.4 | 5.0 | 5.0 |
| b | costabiliser C | 3.6 | | 4.7 | 5.3 |
| c | costabiliser D | 3.5 | 4.9 | | |
| d | compound A6 | 3.8 | 4.9 | 4.5 | 4.8 |
| e | C + A6 | 3.6 | | 4.1 | 4.4 |
| f | D + A6 | 3.5 | 4.7 | | |

Example B7

Stabilizing a 2-coat Metallic Coating Material

A clearcoat containing 1% of the stabilisers indicated in the following Table 7a is prepared and subjected to weathering as described in example B3, except that a weathering cycle of 4 hours of UV radiation at 70° C. and 4 hours of condensation at 50° C. is chosen.

The surface gloss (20° gloss in accordance with DIN 67530) of the samples is measured at regular intervals. The results are illustrated in Table 7a below. High gloss values indicate a good stabilization.

TABLE 7a

20° C. gloss after x hours of weathering under UVCON (UVB-313)

| Light- stabilizer | 20° * gloss as defined in DIN 67530 after . . . hours weathering in the ® UVCON (UVB-313) | | | |
|---|---|---|---|---|
| | 0 hours | 200 hours | 400 hours | 600 hours |
| None | 94 | | 87 | |
| Example A13 | 93 | | 91 | |
| Example A16 | 94 | | 93 | |
| Example A18 | 94 | | 91 | |

The stabilizers of present invention have no adverse effects on the initial gloss and improve the gloss retention on weathering.

Example B8

Stabilisation of Photographic Layers

Chromogenic photographic layers are prepared by hand-coating a gelatine emulsion containing silver bromide, yellow coupler and an additive on a polyethylene-coated paper. The composition of the layers is as given in following table 8a, amounts are in mg/m²:

TABLE 8a

| Component | Amount in the layer |
|---|---|
| Gelatine | 5150 |
| AgBr | 520 |
| Yellow coupler | 835 |
| Coupler solvent | 278 |
| Additive (see table 8b) | 250 |
| Hardener | 300 |
| Surfactant | 340 |

TABLE 8a-continued

| Component | Amount in the layer |
|---|---|

The yellow coupler is the compound of the formula:

[Chemical structure of yellow coupler with $H_{33}C_{16}O$, $(CH_3)_3C$, $SO_2$, $NH$, $C_2H_5$ groups]

Coupler solvent is phthalic acid di-n-butyl ester.
The hardener is 2,4-dichloro-6-hydroxy-1,3,5-triazine.
The surfactant is the compound of the formula:

[Chemical structure with $H_3C$, $CH_3$, $SO_3Na$ groups on naphthalene]

Each layer is dried for 7 days in a ventilated cabinet.

The dried samples are exposed to white light through a stepwedge of 0.3 logE exposure steps. They are developed with the P94 process for negative colour paper from Agfa-Gevaert, following the manufacturers recommendations.

After exposure and processing, the remission density of the yellow dye is measured in the blue channel; results are given in Table 8b. Compound D is 3,3,5,5-tetramethyl-2-morpholinone (described in U.S. Pat. No. 4,528,370 as stabilizer for some synthetic polymers).

TABLE 8b

| Additive: | none | D | Ex. A1 | Ex. A6 | Ex. A7 | Ex. A21 | Ex. A22 | Ex. A9 |
|---|---|---|---|---|---|---|---|---|
| 100 × $D_{min}$: | 8 | 8 | 8 | 8 | 8 | 9 | 9 | 10 |
| 100 × $D_{max}$: | 206 | 251 | 252 | 259 | 241 | 233 | 258 | 254 |

The results show that the additive of the present invention improves the maximal dye yield.

Example B9

Stabilisation of Photographic Layers

Chromogenic photoaraphic layers are prepared by hand-coating a gelatine emulsion containing silver bromide, cyan coupler and an additive on a polyethylene-coated paper.

The composition of the layer is as given in following table, amounts are in mg/m²:

| Component | Amount in the layer |
|---|---|
| Gelatine | 5150 |
| AgBr | 260 |
| Cyan coupler | 272 |
| Coupler solvent | 181 |
| Additive (see table 9a) | 272 |
| Hardener | 300 |
| Surfactant | 170 |

The cyan coupler is the compound of the formula:

[Chemical structure of cyan coupler with OH, Cl, CH$_3$, C(CH$_3$)$_3$ groups]

Coupler solvent, hardener and surfactant are the same as used in preceding example B8.

Each layer is dried for 7 days in a ventilated cabinet.

The dried samples are exposed to white light through a stepwedge of 0.3 logE exposure steps. They are developed with the P94 process for negative colour paper from Agfa-Gevaert, following the manufacturers recommendations.

After exposure and processing, the remission density of the cyan dye is measured in the red channel. The samples are then stored at 75° C. and 60% relative humidity for 28 days. The density loss (-ΔD) starting from a red-density of 1 is determined; results are given in Tab. 9a.

TABLE 9a

| Additive | -ΔD(28 days at 75° C./60% rH, from OD = 1) |
|---|---|
| none | 14% |
| Example A7 | 7% |
| Example A9 | 7% |

These results show that additives of the present invention improve the dark stability of cyan photographic layers.

Example B10

Stabilisation of Photographic Layers

Chromogenic photographic layers are prepared by hand-coating a gelatine emulsion containing silver bromide, magenta coupler and an additive on a polyethylene-coated paper.

The composition of the layer is as given in following table, amounts are in mg/m$^2$:

| Component | Amount in the layer |
|---|---|
| Gelatine | 5150 |
| AgBr | 520 |
| Magenta coupler | 417 |
| Coupler solvent | 208 |
| Additive (see table 10a) | 209 |
| Hardener | 300 |
| Surfactant | 85 |

-continued

| Component | Amount in the layer |
|---|---|

The magenta coupler is a compound of the formula:

[Chemical structure of magenta coupler with Cl, OH, C(CH$_3$)$_3$, H$_{25}$C$_{12}$ groups]

The coupler solvent is triphenylphosphate.
Hardener and surfactant are the same as used in example B8.

Each layer is dried for 7 days in a ventilated cabinet.

The dried samples are exposed to white light through a stepwedge of 0.3 logE exposure steps. They are developed with the P94 process for negative colour paper from Agfa-Gevaert, following the manufacturers recommendations.

After exposure and processing, the remission density of the magenta dye is measured in the greenchannel. The samples are then exposed in an Atlas weatherometer so as to receive 30 kJ/cm$^2$ light energy. The temperature is 43° C. and the relative humidity 50%. The density loss (-ΔD) starting from a green-density of 1 is determined. Results are given in Table 10a.

TABLE 10a

| Additive | -ΔD(30kJ/cm$^2$, from OD = 1) |
|---|---|
| none | 44 |
| Example A7 | 27 |
| Example A9 | 28 |

These results show that additives of the present invention improve the light stability of magenta photographic layers.

Example B11

Stabilization of a Gray Pigmented Polycarbonate/ABS Blend

Commercial PC/ABS-blend (Cycoloy™ MC 8002; 50/50 wt/wt blend of PC and ABS pigmented with 1% by weight of Gray 9779 is stabilized by addition of 1% by weight of 2-(2'-hydroxy-3',5'-bis(1,1-dimethylbenzyl)phenyl)-benztriazole (C) and 0.5% by weight of the compound indicated in table 11. A sample containing only the 1% by weight of the benztriazole stabilizer and an unstabilized sample serve as comparison. Izod bars (2.5"L×0.5"W×0.125"W) are prepared by injection molding on a BOY 30 machine, barrel temperature 475–515° F., die temperature 515° F. Accelerated weathering is performed using an Atlas Ci65A Weather-o-meter (XAW), operated in either "Dry XAW" mode (ASTM G26-90 method C). After regular intervals, the color change ΔE according to DIN 6174 is determined. Results are compiled in table 11.

TABLE 11

Color change (ΔE) of gray pigmented PC after the indicated irradiance time

| Irradiance time:<br>Stabilizer | 94.8 h<br>ΔE | 500.5 h<br>ΔE |
|---|---|---|
| none | 1.5 | 6.9 |
| C | 0.7 | 4.2 |
| C + A7 | 0.6 | 2.7 |

Example B12

Stabilization of a White Pigmented Polycarbonate/ABS Blend

Samples are prepared from commercial PC/ABS-blend (Cycoloy™ MC 8002; 50/50 wt/wt blend of PC and ABS) as described in example B11 except that $TiO_2$ (Tiona™ RCL-4 rutile; SCM chemicals) is used as pigment. Weathering and assessment is done as described in example B11; results are compiled in table 12.

TABLE 12

Color change (ΔE) of white pigmented PC after the indicated irradiance time

| Irradiance time:<br>Stabilizer | 499.3 h<br>ΔE | 999.8 h<br>ΔE | 1249.3 h<br>ΔE |
|---|---|---|---|
| none | 11.6 | 21.8 | 23.7 |
| C | 6.0 | 15.7 | 17.4 |
| C + A7 | 1.9 | 9.7 | 11.1 |

PC/ABS samples stabilized according to the invention show an excellent color stability.

What is claimed is:
1. Compound of the formula A, B, C or D

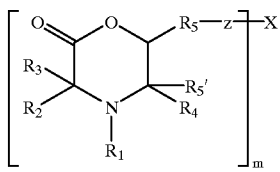
(A)

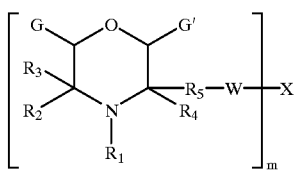
(B)

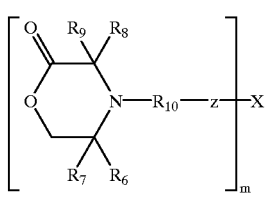
(C)

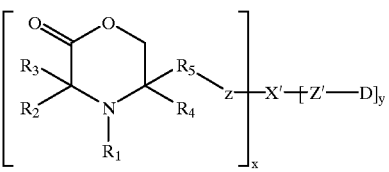
(D)

where
  m is the valency of X and is an integer from the range 1–8;
  x and y are each integers from the range 1–7 obeying the condition x+y=m;
  G is =O and G' is H or R'$_5$; or G' is =O and G is H or R'$_5$;
  R$_1$ is hydrogen; C$_1$–C$_{18}$alkyl; C$_2$–C$_{18}$alkyl substituted by OH and/or phenyl; oxyl; OH; C$_2$–C$_{12}$cyanoalkyl; C$_2$–C$_{12}$cyanoalkoxy; C$_1$–C$_{18}$alkoxy; C$_5$–C$_{12}$cycloalkoxy; C$_3$–C$_8$alkenyl; C$_3$–C$_8$alkynyl; C$_3$–C$_8$alkenyloxy; C$_7$–C$_{12}$phenylalkyl; C$_7$–C$_{12}$phenylalkyl substituted in the alkyl moiety by hydroxy; C$_7$–C$_{15}$phenylalkyl, which is substituted on the phenyl ring by 1, 2 or 3 radicals selected from C$_1$–C$_4$alkyl and C$_1$–C$_4$alkoxy; C$_7$–C$_{15}$phenylalkoxy; C$_7$–C$_{15}$phenylalkoxy, which is substituted on the phenyl ring by 1, 2 or 3 radicals selected from C$_1$–C$_4$alkyl and C$_1$–C$_4$alkoxy; or R$_1$ is C$_1$–C$_8$alkanoyl; C$_3$–C$_5$alkenoyl; C$_1$–C$_{18}$alkanoyloxy; glycidyl;
  R$_2$, R$_4$, R$_5$', R$_6$, R$_7$, R$_8$ and R$_9$ are, independently of one another, C$_1$–C$_{18}$alkyl, C$_3$–C$_8$alkenyl, C$_5$–C$_{12}$cycloalkenyl, C$_5$–C$_{12}$cycloalkyl, C$_6$–C$_{12}$bicycloalkenyl, or C$_6$–C$_{12}$bicycloalkyl;
  R$_3$ is C$_1$–C$_8$hydroxyalkyl, C$_1$–C$_{18}$alkyl or C$_5$–C$_{12}$cycloalkyl;
  or R$_2$ and R$_3$, R$_4$ and R$_5$', R$_6$ and R$_7$, R$_8$ and R$_9$ form, together with the carbon atom they are attached to, C$_5$–C$_{12}$cycloalkylene;
  R$_5$ is C$_1$–C$_8$alkylene; C$_1$–C$_8$alkylene-CO—; and in formula A also may be a direct bond; and may be also C$_1$–C$_8$alkylene substituted by OH or OCOR$_{15}$, provided that the OH or OCOR$_{15}$ group does not bond directly to a carbon atom that also bonds directly to —O— or —NR'$_{14}$—;
  R$_{10}$ is C$_2$–C$_8$alkylene; C$_1$–C$_8$alkylene-CO—;
  R'$_{10}$ is hydrogen or C$_1$–C$_8$alkyl or C$_5$–C$_{12}$cycloalkyl;
  W is —O— or —NR'$_{14}$— and, if m is not 1, W can also be a direct bond;
  X' is as defined for X below;
  Y is —O— or —NR'$_{14}$—;
  Z and Z', independently, are a direct bond or have a meaning given for Y;
  when m is 1, X is C$_1$–C$_{18}$alkyl; C$_1$–C$_{18}$alkyl substituted by C$_1$–C$_{18}$alkoxy, —N(R'$_{14}$)$_2$, —OH, —OCO—R$_{11}$, —COR$_{11}$, —COOR$_{13}$, CN, —(O)$_i$—P(=O)$_i$(OR$_{111}$)$_2$, C$_5$–C$_{12}$cycloalkoxy, allyloxy, halogen, —COOH, —CON(R'$_{14}$)$_2$, phenoxy and/or C$_1$–C$_{18}$alkyl-, C$_1$–C$_{18}$alkoxy- or halo-substituted phenoxy; or X is —P(=O)$_i$(OR$_{111}$)$_2$; C$_3$–C$_{30}$alkyl which is interrupted by —O— and can be substituted by OH; C$_5$–C$_{12}$cycloalkyl; C$_3$–C$_6$alkenyl; glycidyl; C$_7$–C$_{15}$phenylalkyl; C$_7$–C$_{15}$phenylalkyl, which is substituted on the phenyl ring by a radical selected from C$_1$–C$_4$alkyl and C$_1$–C$_4$alkoxy; —SO$_2$—R'$_{11}$; or is a group of formulae IIIa–IIIe —CO—R$_{11}$ (IIIa)

—R$_{12}$—COO—R$_{13}$ (IIIb)

—CO—NH—R$_{14}$ (IIIc)

—CO—R$_{18}$—COO—R'$_{17}$ (IIId)

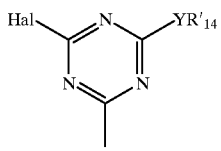 (IIIe)

and in formulae A and C, X can also be hydrogen or CN;

i is 0 or 1;

Hal stands for halogen or a residue Y—R'$_{14}$;

R$_{11}$ is hydrogen; C$_1$–C$_{18}$alkyl; C$_1$–C$_{18}$alkyl which is substituted by C$_1$–C$_{18}$alkoxy, —N(R'$_{14}$)$_2$, —OH, —OCO—R$_{111}$, —COR$_{111}$, CN, —(O)$_i$—P(=O)$_i$(OR$_{111}$)$_2$, C$_5$–C$_{12}$cycloalkoxy, allyloxy, halogen, —COOH, —CON(R'$_{14}$)$_2$, phenoxy and/or phenoxy which is substituted by C$_1$–C$_{18}$alkyl, C$_1$–C$_{18}$alkoxy or halogen; C$_3$–C$_{50}$alkyl interrupted by O; C$_5$–C$_{12}$cycloalkyl; C$_5$–C$_{12}$cycloalkyl which is substitute by C$_1$–C$_4$alkyl; C$_2$–C$_{17}$alkenyl; phenyl; phenyl which is substituted by a radical selected from C$_1$–C$_4$alkyl, C$_1$–C$_4$alkoxy and hydroxy; C$_7$–C$_{15}$phenylalkyl; C$_7$–C$_{15}$phenylalkyl which is substituted on the phenyl ring by 1, 2 or 3 radicals selected from C$_1$–C$_4$alkyl, C$_1$–C$_4$alkoxy and hydroxy; or C$_8$–C$_{12}$phenylalkenyl;

R'$_{11}$ is phenyl; phenyl which is substituted by a radical selected from C$_1$–C$_4$alkyl, C$_1$–C$_4$alkoxy and hydroxy; naphthyl; C$_7$–C$_{15}$phenylalkyl; C$_1$–C$_{17}$alkyl; C$_5$–C$_{12}$cycloalkyl;

R$_{111}$ is C$_1$–C$_{12}$alkyl or phenyl or C$_7$–C$_{15}$alkylphenyl;

R$_{12}$ is a direct bond, C$_1$–C$_{18}$alkylene or carbonyl;

R$_{13}$ is C$_1$–C$_{18}$alkyl; C$_3$–C$_{18}$alkenyl; C$_5$–C$_{12}$cycloalkyl; C$_5$–C$_{12}$cycloalkyl, which is substituted by 1, 2 or 3 C$_1$–C$_4$alkyl;

R$_{14}$ is C$_1$–C$_{18}$alkyl; C$_5$–C$_{12}$cycloalkyl; C$_5$–C$_{12}$cycloalkyl, which is substituted by 1, 2 or 3 C$_1$–C$_4$alkyl; C$_2$–C$_{17}$alkenyl; C$_2$–C$_8$hydroxyalkyl; C$_7$–C$_{15}$phenylalkyl; C$_7$–C$_{15}$phenylalkyl, which is substituted on the phenyl ring by 1, 2 or 3 radicals selected from C$_1$–C$_4$alkyl, C$_1$–C$_4$alkoxy;

R'$_{14}$ is hydrogen or has one of the meanings given for R$_{14}$;

R$_{16}$ is C$_1$–C$_{18}$alkyl or C$_3$–C$_8$alkenyl;

R$_{17}$ is hydrogen or C$_1$–C$_4$alkyl;

R'$_{17}$ embraces the meanings given for R$_{13}$ above or is hydrogen or one equivalent of a metal of main group I or II of the periodic system;

when m is 2, X is C$_2$–C$_{18}$alkylene; C$_4$–C$_{12}$alkylene interrupted by oxygen, phenylene, C$_5$–C$_{12}$cycloalkylene, S, NR'$_{14}$ and/or substituted by OH, C$_1$–C$_{18}$alkoxy, —N(R'$_{14}$)$_2$, —OCO—R$_{11}$, —COR$_{11}$, —COOR'$_{17}$, CN, —(O)$_i$—P(=O)$_i$(OR$_{111}$)$_2$, C$_5$–C$_{12}$cycloalkoxy, allyloxy, halogen, —COOH, —CON(R'$_{14}$)$_2$, phenoxy and/or C$_1$–C$_{18}$alkyl-, C$_1$–C$_{18}$alkoxy- or halo-substituted phenoxy; or X is —P(=O)$_i$(OR$_{111}$)—; C$_5$–C$_{12}$cycloalkylene; phenylene; C$_5$–C$_{12}$cycloalkylene-C$_1$–C$_4$alkylene; phenylene-C$_1$–C$_4$alkylene; C$_2$–C$_8$alkylene interrupted by C$_5$–C$_{12}$cycloalkylene and/or phenylene; C$_5$–C$_{12}$cycloalkylene-E-C$_5$–C$_{12}$cycloalkylene; -phenylene-E-phenylene-, wherein E is C$_1$–C$_4$alkylene, —O—, —S—, —SO$_2$—, —CO—; or X is carbonyl or C$_1$–C$_7$alkylene-carbonyl or a group of formulae IVa–IVi —CO—R$_{18}$—CO— (IVa)

—COO—R$_{19}$—OCO— (IVb)

—CONH—R$_{20}$—NHCO— (IVc)

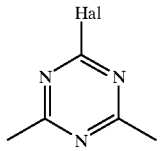 (IVd)

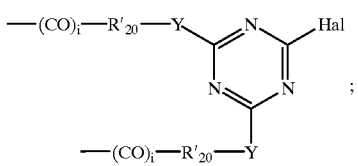 (IVe)

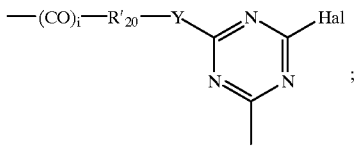 (IVf)

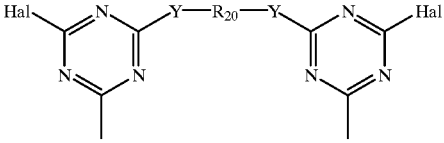 (IVg)

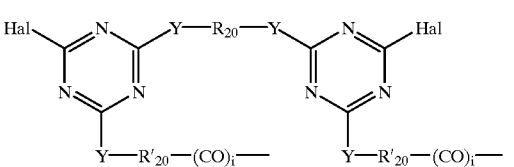 (IVh)

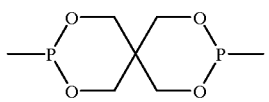 (IVi)

in which i is 0 or 1;

R$_{18}$ is a direct bond; C$_1$–C$_{22}$alkylene; C$_2$–C$_{22}$alkylene interrupted by oxygen, phenylene, C$_5$–C$_{12}$cycloalkylene, sulfur, NR'$_{14}$ and/or substituted by OH, C$_1$–C$_{18}$alkoxy, —N(R'$_{14}$)$_2$, —OCO—R$_{11}$, —COR$_{11}$, —COOR$_{13}$, CN, —(O)$_i$—P(=O)$_i$(OR$_{111}$)$_2$, C$_5$–C$_{12}$cycloalkoxy, allyloxy, halogen, —COOH, —CON(R'$_{14}$)$_2$, phenoxy, and/or phenoxy which is substituted by C$_1$–C$_{18}$alkyl, C$_1$–C$_{18}$alkoxy or halogen; or R$_{18}$ is C$_2$–C$_8$alkenylene; C$_2$–C$_8$alkenylene substituted by R$_{21}$; C$_2$–C$_8$alkylene substituted by R$_{21}$; C$_5$–C$_{12}$cycloalkylene; C$_5$–C$_{12}$cycloalkenylene; or phenylene;

$R_{19}$ is $C_2$–$C_{12}$alkylene; $C_4$–$C_{12}$alkylene interrupted by oxygen, phenylene and/or $C_5$–$C_{12}$cycloalkylene; $C_5$–$C_{12}$cycloalkylene; bis($C_5$–$C_{12}$cycloalkylene)-$C_1$–$C_4$alkylene;

$R_{20}$ is $C_2$–$C_{12}$alkylene; $C_4$–$C_{18}$alkylene interrupted by O, $NR'_{14}$, S, $C_5$–$C_{12}$cycloalkylene or/and phenylene; or $R_{20}$ is $C_5$–$C_{12}$cycloalkylene; or phenylene;

$R'_{20}$ is $C_2$–$C_{12}$alkylene; $C_5$–$C_{12}$cycloalkylene; phenylene; and if i is 1, $R'_{20}$ additionally embraces methylene;

$R_{21}$ is phenyl; phenyl which is substituted by 1, 2 or 3 radicals selected from $C_1$–$C_4$alkyl, $C_1$–$C_4$alkoxy, di($C_1$–$C_4$alkyl)amino, nitro, hydroxy; or is naphthyl; or naphthyl which is substituted by $C_1$–$C_4$alkyl, $C_1$–$C_4$alkoxy, di($C_1$–$C_4$alkyl)amino, nitro; or $R_{21}$ is thienyl; phenoxyphenyl; thiophen-2-yl; phenylthiophenyl; benzo[b]thiophen-2-yl; benzofuran-2-yl; 9H-fluorenyl; biphenylyl; 10-($C_1$–$C_8$alkyl)-10H-phenothiazinyl;

and if the linking group Z or W is a direct bond, X also may be $C_1$alkylene or Y;

when m is 3, X is $C_3$–$C_{18}$alkanetriyl; P; PO; $C_4$–$C_{18}$triacyl; 1,3,5-triazine-2,4,6-triyl; or a group of formula

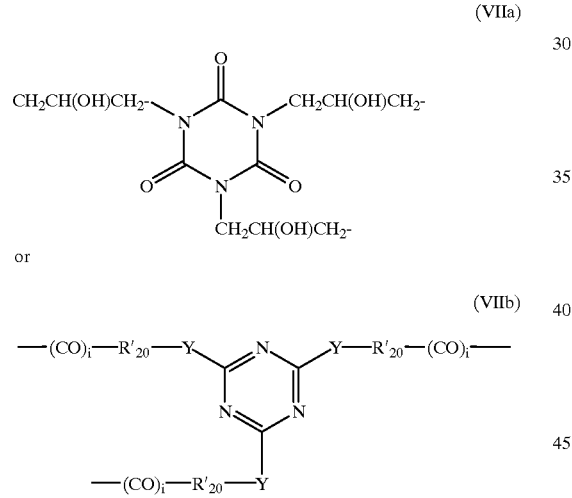

(VIIa)

or (VIIb)

or a trivalent residue of the formula VIIc

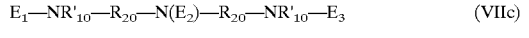 (VIIc)

wherein $E_1$, $E_2$ and $E_3$, independently of one another, are a group of formula IVf;

when m is 4, X is $C_5$–$C_{18}$alkanetetryl; $C_6$–$C_{18}$tetraacyl; or a group of the formula

 (VIIb)

wherein $Z_1$ and $Z_2$ are each, independently of one another, 1,3,5-triazine-2,4,6-triyl or a group of the formula VIIIc or VIIId

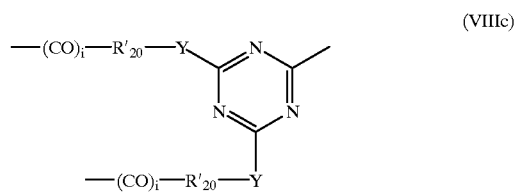

(VIIIc)

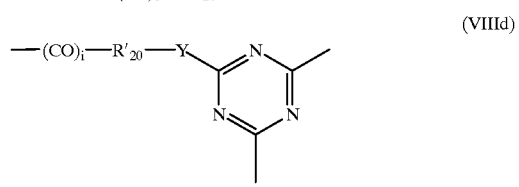

(VIIId)

and the group of formula VIIIc–d is attached via a bond from the triazine ring to the nitrogen atom in formula VIIIb;

when m is 5, X is $C_5$–$C_{18}$alkanepentayl; or $C_7$–$C_{18}$pentaacyl;

when m is 6, X is $C_9$–$C_{18}$hexaacyl; or a hexavalent residue of the formula IXa or IXb

 (IXa)

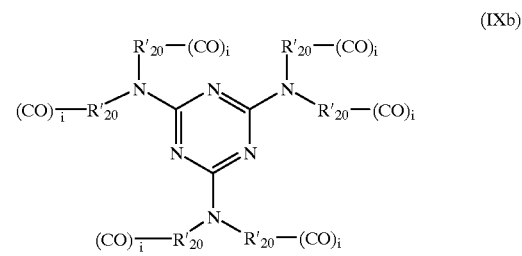

(IXb)

wherein $Z_1$, $Z_2$ and $Z_3$, independently of one another, are 1,3,5-triazine-2,4,6-triyl or a group of the formula VIIIc or VIIId, which is attached via a bond from the triazine ring to the nitrogen atom in formula IXa;

when m is 7, X is $C_{10}$–$C_{18}$heptaacyl;

when m is 8, X is $C_9$–$C_{18}$octoacyl; or an octovalent residue of the formula Xa or Xb

 (Xa)

(Xb)

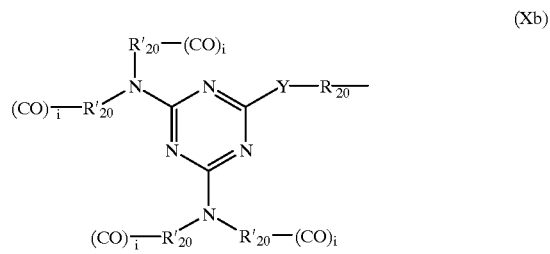

-continued
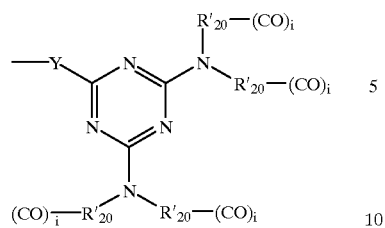
wherein $Z_1$, $Z_2$, $Z_3$ and $Z_4$, independently of one another, are 1,3,5-triazine-2,4,6-triyl or a group of the formula VIIIc or VIIId, which is attached via a bond from the triazine ring to the nitrogen atom in formula Xa; and
D is a group of the formula
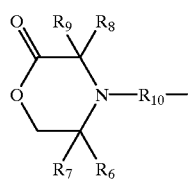 (XIa)
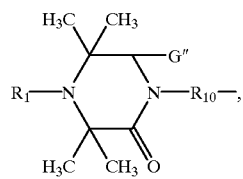 (XIc)
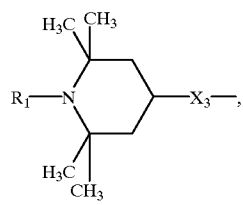 (XId)
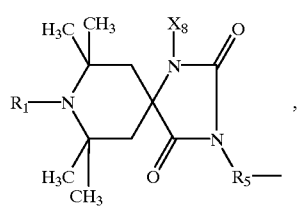 (XIe)
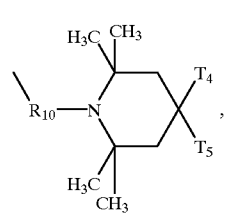 (XIf)
-continued
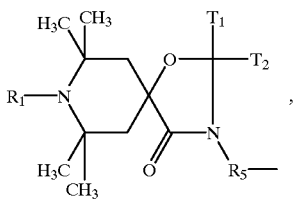 (XIg)
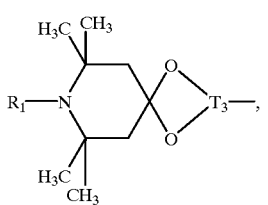 (XIh)
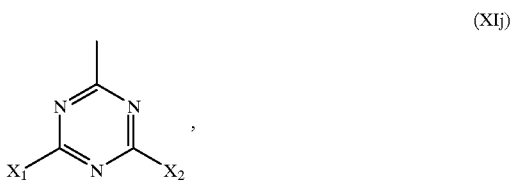 (XIj)
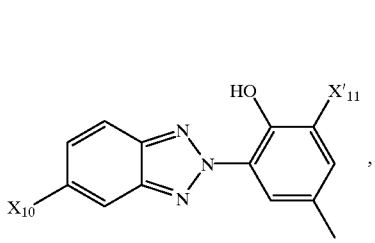 (XIk)
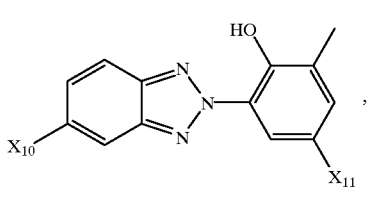 (XIm)
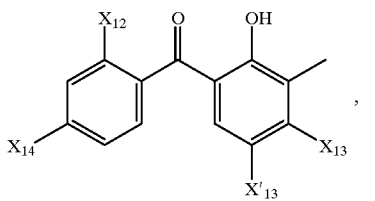 (XIn)
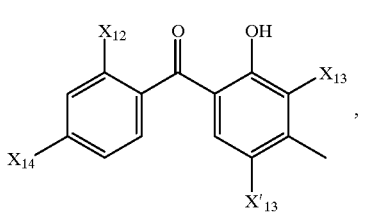 (XIo)

wherein

G" is hydrogen or =O;

R' is C$_1$–C$_{18}$alkyl or cyclohexyl;

R' is tert. C$_4$–C$_{18}$alkyl or cyclohexyl;

T$_1$ and T$_2$, independently, are H; C$_1$–C$_{18}$alkyl; phenyl-C$_1$–C$_4$alkyl; or naphthyl or phenyl which is unsubstituted or substituted by halogen or C$_1$–C$_4$alkyl; or T$_1$ and T$_2$ together with the linking carbon atom form a C$_5$–C$_{12}$cycloalkane ring;

T$_3$ is C$_2$–C$_8$alkanetriyl;

T$_4$ is H, C$_1$–C$_{18}$alkoxy, C$_3$–C$_8$alkenyloxy or benzyloxy; and

T$_5$ is as defined for T$_4$, or T$_4$ and T$_5$ together are —O—C$_2$–C$_8$alkylene-O—, and if T$_4$ is H, T$_5$ additionally embraces —OH and —NR'$_{10}$—CO—R'$_{11}$, where R'$_{11}$ is C$_1$–C$_{18}$alkyl, C$_2$–C$_4$alkenyl or phenyl;

X$_1$ is a group of formula (XId); and

X$_2$ is as defined for X$_1$ or is C$_1$–C$_{18}$alkoxy or —N(R'$_{14}$)$_2$;

X$_3$ is —NR'$_{10}$—, —NX$_6$—, —O—, or a radical of the formula —O—CO—X$_5$—CO—O—X$_6$, where X$_5$ is C$_1$–C$_{12}$alkanetriyl and X$_6$ is a radical of the formula;

X$_8$ is H, C$_1$–C$_{18}$alkyl, C$_7$–C$_{11}$phenylalkyl, C$_2$–C$_6$alkoxyalkyl or C$_5$–C$_{12}$cycloalkyl;

X$_{10}$ is H, Cl, C$_1$–C$_4$alkyl, C$_1$–C$_4$alkoxy;

X$_{11}$ is C$_1$–C$_{12}$alkyl;

X'$_{11}$ is H or C$_1$–C$_{12}$alkyl;

X$_{12}$ is H or OH;

X$_{13}$ is H, Cl, OH or C$_1$–C$_{18}$alkoxy;

X'$_{13}$ is H, Cl or C$_1$–C$_4$alkyl;

X$_{14}$ is H, Cl, OH or C$_1$–C$_{18}$alkoxy;

X$_{15}$ and X$_{17}$, independently, are H, OH, Cl, CN, phenyl, C$_1$–C$_6$alkyl, C$_1$–C$_{18}$alkoxy, C$_4$–C$_{22}$alkoxy interrupted by O and/or substituted by OH, or are C$_2$–C$_{20}$alkanoylamino or C$_7$–C$_{14}$phenylalkoxy;

X$_{16}$ and X$_{18}$, independently, are H, OH, Cl, C$_1$–C$_6$alkyl or C$_1$–C$_6$alkoxy;

X$_{21}$, X$_{22}$ and X$_{23}$, independently, are H, C$_1$–C$_{18}$alkyl or C$_1$–C$_{18}$alkoxy;

X$_{24}$ and X$_{25}$, independently, are H or C$_1$–C$_8$alkyl; and

X$_{26}$ is H, C$_1$–C$_8$alkyl, phenyl, C$_7$–C$_{11}$phenylalkyl, cyclohexyl or —N(R'$_{14}$)$_2$;

and if X$_{25}$ is in ortho-position to X$_{26}$, X$_{25}$ can form, together with X$_{26}$ and the carbon atoms they are attached to, a phenyl ring.

2. A compound of formula A, B, C or D according to claim 1, wherein

R$_2$, R$_4$, R$_5'$, R$_6$, R$_7$, R$_8$ and R$_9$ are, independently of one another, C$_1$–C$_{18}$alkyl, C$_3$–C$_8$alkenyl, C$_5$–C$_{12}$cycloalkenyl, or C$_5$–C$_{12}$cycloalkyl; or R$_2$ and R$_3$, R$_4$ and R$_5'$, R$_6$ and R$_7$, R$_8$ and R$_9$ form, together with the carbon atom they are attached to, $C_5$–$C_{12}$cycloalkylene;

$R_3$ is $C_1$–$C_8$hydroxyalkyl, $C_1$–$C_{18}$alkyl or $C_5$–$C_{12}$cycloalkyl;

$R_5$ is $C_1$–$C_4$alkylene; $C_1$–$C_4$alkylene-CO—; and in formula A also may be a direct bond;

$R_{10}$ is $C_2$–$C_8$alkylene; $C_1$–$C_8$alkylene-CO—;

$R'_{10}$ is hydrogen or $C_1$–$C_8$alkyl or $C_5$–$C_{12}$cycloalkyl;

W is —O— or —$NR'_{14}$— and, if m is not 1, W can also be a direct bond;

X' is as defined for X below;

Y is —O— or —$NR'_{14}$—;

Z and Z', independently, are a direct bond or have a meaning given for Y;

when m is 1, X is $C_1$–$C_{18}$alkyl; $C_1$–$C_{18}$alkyl substituted by $C_1$–$C_{18}$alkoxy, —OH, —OCO—$R_{11}$, —COR$_{11}$, —COOR$_{13}$CN, $C_5$–$C_{12}$cycloalkoxy, allyloxy, halogen, —CON($R'_{14}$)$_2$, phenoxy; or X is $C_3$–$C_{30}$alkyl which is interrupted by —O— and can be substituted by OH; $C_5$–$C_{12}$cycloalkyl; $C_3$–$C_6$alkenyl; glycidyl; $C_7$–$C_{15}$phenylalkyl; $C_7$–$C_{15}$phenylalkyl, which is substituted on the phenyl ring by a radical selected from $C_1$–$C_4$alkyl and $C_1$–$C_4$alkoxy; or is a group of formulae IIIa–IIId —CO—$R_{11}$ (IIIa)

—$R_{12}$—COO—$R_{13}$ (IIIb)

—CO—NH—$R_{14}$ (IIIc)

—CO—$R_{18}$—COO—$R'_{17}$ (IIId);

when m is 2, X is $C_2$–$C_{18}$alkylene; $C_4$–$C_{12}$alkylene interrupted by oxygen, phenylene, $C_5$–$C_{12}$cycloalkylene, S and/or substituted by $C_1$–$C_{18}$alkoxy, —OCO—$R_{11}$, —COR$_{11}$, —COOR'$_{17}$, CN, $C_5$–$C_{12}$cycloalkoxy, allyloxy, halogen, —CON($R'_{14}$)$_2$, phenoxy and/or $C_1$–$C_{18}$alkyl-, $C_1$–$C_{18}$alkoxy- or halo-substituted phenoxy; or X is $C_5$–$C_{12}$cycloalkylene; phenylene; $C_5$–$C_{12}$cycloalkylene-$C_1$–$C_4$alkylene; phenylene-$C_1$–$C_4$alkylene; $C_2$–$C_8$alkylene interrupted by $C_5$–$C_{12}$cycloalkylene and/or phenylene; $C_5$–$C_{12}$cycloalkylene-E-$C_5$–$C_{12}$cycloalkylene; -phenylene-E-phenylene-, wherein E is $C_1$–$C_4$alkylene, —O—, —S—, —SO$_2$—, —CO—; or X is carbonyl or $C_1$–$C_7$alkylene-carbonyl or a group of formulae IVa–IVd;

—CO—$R_{18}$—CO— (IVa)

—COO—$R_{19}$—OCO— (IVb)

—CONH—$R_{20}$—NHCO— (IVc)

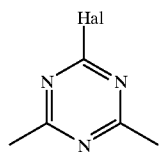
(IVd)

and if the linking group Z or W is a direct bond, X also may be $C_1$alkylene or Y;

when m is 3, X is $C_3$–$C_{18}$alkanetriyl; P; PO; $C_4$–$C_{18}$triacyl; 1,3,5-triazine-2,4,6-triyl; or a group of formula (VIIb);

when m is 4, X is $C_5$–$C_{18}$alkanetetryl; $C_6$–$C_{18}$tetraacyl; or a group of the formula $Z_1$—Y—$R_{20}$—Y—$Z_2$ (VIIIb);

when m is 6, X is $C_9$–$C_{18}$hexaacyl; or a hexavalent residue of the formula IXa' or IXb $Z_1$—$NR'_{10}$—$R_{20}$—$N(Z_2)$—$R_{20}$—$NR'_{10}$—$Z_3$ (IXa');

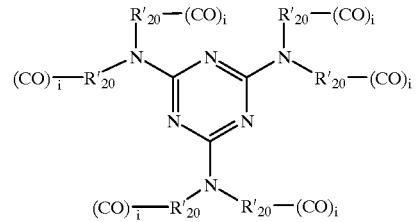
(IXb)

when m is 8, X is $C_9$–$C_{18}$octoacyl; or an octovalent residue of the formula Xa' or Xb'

$Z_1$—$NR'_{10}$—$R_{20}$—$N(Z_2)$—$R_{20}$—$N(Z_3)$—$R_{20}$—$NR'_{10}$—$Z_4$ (Xa')

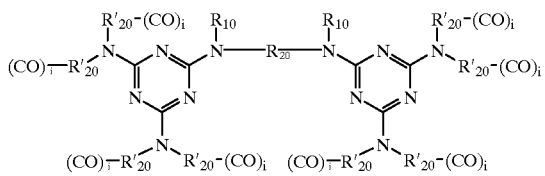
(Xb')

i is 0 or 1;

$R_{11}$ is hydrogen; $C_1$–$C_{18}$alkyl; $C_1$–$C_{18}$alkyl substituted by $C_1$–$C_{18}$alkoxy, —OCO—$R_{111}$, —COR$_{111}$, CN, $C_5$–$C_{12}$cycloalkoxy, allyloxy, halogen, —COOH, —CON($R'_{14}$)$_2$, phenoxy; $C_5$–$C_{12}$cycloalkyl; $C_5$–$C_{12}$cycloalkyl, which is substituted by 1, 2 or 3 $C_1$–$C_4$alkyl; $C_2$–$C_{17}$alkenyl; phenyl; phenyl which is substituted by 1, 2 or 3 radicals selected from $C_1$–$C_4$alkyl, $C_1$–$C_4$alkoxy and hydroxy; $C_7$–$C_{15}$phenylalkyl; $C_7$–$C_{15}$phenylalkyl, which is substituted on the phenyl ring by 1, 2 or 3 radicals selected from $C_1$–$C_4$alkyl, $C_1$–$C_4$alkoxy and hydroxy; or $C_8$–$C_{12}$phenylalkenyl;

$R'_{11}$ is phenyl; phenyl which is substituted by 1, 2 or 3 radicals selected from $C_1$–$C_4$alkyl, $C_1$–$C_4$alkoxy and hydroxy; naphthyl; $C_7$–$C_{15}$phenylalkyl; $C_1$–$C_{17}$alkyl; $C_5$–$C_{12}$cycloalkyl;

$R_{111}$ is $C_1$–$C_{12}$alkyl or phenyl or $C_7$–$C_{15}$alkylphenyl;

$R_{12}$ is a direct bond, $C_1$–$C_{18}$alkylene or carbonyl;

$R_{13}$ is $C_1$–$C_{18}$alkyl; $C_3$–$C_{18}$alkenyl; $C_5$–$C_{12}$cycloalkyl; $C_5$–$C_{12}$cycloalkyl, which is substituted by 1, 2 or 3 $C_1$–$C_4$alkyl;

$R_{14}$ is $C_1$–$C_{18}$alkyl; $C_5$–$C_{12}$cycloalkyl; $C_5$–$C_{12}$cycloalkyl, which is substituted by 1, 2 or 3 $C_1$–$C_4$alkyl; $C_3$–$C_{17}$alkenyl; $C_2$–$C_8$hydroxyalkyl; $C_7$–$C_{15}$phenylalkyl;

$R'_{14}$ is hydrogen or has one of the meanings given for $R_{14}$;

$R'_{17}$ embraces the meanings given for $R_{13}$ above or is hydrogen or one equivalent of a metal of main group I or II of the periodic system;

$R_{18}$ is a direct bond; $C_1$–$C_{22}$alkylene; $C_2$–$C_{22}$alkylene interrupted by oxygen, phenylene, C$_5$–C$_{12}$cycloalkylene, S, NR'$_{14}$ and/or substituted by OH, C$_1$–C$_{18}$alkoxy, —N(R'$_{14}$)$_2$, —OCO—R$_{11}$, —COR$_{11}$, —COOR$_{13}$, CN, —(O)$_i$—P(=O)$_i$(OR$_{111}$)$_2$, C$_5$–C$_{12}$cycloalkoxy, allyloxy, halogen, —COOH, —CON(R'$_{14}$)$_2$, phenoxy and/or C$_1$–C$_{18}$alkyl-, C$_1$–C$_{18}$alkoxy- or halo-substituted phenoxy; C$_2$–C$_8$alkenylene; C$_2$–C$_8$alkenylene substituted by R$_{21}$; C$_2$–C$_8$alkylene substituted by R$_{21}$; cyclohexylene; cyclohexenylene or phenylene; or R$_{19}$ is C$_2$–C$_{12}$alkylene; C$_4$–C$_{12}$alkylene interrupted by oxygen, phenylene and/or C$_5$–C$_{12}$cycloalkylene; C$_5$–C$_{12}$cycloalkylene; bis(C$_5$–C$_{12}$cycloalkylene)-C$_1$–C$_4$alkylene;

R$_{20}$ is C$_2$–C$_{12}$alkylene; C$_5$–C$_{12}$cycloalkylene; or phenylene;

R'$_{20}$ is C$_2$–C$_{12}$alkylene; C$_5$–C$_{12}$cycloalkylene; phenylene; and if i is 1, R'$_{20}$ additionally embraces methylene;

R$_{21}$ is phenyl; phenyl which is substituted by 1, 2 or 3 radicals selected from C$_1$–C$_4$alkyl, C$_1$–C$_4$alkoxy, di(C$_1$–C$_4$alkyl)amino, nitro, hydroxy; or is naphthyl; or naphthyl which is substituted by C$_1$–C$_4$alkyl, C$_1$–C$_4$alkoxy, di(C$_1$–C$_4$alkyl)amino, nitro; or R$_{21}$ is thienyl; phenoxyphenyl; thiophen-2-yl; phenylthiophenyl; benzo[b]thiophen-2-yl; benzofuran-2-yl; 9H-fluorenyl; biphenylyl; 10-(C$_1$–C$_8$alkyl)-10H-phenothiazinyl;

D is a group of the formula XIa, XIc, XId, XIf, XIj, XIk, XIm, XIn, XIo, XIp, XIs, XIt or XIu.

3. Compound according to claim 1 corresponding to the formula I II or III

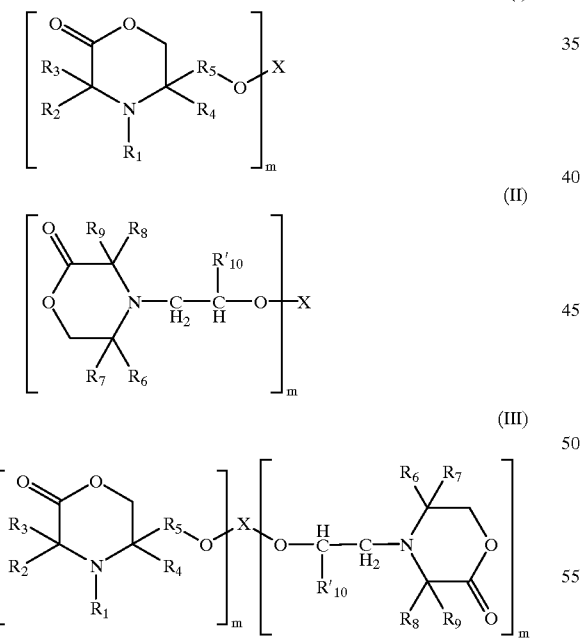

where
m is the valency of X and is an integer from the range 1–6;
x and y are each integers from the range 1–5 obeying the condition x+y=m;
R$_1$ is hydrogen; C$_1$–C$_{18}$alkyl; oxyl; OH; CH$_2$CN; C$_1$–C$_{18}$alkoxy; C$_5$–C$_{12}$cycloalkoxy; C$_3$–C$_8$alkenyl; C$_3$–C$_8$alkynyl; C$_7$–C$_{12}$phenylalkyl; C$_7$–C$_{15}$phenylalkyl, which is substituted on the phenyl ring by 1, 2 or 3 radicals selected from C$_1$–C$_4$alkyl and C$_1$–C$_4$alkoxy; C$_7$–C$_{15}$phenylalkoxy; C$_7$–C$_{15}$phenylalkoxy, which is substituted on the phenyl ring by 1, 2 or 3 radicals selected from C$_1$–C$_4$alkyl and C$_1$–C$_4$alkoxy; or R$_1$ is C$_1$–C$_8$alkanoyl; C$_3$–C$_5$alkenoyl; C$_1$–C$_{18}$alkanoyloxy; glycidyl; or a group —CH$_2$CH(OH)—G, in which G is hydrogen, methyl or phenyl;

R$_2$, R$_3$, R$_4$, R$_6$, R$_7$, R$_8$ and R$_9$ are, independently of one another, C$_1$–C$_{18}$alkyl or C$_5$–C$_{12}$cycloalkyl;

or R$_2$ and R$_3$, R$_6$ and R$_7$, R$_8$ and R$_9$ form, together with the carbon atom they are attached to, C$_5$–C$_{12}$cycloalkylene;

R$_5$ is C$_1$–C$_4$alkylene;

R'$_{10}$ is hydrogen or C$_1$–C$_4$alkyl;

when m is 1, X is C$_1$–C$_{18}$alkyl; C$_5$–C$_{12}$cycloalkyl; C$_3$–C$_6$alkenyl; glycidyl; C$_7$–C$_{15}$phenylalkyl; C$_7$–C$_{15}$phenylalkyl, which is substituted on the phenyl ring by 1, 2 or 3 radicals selected from C$_1$–C$_4$alkyl and C$_1$–C$_4$alkoxy; or is a group of formulae IIIa–IIId

 (IIIa)

 (IIIb)

 (IIIc)

 (IIId)

wherein

R$_{11}$ is hydrogen; C$_1$–C$_{17}$alkyl; C$_5$–C$_{12}$cycloalkyl; C$_5$–C$_{12}$cycloalkyl, which is substituted by 1, 2 or 3 C$_1$–C$_4$alkyl; C$_2$–C$_{17}$alkenyl; phenyl; phenyl which is substituted by 1, 2 or 3 radicals selected from C$_1$–C$_4$alkyl, C$_1$–C$_4$alkoxy and hydroxy; C$_7$–C$_{15}$phenylalkyl; C$_7$–C$_{15}$phenylalkyl, which is substituted on the phenyl ring by 1, 2 or 3 radicals selected from C$_1$–C$_4$alkyl, C$_1$–C$_4$alkoxy and hydroxy; or C$_8$–C$_{12}$phenylalkenyl;

R$_{12}$ is a direct bond, C$_1$–C$_{18}$alkylene or carbonyl;

R$_{13}$ is C$_1$–C$_{18}$alkyl; C$_3$–C$_{18}$alkenyl; C$_5$–C$_{12}$cycloalkyl; C$_5$–C$_{12}$cycloalkyl, which is substituted by 1, 2 or 3 C$_1$–C$_4$alkyl;

R$_{14}$ is C$_1$–C$_{18}$alkyl; C$_5$–C$_{12}$cycloalkyl; C$_5$–C$_{12}$cycloalkyl, which is substituted by 1, 2 or 3 C$_1$–C$_4$alkyl; C$_2$–C$_{17}$alkenyl; C$_7$–C$_{15}$phenylalkyl; C$_7$–C$_{15}$phenylalkyl, which is substituted on the phenyl ring by 1, 2 or 3 radicals selected from C$_1$–C$_4$alkyl, C$_1$–C$_4$alkoxy;

R$_{15}$ is C$_1$–C$_4$alkylene; C$_2$–C$_4$oxaalkylene; C$_5$–C$_{12}$cycloalkylene; C$_5$–C$_{12}$cycloalkenyl phenylene; or a group of the formulae —CH$_2$—CH(R$_{16}$)— or —CH=C(R$_{17}$)—;

R$_{16}$ is C$_1$–C$_{18}$alkyl or C$_3$–C$_8$alkenyl;

R$_{17}$ is hydrogen or C$_1$–C$_4$alkyl;

R'$_{17}$ embraces the meanings given for R$_{13}$ above or is hydrogen or one equivalent of a metal of main group I or II of the periodic system;

when m is 2, X is C$_2$–C$_{12}$alkylene; C$_4$–C$_{12}$alkylene interrupted by oxygen, phenylene and/or C$_5$–C$_{12}$cycloalkylene; C$_5$–C$_{12}$cycloalkylene; bis (C$_5$–C$_{12}$cycloalkylene)-C$_1$–C$_4$alkylene; or is a group of formulae IVa–IVf

 (IVa)

 (IVb)

—CONH—R₂₀—NHCO— (IVc)

—C_tH_{2t}—CO— (IVd)

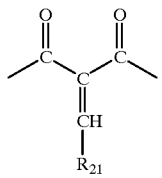
(IVe)

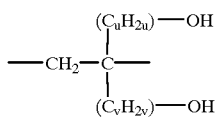
(IVf)

wherein t is zero or an integer from 1 to 7;

u and v, independently of one another, are integers from the range 1–4;

R₁₈ is a direct bond; $C_1-C_{22}$alkylene; $C_2-C_8$alkenylene; cyclohexylene; cyclohexenylene or phenylene;

R₁₉ is $C_2-C_{12}$alkylene; $C_4-C_{12}$alkylene interrupted by oxygen, phenylene and/or $C_5-C_{12}$cycloalkylene; $C_5-C_{12}$cycloalkylene; bis($C_5-C_{12}$cycloalkylene)-$C_1-C_4$alkylene;

R₂₀ is $C_2-C_{12}$alkylene; $C_5-C_{12}$cycloalkylene; or phenylene;

R₂₁ is phenyl; phenyl which is substituted by 1, 2 or 3 radicals selected from $C_1-C_4$alkyl, $C_1-C_4$alkoxy, di($C_1-C_4$alkyl)amino, nitro, hydroxy; or is naphthyl; or naphthyl which is substituted by $C_1-C_4$alkyl, $C_1-C_4$alkoxy, di($C_1-C_4$alkyl)amino, nitro; or R₂₁ is thienyl; phenoxyphenyl; phenylthiophenyl; benzo[b]thiophen-2-yl; benzofuran-2-yl; 9H-fluorenyl; biphenyl; 10-($C_1-C_8$alkyl)-10H-phenothiazinyl; or is phenyl which is substituted by 1 or 2 radicals of the formulae

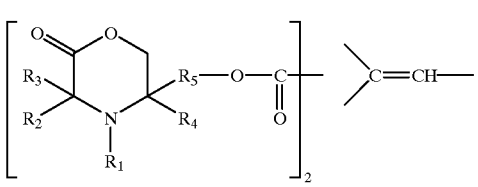
(V)

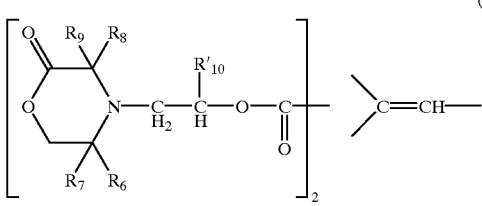
(VI)

when m is 3, X is aliphatic $C_4-C_{18}$triacyl, aromatic $C_9-C_{18}$triacyl or a group of the formula VII

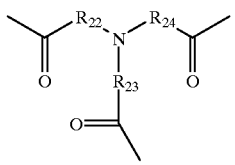
(VII)

wherein R₂₂, R₂₃ and R₂₄, independently of each other, are $C_1-C_7$alkylene;

when m is 4, X is aliphatic $C_6-C_{18}$tetraacyl, aromatic $C_{10}-C_{18}$tetraacyl or a group of the formula VIII

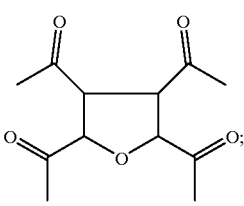
(VIII)

when m is 5, X is aliphatic $C_7-C_{18}$pentaacyl or aromatic $C_{10}-C_{16}$pentaacyl;

when m is 6, X is aliphatic $C_9-C_{18}$hexaacyl or aromatic $C_{12}-C_{18}$hexaacyl.

4. Compound of formula A, B, C or D according to claim 1, wherein m is the valency of X and is an integer from the range 1–4 or is 6 or 8;

x is 1 or 2 and y is 1;

R₁ is hydrogen; $C_1-C_{18}$alkyl; oxyl; OH; $C_1-C_{18}$alkoxy; $C_5-C_{12}$cycloalkoxy; $C_3-C_8$alkenyl; $C_3-C_8$alkynyl; $C_3-C_8$alkenyloxy; $C_7-C_{12}$phenylalkyl; $C_2-C_8$alkanoyl; $C_3-C_5$alkenoyl; or glycidyl R₂, R₄, R₅', R₆, R₇, R₈ and R₉ are, independently of one another, $C_1-C_{18}$alkyl, $C_3-C_8$alkenyl, or $C_5-C_{12}$cycloalkyl;

R₃ is $C_1-C_8$hydroxyalkyl, $C_1-C_{18}$alkyl or $C_5-C_{12}$cycloalkyl;

R₅ is $C_1-C_4$alkylene; $C_1-C_4$alkylene-CO—; and in formula A also may be a direct bond;

R₁₀ is $C_2-C_8$alkylene; $C_1-C_8$alkylene-CO—;

W is —O— or —NR'₁₄— and, if m is not 1, W can also be a direct bond;

X' is as defined for X below;

Y is —O— or —NR'₁₄—;

Z and Z', independently, are a direct bond or have a meaning given for Y;

when m is 1, X is $C_1-C_{18}$alkyl; $C_1-C_{18}$alkyl substituted by $C_1-C_{18}$alkoxy, —OH, —OCO—R₁₁, CN, $C_5-C_{12}$cycloalkoxy, allyloxy, halogen, phenoxy; or X is $C_3-C_{30}$alkyl which is interrupted by —O— and can be substiituted by OH; $C_5-C_{12}$cycloalkyl; $C_3-C_6$alkenyl; glycidyl; $C_7-C_{15}$phenylalkyl; or is a group of formula IIIa or IIId —CO—R₁₁ (IIIa)

—CO—R₁₈—COO—R'₁₇ (IIId);

R₁₁ is $C_1-C_{18}$alkyl; $C_1-C_{18}$alkyl substituted by $C_1-C_{18}$alkoxy, —OCO—R₁₁₁, —COR₁₁₁, CN, $C_5$–$C_{12}$cycloalkoxy, —COOH, $C_5$–$C_{12}$cycloalkyl; $C_5$–$C_{12}$cycloalkyl, which is substituted by 1, 2 or 3 $C_1$–$C_4$alkyl; $C_2$–$C_8$alkenyl; phenyl; $C_7$–$C_{15}$phenylalkyl;

$R'_{14}$ is hydrogen or $C_1$–$C_{18}$alkyl; cyclohexyl; $C_2$–$C_8$hydroxyalkyl; $C_7$–$C_{15}$phenylalkyl;

$R'_{17}$ is hydrogen or $C_1$–$C_{12}$alkyl or an equivalent of a sodium, potassium, magnesium or calcium ion;

when m is 2, X is $C_2$–$C_{18}$alkylene; $C_4$–$C_{12}$alkylene interrupted by oxygen, phenylene, $C_5$–$C_{12}$cycloalkylene, S and/or substituted by $C_1$–$C_{18}$alkoxy, —OH, —OCO—$R_{11}$, CN, $C_5$–$C_{12}$cycloalkoxy, allyloxy, halogen, phenoxy; or X is $C_5$–$C_{12}$cycloalkylene; phenylene; $C_5$–$C_{12}$cycloalkylene-$C_1$–$C_4$alkylene; phenylene-$C_1$–$C_4$alkylene; $C_2$–$C_8$alkylene interrupted by $C_5$–$C_{12}$cycloalkylene and/or phenylene; $C_5$–$C_{12}$cycloalkylene-E-$C_5$–$C_{12}$cycloalkylene; -phenylene-E-phenylene-, wherein E is $C_1$–$C_4$alkylene, —O—, —S—, —SO$_2$—, —CO—; or X is carbonyl or $C_1$–$C_7$alkylene-carbonyl or a group of formula —CO—$R_{18}$—CO— (IVa); wherein $R_{18}$ is a direct bond; $C_1$–$C_{18}$alkylene; $C_4$–$C_{22}$alkylene interrupted by oxygen, phenylene, $C_5$–$C_{12}$cycloalkylene, S; $C_2$–$C_8$alkenylene; $C_2$–$C_8$alkenylene substituted by $R_{21}$; $C_2$–$C_8$alkylene substituted by $R_{21}$; cyclohexylene; or phenylene;

$R_{20}$ and $R'_{20}$, independently, are $C_2$–$C_{12}$alkylene or cyclohexylene; and if i is 1, $R'_{20}$ additionally embraces methylene;

$R_{21}$ is phenyl; phenyl which is substituted by 1, 2 or 3 radicals selected from $C_1$–$C_4$alkyl, $C_1$–$C_4$alkoxy, hydroxy; or is naphthyl; or naphthyl which is substituted by $C_1$–$C_4$alkyl, $C_1$–$C_4$alkoxy; or $R_{21}$ is thienyl; phenylthiophenyl; thiophen-2-yl; benzo[b]thiophen-2-yl; biphenylyl; 10-($C_1$–$C_8$alkyl)-10H-phenothiazinyl;

when m is 3, X is $C_3$–$C_{18}$alkanetriyl; P; PO; $C_4$–$C_{18}$triacyl; 1,3,5-triazine-2,4,6-triyl;

when m is 4, X is $C_5$–$C_{18}$alkanetetryl; $C_6$–$C_{18}$tetraacyl; or a group of the formula

$Z_1$—Y—$R_{20}$—Y—$Z_2$ (VIIIb);

when m is 6, X is a hexavalent residue of the formula IXa' or IXb

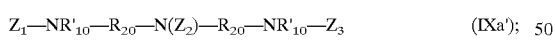
$Z_1$—NR'$_{10}$—$R_{20}$—N($Z_2$)—$R_{20}$—NR'$_{10}$—$Z_3$ (IXa');

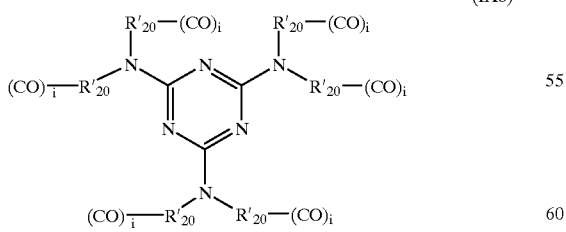
(IXb)

when m is 8, X is octovalent residue of the formula Xa' or Xb'

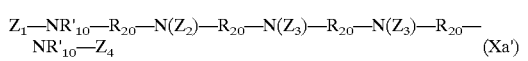
$Z_1$—NR'$_{10}$—$R_{20}$—N($Z_2$)—$R_{20}$—N($Z_3$)—$R_{20}$—N($Z_3$)—$R_{20}$—NR'$_{10}$—$Z_4$ (Xa')

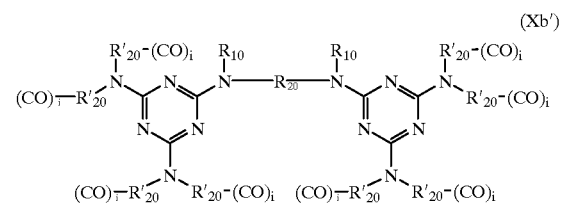
(Xb')

D is a group of the formula XIa, XIc, XId, XIj, XIk, XIm, XIn, XIo, XIp, XIs or XIu;

G" is hydrogen or =O;

R' is cyclohexyl, methyl or tert.-butyl;

R" is cyclohexyl or tert.-butyl;

$X_1$ is a group of formula (XId); and $X_2$ is as defined for $X_1$ or is $C_1$–$C_{18}$alkoxy or —N($R'_{14}$)$_2$;

$X_3$ is —O—;

$X_{10}$ is H, Cl, $C_1$–$C_4$alkyl, $C_1$–$C_4$alkoxy;

$X_{11}$ is $C_1$–$C_{12}$alkyl;

$X'_{11}$ is H or $C_1$–$C_{12}$alkyl;

$X_{12}$ is H or OH;

$X_{13}$ is H, Cl, OH or $C_1$–$C_8$alkoxy;

$X'_{13}$ is H, Cl or $C_1$–$C_4$alkyl;

$X_{14}$ is H, Cl, OH or $C_1$–$C_8$alkoxy;

$X_{15}$ and $X_{17}$, independently, are H, OH, Cl, phenyl, $C_1$–$C_6$alkyl, $C_1$–$C_{18}$alkoxy, $C_4$–$C_{22}$alkoxy interrupted by O and/or substituted by OH, or are $C_7$–$C_{14}$phenylalkoxy; or $C_2$–$C_{20}$alkanoylamino; and $X_{16}$ and $X_{18}$, independently, are H, OH, methyl or $C_1$–$C_6$alkoxy.

5. Compound of formula A, B, C or D according to claim 4, wherein x is 1 and y is 1;

$R_1$ is hydrogen; $C_1$–$C_6$alkyl; oxyl; OH; $C_1$–$C_{18}$alkoxy; cyclohexyloxy; allyl; allyloxy; $C_2$–$C_8$alkanoyl; or glycidyl;

$R_2$, $R_3$, $R_4$, $R_5'$, $R_6$, $R_7$, $R_8$ and $R_9$ are, independently of one another, $C_1$–$C_6$alkyl or cyclohexy;

$R_5$ is $C_1$–$C_4$alkylene; and in formula A also may be a direct bond;

$R_{10}$ is $C_2$–$C_8$alkylene;

W is —O—;

when m is 1, X is $C_1$–$C_{18}$alkyl; $C_1$–$C_8$alkyl substituted by $C_1$–$C_8$alkoxy, —OH, —OCO—$R_{11}$, cyclohexyloxy; $C_7$–$C_{15}$phenylalkyl; or is a group of formula IIIa or IIId

—CO—$R_{11}$ (IIIa)

—CO—$R_{18}$—COO—$R'_{17}$ (IIId);

when m is 2, X is $C_2$–$C_{18}$alkylene; $C_4$–$C_{12}$alkylene interrupted by oxygen; $C_5$–$C_{12}$cycloalkylene; phenylene; cyclohexylene-$C_1$–$C_4$alkylene; phenylene-$C_1$–$C_4$alkylene; $C_2$–$C_8$alkylene interrupted by cyclohexylene and/or phenylene; cyclohexylene-E-cyclohexylene; -phenylene-E-phenylene-, wherein E is $C_1$–$C_4$alkylene, —O—, —S—, —SO$_2$—, —CO—; or X is carbonyl or $C_1$–$C_7$alkylene-carbonyl or a group of formula —CO—$R_{18}$—CO—(IVa);

when m is 3, X is $C_4$–$C_{18}$triacyl; 1,3,5-triazine-2,4,6-triyl;

when m is 4, X is $C_5$–$C_{18}$alkanetetryl; $C_6$–$C_{18}$tetraacyl; or a group of the formula $Z_1—Y—R_{20}—Y—Z_2$ (VIIIb);

when m is 6, X is a hexavalent residue of the formula IXa' or IXb $Z_1—NR'_{10}—R_{20}—N(Z_2)—R_{20}—NR'_{10}—Z_3$ (IXa');

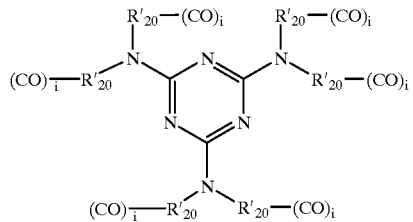
(IXb)

when m is 8, X is octovalent residue of the formula Xa' or Xb'

$Z_1—NR'_{10}—R_{20}—N(Z_2)—R_{20}—N(Z_3)—R_{20}—NR'_{10}—Z_4$ (Xa')

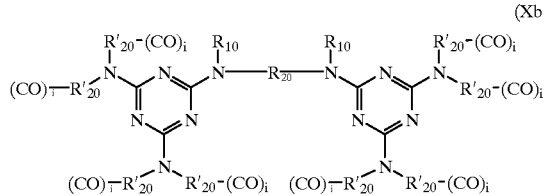
(Xb')

i is 0 or 1;

$R_{11}$, is $C_1-C_{18}$alkyl; $C_1-C_8$alkyl substituted by $C_1-C_8$alkoxy; $C_2-C_8$alkenyl; phenyl; $C_7-C_{15}$phenylalkyl;

$R'_{14}$ is hydrogen or $C_1-C_{18}$alkyl; cyclohexyl; $C_2-C_8$hydroxyalkyl; $C_7-C_{15}$phenylalkyl;

$R_{16}$ is $C_1-C_{18}$alkyl or $C_3-C_8$alkenyl;

$R'_{17}$ is hydrogen or $C_1-C_4$alkyl or an equivalent of a sodium, potassium, magnesium or calcium ion;

$R_{18}$ is a direct bond; $C_1-C_{18}$alkylene; $C_2-C_8$alkenylene; $C_2-C_8$alkenylene substituted by $R_{21}$; $C_2-C_8$alkylene substituted by $R_{21}$; cyclohexylene; or phenylene;

$R_{20}$ and $R'_{20}$, independently, are $C_2-C_{12}$alkylene or cyclohexylene; and if i is 1, $R'_{20}$ additionally embraces methylene;

$R_{21}$ is phenyl; thienyl; thiophen-2-yl;

D is a group of the formula XIa, XIc, XId, XIj, XIk, XIm, XIn, XIo, XIp, XIs or XIu;

G" is hydrogen;

R' is methyl or tert.-butyl;

R" is tert.-butyl;

$X_1$ is a group of formula (XId); and $X_2$ is as defined for $X_1$ or is $—N(R'_{14})_2$;

$X_3$ is —O—;

$X_{10}$ is H, Cl, methyl or methoxy;

$X_{11}$ and $X'_{11}$, independently, are $C_1-C_{12}$alkyl;

$X_{12}$ is H or OH;

$X_{13}$ is H or $C_1-C_8$alkoxy;

$X'_{13}$ is H or $C_1-C_4$alkyl;

$X_{14}$ is H or $C_1-C_8$alkoxy;

$X_{15}$, $X_{17}$, $X_{16}$ and $X_{18}$, independently, are H, phenyl or methyl.

6. A composition comprising

A) an organic material sensitive to damage by light, oxygen and/or heat, and

B) as stabilizer a compound of the formula F according to claim 1.

7. A composition according to claim 6 comprising as organic material a synthetic organic polymer, a reprographic material or a coating material.

8. A composition according to claim 6 comprising from 0.1 to 10% by weight, based on the material to be stabilized, of the stabilizer of component B.

9. A composition according to claim 6 comprising a further component selected from solvents, pigments, dyes, plasticizers, antioxidants, stabilizers, thixotropic agents, levelling assistants, further light stabilizers, metal passivators, phosphites and phosphonites.

10. A composition according to claim 9 comprising as further component a light stabilizer from the class of the 2-hydroxyphenyltriazines and/or 2-hydroxyphenylbenzotriazoles.

11. A process for stabilizing an organic material against damage by light, oxygen and/or heat, which comprises adding to or applying to said material a compound of the formula F according to claim 1.

* * * * *